(12) United States Patent
Stamford et al.

(10) Patent No.: US 6,946,476 B2
(45) Date of Patent: Sep. 20, 2005

(54) HETEROARYL UREA NEUROPEPTIDE Y Y5 RECEPTOR ANTAGONISTS

(75) Inventors: Andrew Stamford, Chatham, NJ (US); Youhao Dong, Keasbey, NJ (US); Stuart W. McCombie, Caldwell, NJ (US); Yusheng Wu, New York, NY (US)

(73) Assignee: Schering Corporation, Kanilworth, NJ (US)

( * ) Notice: Subject to any disclaimer, the term of this patent is extended or adjusted under 35 U.S.C. 154(b) by 10 days.

(21) Appl. No.: 10/177,345

(22) Filed: Jun. 20, 2002

(65) Prior Publication Data

US 2004/0006086 A1 Jan. 8, 2004

Related U.S. Application Data

(63) Continuation-in-part of application No. 10/026,651, filed on Dec. 18, 2001.
(60) Provisional application No. 60/257,308, filed on Dec. 21, 2000.

(51) Int. Cl.[7] ................... C07D 213/02; C07D 409/04; A61K 31/4418; A61K 31/4436; A61P 3/04
(52) U.S. Cl. ...................... 514/318; 514/326; 546/194; 546/213; 546/208; 546/279.7; 546/268.1
(58) Field of Search ................................ 546/194, 208, 546/213, 297.7, 268.1; 514/318, 326

(56) References Cited

U.S. PATENT DOCUMENTS

| 4,405,644 A | 9/1983 | Kabbe et al. ............... 424/322 |
| 4,623,662 A | 11/1986 | De Vries .................... 514/596 |

FOREIGN PATENT DOCUMENTS

| EP | 1 249 233 A1 | 10/2002 |
| WO | WO 97/19682 | 6/1997 |
| WO | WO 98/35957 | 8/1998 |
| WO | WO 99/09024 | 2/1999 |
| WO | WO 99/32111 A1 | 7/1999 |
| WO | WO 99/64394 | 12/1999 |
| WO | WO 00/27845 | 5/2000 |
| WO | WO 01/14376 A1 | 3/2001 |
| WO | WO 01/37826 A1 | 5/2001 |

OTHER PUBLICATIONS

Betancur et al., TIPS vol. 18, 372–386, 1997.*
Wieland et al., (Expert Opin. Investig Drugs 9(6): 1327–1346, 2000.*
West, Anthony R., Solid State Chemistry and its Application, pp. 358, 365, 1998.

* cited by examiner

Primary Examiner—Venkataraman Balasubramanian
(74) Attorney, Agent, or Firm—William Y. Lee

(57) ABSTRACT

The present invention relates to compounds represented by the structural Formula I:

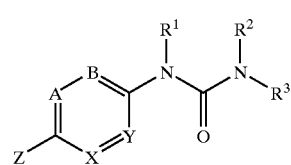

or a pharmaceutically acceptable salt thereof, which are useful for the treatment of metabolic and eating disorders such as obesity and hyperphagia, and for the treatment of diabetes and associated disorders.

21 Claims, No Drawings

HETEROARYL UREA NEUROPEPTIDE Y Y5 RECEPTOR ANTAGONISTS

CROSS REFERENCE TO RELATED APPLICATIONS

This application is a Continuation-in-part of U.S. Ser. No. 10/026,651 filed on Dec. 18, 2001, which claims the benefit of U.S. Provisional Application No. 60/257,308 filed on Dec. 21, 2000.

This invention relates to heteroaryl urea neuropeptide Y Y5 receptor antagonists useful in the treatment of eating disorders, pharmaceutical compositions containing the compounds, and methods of treatment using the compounds.

Neuropeptide Y (NPY) is a 36 amino acid neuropeptide that is widely distributed in the central and peripheral nervous systems. NPY is a member of the pancreatic polypeptide family that also includes peptide YY and pancreatic polypeptide (Wahlestedt, C., and Reis, D., Ann. Rev. Toxicol., 32, 309, 1993). NPY elicits its physiological effects by activation of at least six receptor subtypes designated Y1, Y2, Y3, Y4, Y5 and Y6 (Gehlert, D., Proc. Soc. Exp. Biol. Med., 218, 7, 1998; Michel, M. et al., Pharmacol. Rev., 50, 143, 1998). Central administration of NPY to animals causes dramatically increased food intake and decreased energy expenditure (Stanley, B. and Leibowitz, S., Proc. Natl. Acad. Sci. USA 82: 3940, 1985; Billington et al., Am J. Physiol., 260, R321, 1991). These effects are believed to be mediated at least in part by activation of the NPY Y5 receptor subtype. The isolation and characterization of the NPY Y5 receptor subtype has been reported (Gerald, C. et al., Nature, 1996, 382, 168; Gerald, C. et al. WO 96/16542). Additionally, it has been reported that activation of the NPY Y5 receptor by administration of the Y5—selective agonist [D-Trp$^{32}$]NPY to rats stimulates feeding and decreases energy expenditure (Gerald, C. et al., Nature, 1996, 382, 168; Hwa, J. et al., Am. J. Physiol., 277 (46), R1428, 1999). Hence, compounds that block binding of NPY to the NPY Y5 receptor subtype should have utility in the treatment of eating disorders such as obesity, bulimia nervosa, anorexia nervosa, and in the treatment of disorders associated with obesity such as type II diabetes, insulin resistance, hyperlipidemia, and hypertension.

Published PCT patent application WO 00/27845 describes a class of compounds, characterized therein as spiro-indolines, said to be selective neuropeptide Y Y5 receptor antagonists and useful for the treatment of obesity and the complications associated therewith. Known urea derivatives indicated as possessing therapeutic activity are described in U.S. Pat. No. 4,623,662 (antiatherosclerotic agents) and U.S. Pat. No. 4,405,644 (treatment of lipometabolism).

Provisional application, U.S. Ser. No. 60/232,255 describes a class of substituted urea neuropeptide Y Y5 receptor antagonists.

SUMMARY OF THE INVENTION

This invention relates to compounds of Formula I:

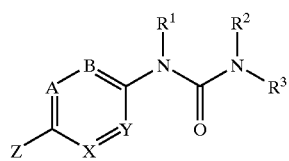

I or a pharmaceutically acceptable salt and/or hydrate of said compound,
wherein
=A-B= is =C(R$^4$)—C(R$^5$)= and —X=Y— is —C(R$^6$)=N—, —N=C(R$^7$)—, —N=N— or —S—, or
=A-B= is =N—C(R$^5$)= and —X=Y— is —N=C(R$^7$)—, —C(R$^6$)=N—, —S— or —O—, or
=A-B= is =C(R$^4$)—N= and —X=Y— is —C(R$^6$)=N—, —S— or —O—, or
=A-B= is =N—N= and —X=Y— is —S— or —O—, or
=A-B= is =C(R$^4$)— and —X=Y— is —S—N=, —N(R$^{10}$)—N=, or
=A-B= is —C(R$^4$)= and —X=Y— is =N—S—, or =N—N(R$^{10}$)—;

Z is

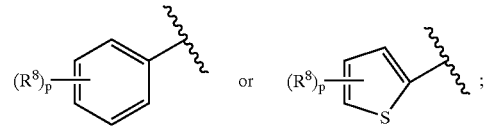

R$^1$ is H or —(C$_1$-C$_6$)alkyl;
R$^2$ is H, —(C$_1$-C$_6$)alkyl, —(C$_3$-C$_7$)cycloalkyl or —(C$_1$-C$_6$)alkyl(C$_3$-C$_7$)cycloalkyl;

R$^3$ is

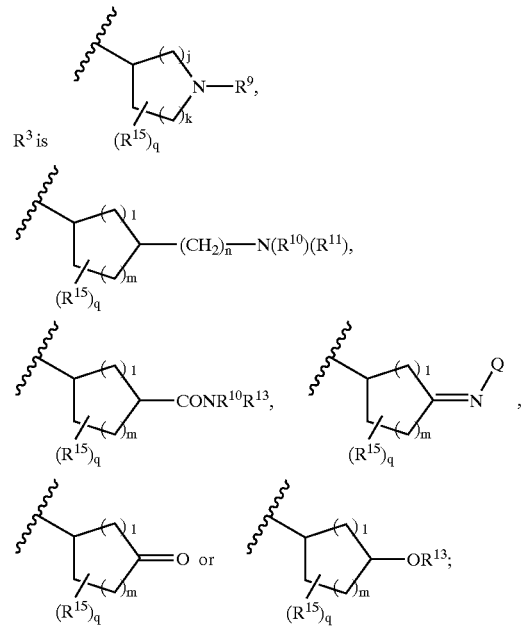

Q is —OR$^{13}$, or —NR$^{13}$R$^{14}$;
j is 1 or 2;
k is 0, 1 or 2;
l is 0, 1 or 2;
m is 0, 1 or 2;
n is 0 to 6;
p is 1, 2 or 3;
q is 1 or 2;
R$^4$, R$^5$, R$^6$ and R$^7$ may be the same or different, and are independently selected from H, —OH, halogen, haloalkyl, —(C$_1$-C$_6$)alkyl, —(C$_3$-C$_7$)cycloalkyl, —(C$_1$-C$_6$)alkyl(C$_3$-C$_7$)cycloalkyl, —CN, NR$^{10}$R$^{11}$, NR$^{13}$R$^{14}$, —O(C$_1$-C$_6$)alkyl, —O(C$_3$-C$_7$)cycloalkyl, —O(C$_1$-C$_6$)alkyl(C$_3$-C$_7$)cycolalkyl, —S(C$_1$-C$_6$)alkyl, —S(C$_3$-C$_7$)cycloalkyl and —S(C$_1$-C$_6$)alkyl(C$_3$-C$_7$)cycloalkyl;
R$^8$ may be the same or different, and is independently selected from H, halogen, —OH, haloalkyl, haloalkoxy, —CN, —NO$_2$, —(C$_1$-C$_6$)alkyl, —(C$_3$-C$_7$)cycloalkyl, —(C$_1$-C$_6$)alkyl(C$_3$-C$_7$)cycloalkyl, NR$^{10}$R$^{11}$, NR$^{13}$R$^{14}$, —O(C$_1$-C$_6$)alkyl, —O(C$_3$-C$_7$)cycloalkyl, —O(C$_1$-C$_6$)alkyl(C$_3$-C$_7$)cycloalkyl and —CONR$^{13}$R$^{14}$;

R$^9$ is —SO$_2$(C$_1$-C$_6$)alkyl, —SO$_2$(C$_3$-C$_7$)cycloalkyl, —SO$_2$(C$_1$-C$_6$)alkyl(C$_3$-C$_7$)cycloalkyl, —SO$_2$(C$_1$-C$_6$)haloalkyl, —SO$_2$[hydroxy(C$_2$-C$_6$)alkyl], —SO$_2$[amino(C$_2$-C$_6$)alkyl], —SO$_2$[alkoxy(C$_2$-C$_6$)alkyl], —SO$_2$[alkylamino(C$_2$-C$_6$)alkyl], —SO$_2$[dialkylamino(C$_2$-C$_6$)alkyl], —SO$_2$(aryl), —SO$_2$(heteroaryl), —SO$_2$[aryl(C$_1$-C$_6$)alkyl], —SO$_2$NR$^{13}$R$^{14}$, —CO(C$_1$-C$_6$)alkyl, —CO(C$_3$-C$_7$)cycloalkyl, —CO(C$_1$-C$_6$)alkyl(C$_3$-C$_7$)cycloalkyl, CO(C$_1$-C$_6$)haloalkyl, —C(O)aryl, —C(O)heteroaryl, —CONR$^{13}$R$^{14}$, —C(S)NR$^{13}$R$^{14}$, aryl, heteroaryl, —(CH$_2$)CONR$^{13}$R$^{14}$, —C(=NCN)alkylthio, —C(=NCN)NR$^{13}$R$^{14}$, —(C$_1$-C$_6$)alkyl, —(C$_3$-C$_7$)cycloalkyl, —(C$_1$-C$_6$)alkyl(C$_3$-C$_7$)cycloalkyl, —(C$_1$-C$_6$)alkylaryl, —(C$_1$-C$_6$)alkylheteroaryl or —COOR$^{12}$;

R$^{10}$ is H or alkyl;

R$^{11}$ is H, —(C$_1$-C$_6$)alkyl, —(C$_3$-C$_7$)cycloalkyl, —(C$_1$-C$_6$)alkyl(C$_3$-C$_7$)cycloalkyl, aryl, heteroaryl, —SO$_2$(C$_1$-C$_6$)alkyl, —SO$_2$(C$_3$-C$_7$)cycloalkyl, —SO$_2$(C$_1$-C$_6$)alkyl(C$_3$-C$_7$)cycloalkyl, —SO$_2$(C$_1$-C$_6$)haloalkyl, —SO$_2$(aryl), —SO$_2$(heteroaryl), —CO(C$_1$-C$_6$)alkyl, —CO(C$_3$-C$_7$)cycloalkyl, —CO(C$_1$-C$_6$)alkyl(C$_3$-C$_7$)cycloalkyl, —C(O)aryl, —C(O)heteroaryl, —CONR$^{13}$R$^{14}$ or —COOR$^{12}$;

R$^{12}$ is —(C$_1$-C$_6$)alkyl, —(C$_3$-C$_7$)cycloalkyl, —(C$_1$-C$_6$)alkyl(C$_3$-C$_7$)cycloalkyl, —(C$_1$-C$_6$)alkylaryl, —(C$_1$-C$_6$)alkylheteroaryl, aryl or heteroaryl;

R$^{13}$ and R$^{14}$ may be the same or different and are independently H, —(C$_1$-C$_6$)alkyl, —(C$_3$-C$_7$)cycloalkyl, —(C$_1$-C$_6$)alkyl(C$_3$-C$_7$)cycloalkyl, —(C$_1$-C$_6$)alkylaryl, aryl or heteroaryl; and, R$^{15}$ may be the same or different, and is H, —(C$_1$-C$_6$)alkyl, —(C$_3$-C$_7$)cycloalkyl, —(C$_1$-C$_6$)alkyl(C$_3$-C$_7$)cycloalkyl, aryl, heteroaryl, —CN, —CONR$^{13}$R$^{14}$, —COOR$^{13}$, —OH, —O(C$_1$-C$_6$)alkyl, —O(C$_3$-C$_7$)cycloalkyl, —O(C$_1$-C$_6$)alkyl(C$_3$-C$_7$)cycloalkyl, —NR$^{10}$R$^{11}$, —NR$^{13}$R$^{14}$, or a —(C$_1$-C$_6$)alkyl group substituted by an aryl, heteroaryl, hydroxy, alkoxy, —NR$^{10}$R$^{11}$, —NR$^{13}$R$^{14}$, —CONR$^{13}$R$^{14}$, or —COOR$^{13}$ group.

The invention also relates to pharmaceutical compositions containing the compounds of the invention, as well as methods of using the compounds alone or in combination with other therapeutic agents.

DETAILED DESCRIPTION OF THE INVENTION

The present invention relates to compounds of Formula I:

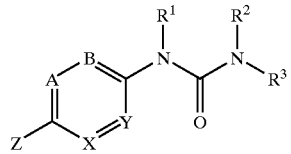

or a pharmaceutically acceptable salt and/or hydrate of said compound, or where applicable, a geometric or optical isomer or racemic mixture thereof, wherein =A-B= is =C(R$^4$)—C(R$^5$)= and —X=Y— is —C(R$^6$)=N—, —N=C(R$^7$)—, —N=N— or —S—, or =A-B= is =N—C(R$^5$)= and —X=Y— is —N=C(R$^7$)—, —C(R$^6$)=N—, —S— or —O—, or =A-B= is =C(R$^4$)—N= and —X=Y— is —C(R$^6$)=N—, —S— or —O—, or =A-B= is =N—N= and —X=Y— is —S— or —O—, or =A-B= is =C(R$^4$)— and —X=Y— is —S—N=, —N(R$^{10}$)—N=, or =A-B= is —C(R$^4$)= and —X=Y— is =N—S—, or =N—N(R$^{10}$)—;

Z is

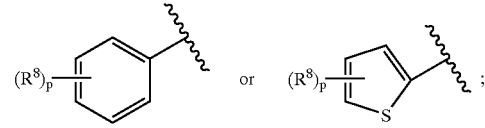

R$^1$ is H or —(C$_1$-C$_6$)alkyl;

R$^2$ is H, —(C$_1$-C$_6$)alkyl, —(C$_3$-C$_7$)cycloalkyl or —(C$_1$-C$_6$)alkyl(C$_3$-C$_7$)cycloalkyl;

R$^3$ is

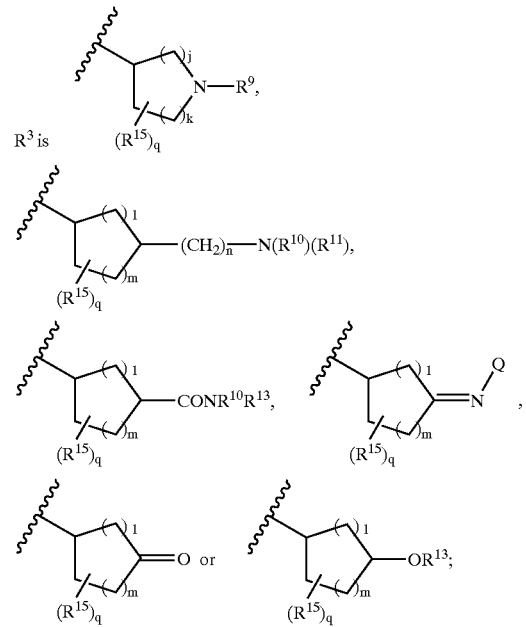

Q is —OR$^{13}$, or —NR$^{13}$R$^{14}$;

j is 1 or 2;

k is 0, 1 or 2;

l is 0, 1 or 2;

m is 0, 1 or 2;

n is 0 to 6;

p is 1, 2 or 3;

q is 1 or 2;

R$^4$, R$^5$, R$^6$ and R$^7$ may be the same or different, and are independently selected from H, —OH, halogen, haloalkyl, —(C$_1$-C$_6$)alkyl, —(C$_3$-C$_7$)cycloalkyl, —(C$_1$-C$_6$)alkyl(C$_3$-C$_7$)cycloalkyl, —CN, NR$^{10}$R$^{11}$, NR$^{13}$R$^{14}$, —O(C$_1$-C$_6$)alkyl, —O(C$_3$-C$_7$)cycloalkyl, —O(C$_1$-C$_6$)alkyl(C$_3$-C$_7$)cycolalkyl, —S(C$_1$-C$_6$)alkyl, —S(C$_3$-C$_7$)cycloalkyl and —S(C$_1$-C$_6$)alkyl(C$_3$-C$_7$)cycloalkyl;

R$^8$ may be the same or different, and is independently selected from H, halogen, —OH, haloalkyl, haloalkoxy, —CN, —NO$_2$, —(C$_1$–C$_6$)alkyl, —(C$_3$–C$_7$)cycloalkyl, —(C$_1$–C$_6$)alkyl(C$_3$–C$_7$)cycloalkyl, NR$^{10}$R$^{11}$, NR$^{13}$R$^{14}$, —O(C$_1$–C$_6$)alkyl, —O(C$_3$–C$_7$)cycloalkyl, —O(C$_1$–C$_6$)alkyl(C$_3$–C$_7$)cycloalkyl and —CONR$^{13}$R$^{14}$;

R$^9$ is —SO$_2$(C$_1$–C$_6$)alkyl, —SO$_2$(C$_3$–C$_7$)cycloalkyl, —SO$_2$(C$_1$–C$_6$)alkyl(C$_3$–C$_7$)cycloalkyl, —SO$_2$(C$_1$–C$_6$)haloalkyl, —SO$_2$[hydroxy(C$_2$–C$_6$)alkyl], —SO$_2$[amino(C$_2$–C$_6$)alkyl], —SO$_2$[alkoxy(C$_2$–C$_6$)alkyl], —SO$_2$[alkylamino(C$_2$–C$_6$)alkyl], —SO$_2$[dialkylamino(C$_2$–C$_6$)alkyl], —SO$_2$(aryl), —SO$_2$(heteroaryl), —SO$_2$[aryl(C$_1$–C$_6$)alkyl], —SO$_2$NR$^{13}$R$^{14}$, —CO(C$_1$–C$_6$)alkyl, —CO(C$_3$–C$_7$)cycloalkyl, —CO(C$_1$–C$_6$)alkyl(C$_3$–C$_7$)cycloalkyl, CO(C$_1$–C$_6$)haloalkyl, —C(O)aryl, —C(O)heteroaryl, —CONR$^{13}$R$^{14}$, —C(S)NR$^{13}$R$^{14}$, aryl, heteroaryl, —(CH$_2$)CONR$^{13}$R$^{14}$, —C(=NCN)alkylthio, —C(=NCN)NR$^{13}$R$^{14}$, —(C$_1$–C$_6$)alkyl, —(C$_3$–C$_7$)cycloalkyl, —(C$_1$–C$_6$)alkyl(C$_3$–C$_7$)cycloalkyl, —(C$_1$–C$_6$)alkylaryl, —(C$_1$–C$_6$)alkylheteroaryl or —COOR$^{12}$;

R$^{10}$ is H or alkyl;

R$^{11}$ is H, —(C$_1$–C$_6$)alkyl, —(C$_3$–C$_7$)cycloalkyl, —(C$_1$–C$_6$)alkyl(C$_3$–C$_7$)cycloalkyl, aryl, heteroaryl, —SO$_2$(C$_1$–C$_6$)alkyl, —SO$_2$(C$_3$–C$_7$)cycloalkyl, —SO$_2$(C$_1$–C$_6$)alkyl(C$_3$–C$_7$)cycloalkyl, —SO$_2$(C$_1$–C$_6$)haloalkyl, —SO$_2$(aryl), —SO$_2$(heteroaryl), —CO(C$_1$–C$_6$)alkyl, —CO(C$_3$–C$_7$)cycloalkyl, —CO(C$_1$–C$_6$)alkyl(C$_3$–C$_7$)cycloalkyl, —C(O)aryl, —C(O)heteroaryl, —CONR$^{13}$R$^{14}$ or —COOR$^{12}$;

R$^{12}$ is —(C$_1$–C$_6$)alkyl, —(C$_3$–C$_7$)cycloalkyl, —(C$_1$–C$_6$)alkyl(C$_3$–C$_7$)cycloalkyl, —(C$_1$–C$_6$)alkylaryl, —(C$_1$–C$_6$)alkylheteroaryl, aryl or heteroaryl;

R$^{13}$ and R$^{14}$ may be the same or different and are independently H, —(C$_1$–C$_6$)alkyl, —(C$_3$–C$_7$)cycloalkyl, —(C$_1$–C$_6$)alkyl(C$_3$–C$_7$)cycloalkyl, —(C$_1$–C$_6$)alkylaryl, aryl or heteroaryl; and, R$^{15}$ may be the same or different, and is H, —(C$_1$–C$_6$)alkyl, —(C$_3$–C$_7$)cycloalkyl, —(C$_1$–C$_6$)alkyl(C$_3$–C$_7$)cycloalkyl, aryl, heteroaryl, —CN, —CONR$^{13}$R$^{14}$, —COOR$^{13}$, —OH, —O(C$_1$–C$_6$)alkyl, —O(C$_3$–C$_7$)cycloalkyl, —O(C$_1$–C$_6$)alkyl(C$_3$–C$_7$)cycloalkyl, —NR$^{10}$R$^{11}$, —NR$^{13}$R$^{14}$, or a —(C$_1$–C$_6$)alkyl group substituted by an aryl, heteroaryl, hydroxy, alkoxy, —NR$^{10}$R$^{11}$, —NR$^{13}$R$^{14}$, —CONR$^{13}$R$^{14}$, or —COOR$^{13}$ group.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", etc.

"Patient" includes both human and other mammals.

"Mammal" means humans and other animals, including companion and food producing animals.

"Alkyl" means an aliphatic hydrocarbon group, which may be straight or branched and comprising 1 to 20 carbon atoms in the chain. Preferred alkyl groups contain 1 to 12 carbon atoms in the chain. More preferred alkyl groups contain 1 to 6 carbon atoms in the chain. Branched means that one or more lower alkyl groups such as methyl, ethyl or propyl, are attached to a linear alkyl chain.

"Lower alkyl" means a group having 1 to 6 carbon atoms in the chain, which may be straight or branched. The term "substituted alkyl" means that the alkyl group may be substituted by one or more substituents which may be the same or different, each substituent being independently selected from halo, alkyl, aryl, cycloalkyl, cyano, hydroxy, alkoxy, alkylthio, amino, —NH(alkyl), —NH(cycloalkyl), —N(alkyl)$_2$, carboxy and alkylOC(O)—. Non-limiting examples of suitable alkyl groups include methyl, ethyl, n-propyl, isopropyl, n-butyl, and t-butyl.

"Alkenyl" means an aliphatic hydrocarbon group containing at least one carbon-carbon double bond and which may be straight or branched and comprising 2 to 15 carbon atoms in the chain. Preferred alkenyl groups have 2 to 12 carbon atoms in the chain; and more preferably 2 to 6 carbon atoms in the chain. Branched means that one or more lower alkyl groups such as methyl, ethyl or propyl, are attached to a linear alkenyl chain. "Lower alkenyl" means 2 to 6 carbon atoms in the chain, which may be straight or branched. The term "substituted alkenyl" means that the alkenyl group may be substituted by one or more substituents which may be the same or different, each substituent being independently selected from halo, alkyl, aryl, cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group containing at least one carbon-carbon triple bond and which may be straight or branched and comprising 2 to 15 carbon atoms in the chain. Preferred alkynyl groups have 2 to 12 carbon atoms in the chain; and more preferably 2 to 4 carbon atoms in the chain. Branched means that one or more lower alkyl groups such as methyl, ethyl or propyl, are attached to a linear alkynyl chain. "Lower alkynyl" means 2 to 6 carbon atoms in the chain, which may be straight or branched. Non-limiting examples of suitable alkynyl groups include ethynyl, propynyl, and 2-butynyl. The term "substituted alkynyl" means that the alkynyl group may be substituted by one or more substituents which may be the same or different, each substituent being independently selected from alkyl, aryl and cycloalkyl.

"Aryl" means an aromatic monocyclic or multicyclic ring system comprising 6 to 14 carbon atoms, preferably 6 to 10 carbon atoms. The aryl group can be unsubstituted or optionally substituted on the ring with one or more substituents which may be the same or different, each being independently selected from alkyl, aryl, OCF$_3$, alkylOC(O)—, arylOC(O)—, CF$_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ may be the same or different each being independently selected from hydrogen, alkyl, aryl, and aralkyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted on the ring by replacing an available hydrogen on the ring by one or more substituents which may be the same or different, each being independently selected from alkyl, aryl, heteroaryl, aralkyl, alkylaryl, aralkenyl, heteroaralkyl, alkylheteroaryl, heteroaralkenyl, hydroxy, hydroxyalkyl, alkoxy, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different, each being independently selected from hydrogen, alkyl, aryl, and aralkyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenylethyl and naphthlenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include benzyl, o-tolyl, m-tolyl, p-tolyl and o-, p-, and m-xylyl. The bond to the parent moiety is through the aryl.

"Cycloalkyl" means a non-aromatic mono- or multicyclic ring system comprising 3 to 10 carbon atoms, preferably 5 to 10 carbon atoms. Preferred cycloalkyl rings contain 5 to 7 ring atoms. The cycloalkyl can be optionally substituted on the ring by replacing an available hydrogen on the ring by one or more substituents which may be the same or different, each being independently selected from alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from hydrogen, alkyl, aryl, and aralkyl. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above. The preferred halogen is fluoride. Specific examples, but non-limiting examples include a halo($C_1$–$C_6$)alkyl, —$CF_2CH_3$, —$CH_2F_3$ and —$CF_3$.

"Cycloalkenyl" means a non-aromatic mono or multicyclic ring system comprising 3 to 10 carbon atoms, preferably 5 to 10 carbon atoms which contains at least one carbon-carbon double bond. Preferred cycloalkenyl rings contain 5 to 7 ring atoms. The cycloalkenyl can be optionally substituted on the ring by replacing an available hydrogen on the ring by one or more substituents which may be the same or different, each being independently selected from alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from hydrogen, alkyl, aryl, and aralkyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising 3 to 10 ring atoms, preferably 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. The heterocyclenyl can be optionally substituted on the ring by replacing an available hydrogen on the ring by one or more substituents which may be the same or different, each being independently selected from alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from hydrogen, alkyl, aryl, and aralkyl. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2-dihydropyridyl, 1,4-dihydropyridyl, 1,2,3,6-tetrahydropyridyl and the like. Non-limiting examples of suitable oxaheterocyclenyl groups include 3,4-dihydro-2H-pyran, dihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom, respectively, is present as a ring atom. The heterocyclyl can be optionally substituted on the ring by replacing an available hydrogen on the ring by one or more substituents which may be the same or different, each being independently selected from alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from hydrogen, alkyl, aryl, and aralkyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl and the like.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of 5 to 6 ring atoms. The arylcycloalkyl can be optionally substituted on the ring by replacing an available hydrogen on the ring by one or more substituents which may be the same or different, each being independently selected from alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from hydrogen, alkyl, aryl, and aralkyl. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of 5 to 6 ring atoms and the cycloalkyl consists of 5 to 6 ring atoms. The prefix aza, oxa or thia before heteroaryl means that at least a nitrogen, oxygen or sulfur atom is present respectively as a ring atom. The heteroarylcycloalkyl can be optionally substituted on the ring by replacing an available hydrogen on the ring by one or more substituents which may be the same or different, each being independently selected from alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different each being independently selected from hydrogen, alkyl, aryl, and aralkyl. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 4,5,6,7-tetrahydro-1H-benzimidazolyl, and the like. The bond to the parent moiety is through a non-aromatic carbon atom.

"Cycloalkylheteroaryl" means a group derived from a fused heteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ group in which one or more of the hydrogen atoms on the nitrogen is replaced by an alkyl group as defined above. Additionally, "dialkylamino" means an —$NH_2$ group where two of the hydrogen atoms on the nitrogen have been replaced by an alkyl group, preferably a lower alkyl group.

"Arylamino" means an —$NH_2$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —$CH_3C(O)$—, $CH_3CH_2C(O)$— and the like.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylheteroaryl" means an -alkyl-heteroaryl group in which the alkyl and heteroaryl groups are previously described. The bond to the parent moiety is through the alkyl.

"Alkylsulfonyl" means an alkyl-$SO_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$SO_2$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

The term "mammal" as used herein, includes humans; companion animals such as dogs, cats, horses, monkeys and others; and food bearing animals such as cattle, cows, chickens and others.

As used herein, the term "composition" is intended to encompass a product comprising the specified ingredients in the specified amounts, as well as any product which results, directly or indirectly, from combination of the specified ingredients in the specified amounts.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

When a variable appears more than once in the structural formula, the identify of each variable appearing more than once maybe independently selected form the definition for that variable.

N-oxides can form on a tertiary nitrogen present in an R substituent, or on =N— in a heteroaryl ring substitutent and are included in the compounds of formula I.

The term "chemically stable compound" is defined as a compound that can be isolated, characterized, and tested for biological activity.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, either by separating isomers of a compound of formula I or by synthesizing individual isomers of a compound of formula I.

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

In a preferred group of compounds of Formula I, the heterocyclic group attached to

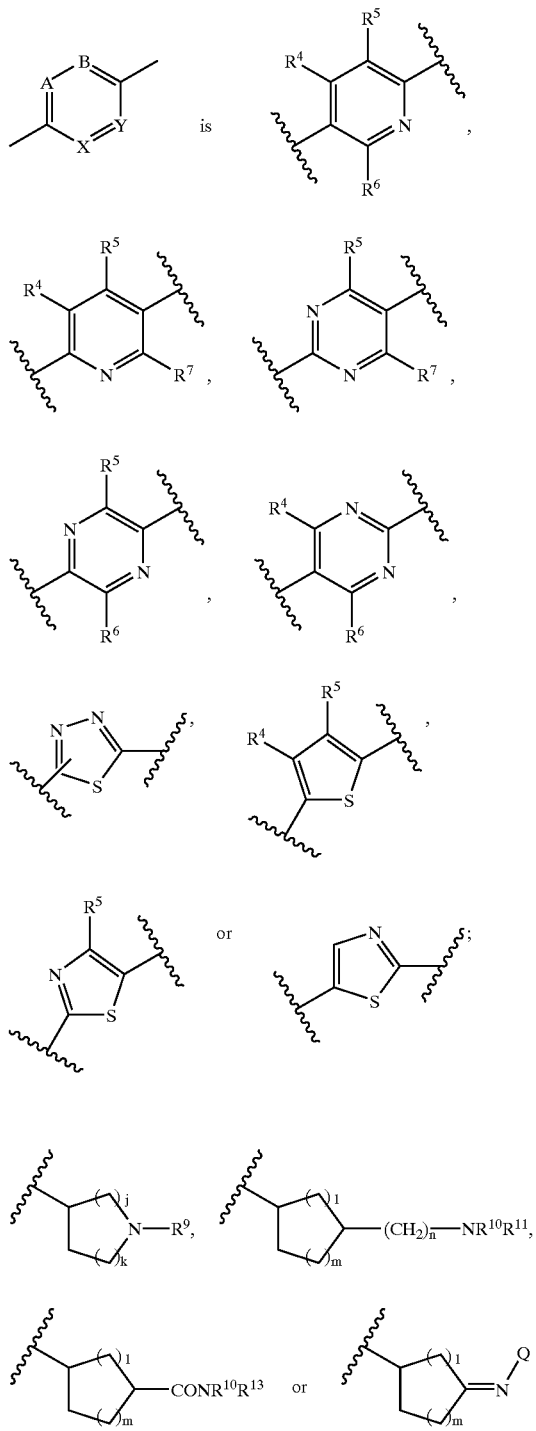

the sum of j and k is 2 or 3;
and the sum of l and m is 2 or 3.

In particular, the preferred group includes the above compounds wherein $R^1$ is hydrogen, $R^2$ is hydrogen or $(C_1-C_6)$alkyl, $R^4$, $R^5$, $R^6$ and $R^7$ are hydrogen or halogen, $R^8$ is independently selected from H, halogen, —O$(C_1-C_6)$ alkyl, —OH, haloalkyl and haloalkoxy, $R^9$ is —SO$_2(C_1-C_6)$ alkyl, —SO$_2(C_3-C_7)$cycloalkyl, —SO$_2(C_1-C_6)$alkyl$(C_3C_7)$ cycloalkyl, —SO$_2$aryl, —SO$_2$heteroaryl, —SO$_2$NR$^{13}$R$^{14}$, —CO$(C_1-C_6)$alkyl, —CO$(C_3-C_7)$cycloalkyl, —CO $(C_1-C_6)$alkyl$(C_3-C_7)$cycloalkyl, —C(O)aryl, —C(O) heteroaryl, aryl, heteroaryl, $R^{10}$ is H or —$(C_1-C_6)$alkyl, $R^{11}$ is —SO$_2(C_1-C_6)$alkyl, Q is —OR$^{13}$ or —NR$^{13}$R$^{14}$; $R^{13}$ and $R^{14}$ may be the same or different, and are independently H or —$(C_1-C_6)$alkyl; the sum of j and k is 2 or 3; the sum of l and m is 2 or 3; and n is 0 to 6.

Another aspect of this invention is a method of treating a patient having a disease or condition mediated by NPY by administering a therapeutically effective amount of a compound of Formula I or a pharmaceutically acceptable salt of said compound to the mammal. It is preferred that the receptor is the NPY-5 receptor.

Another aspect of this invention is directed to a method of treating obesity comprising administering to a patient in need of such treatment a therapeutically effective amount of a compound of Formula I or a pharmaceutically acceptable salt of said compound.

Another aspect of this invention is directed to a method for treating eating and metabolic disorders such as bulimia and anorexia comprising administering to a patient a therapeutically effective amount of a compound of Formula I or a pharmaceutically acceptable salt of said compound.

Another aspect of this invention is directed to a method for treating hyperlipidemia comprising administering to a patient a therapeutically effective amount of a compound of Formula I or a pharmaceutically acceptable salt of said compound.

Another aspect of this invention is directed to a method for treating cellulite and fat accumulation comprising administering to a patient a therapeutically effective amount of a compound of Formula I or a pharmaceutically acceptable salt of said compound.

Another aspect of this invention is directed to a method for treating type II diabetes comprising administering to a patient a therapeutically effective amount of a compound of Formula I or a pharmaceutically acceptable salt of said compound.

In addition to the "direct" effect of the compounds of this invention on the NPY5 subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

The compounds of the invention may also have utility in the treatment of central nervous system disorders such as seizures, depression, anxiety, alcoholism, pain; metabolic disorders such as hormone abnormalities; bone diseases such as osteoporosis, osteopenia, and Paget's disease; cardiovascular and renal disorders such hypertension, cardiac hypertrophy, vasospasm and nephropathy; sexual and reproductive disorders; gastrointestinal disorders such as Crohn's disease; and respiratory diseases such as asthma.

This invention is also directed to pharmaceutical compositions which comprise an amount of a compound of Formula I or a pharmaceutically acceptable salt of said compound and a pharmaceutically acceptable carrier therefor.

This invention is also directed to pharmaceutical compositions for the treatment of obesity which comprise an obesity treating amount of a compound of Formula, I r a pharmaceutically acceptable salt of said compound and a pharmaceutically acceptable carrier therefor.

Compounds of formula I may be produced by processes known to those skilled in the art as shown in the following reaction schemes and in the preparations and examples below.

Scheme 1

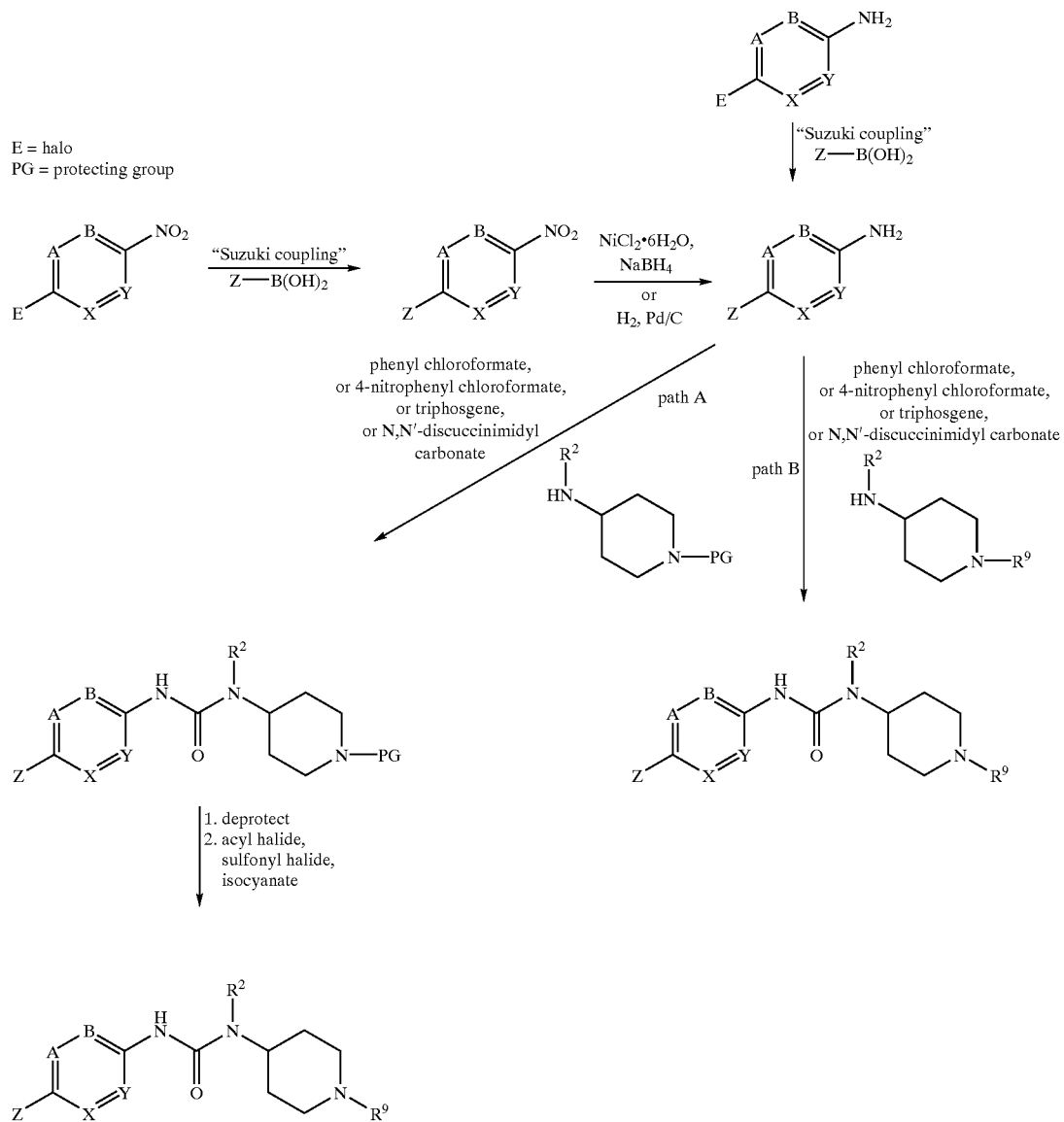

E = halo
PG = protecting group

In Scheme 1, a nitro heteroaryl halide is coupled to an aryl boronic acid to give a nitro-substituted biaryl derivative. Reduction of the nitro group gives a biaryl amine derivative. Alternatively, an amino heteroaryl halide derivative is coupled to an aryl boronic acid derivative to directly give an amino biaryl derivative. Treatment of the biaryl amine with a reagent such as phenyl chloroformate, 4-nitrophenyl chloroformate, triphosgene, or N,N'-disuccinimidyl carbonate and an organic base, followed by an amino substituted cyclic amine derivative with the ring nitrogen protected, gives a urea derivative (path A). Cleavage of the protecting group provides an amine that can be derivatized by treatment with, for example, acyl chlorides, sulfonyl chlorides, and isocyanates. Alternatively, in the urea-forming step an amino substituted cyclic amine derivative wherein the ring nitrogen is derivatized with an $R^9$ substituent can be used (path B). Path B is the preferred method when $R^9$ is aryl or heteroaryl. Compounds of Formula I where is

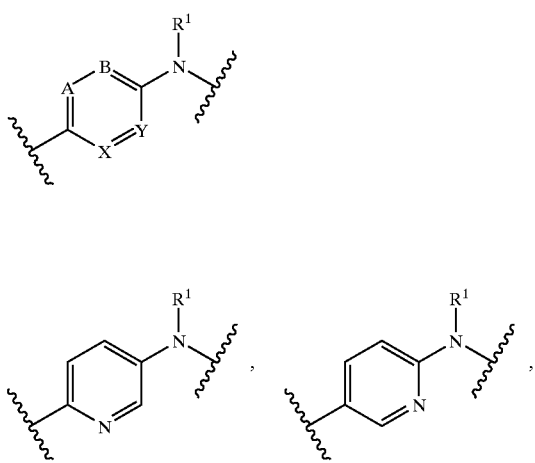

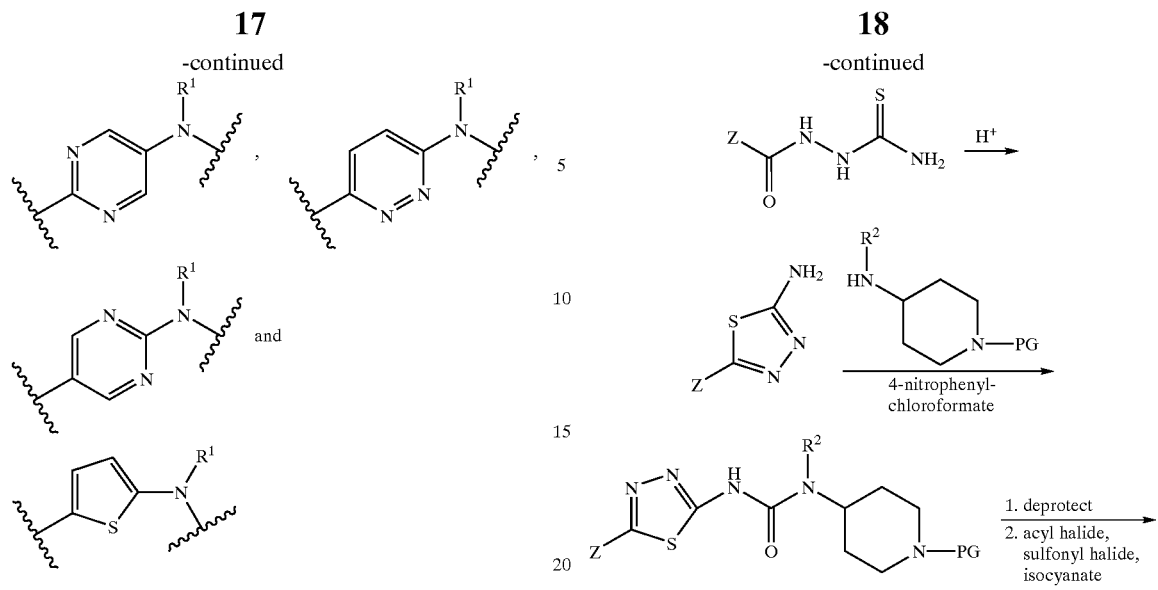

can be prepared by the methods outlined in Scheme 1.

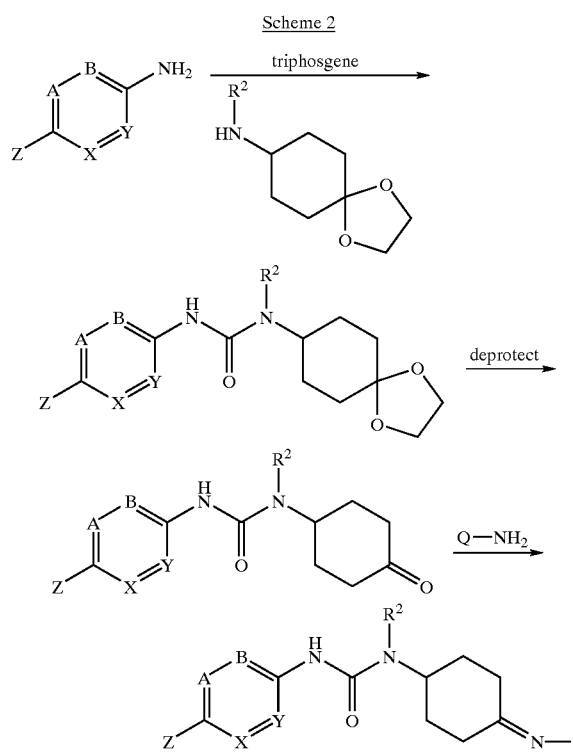

In Scheme 2, a biaryl amine derivative is treated with triphosgene and a base followed by treatment with 4-(methylamino)cyclohexanone ethylene ketal to give a urea derivative. Deprotection of the ketal, for example, by treatment with a strong acid, gives a ketone derivative. The ketone can then be derivatized by treatment with $QNH_2$.

Scheme 3

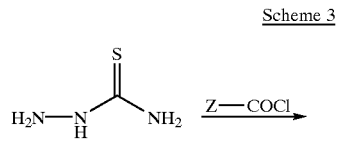

In Scheme 3, an acid chloride is condensed with thiosemicarbazide to give an N-acyl thiosemicarbazide derivative. Treatment of the N-acyl thiosemicarbazide with a strong acid results in the formation of an aminothiadiazole derivative. The aminothiadiazole is converted to a substituted urea derivative as described earlier.

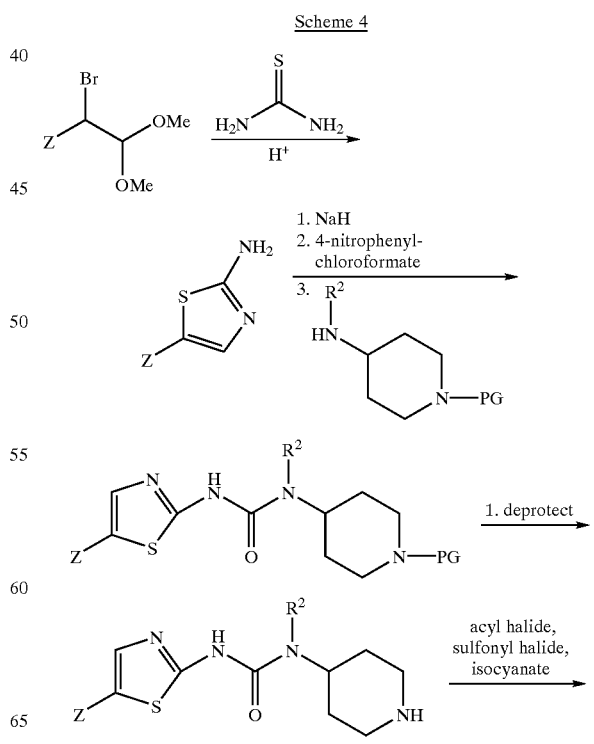

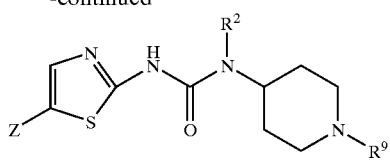

In Scheme 4 an alpha bromo acetal is condensed with thiourea to form a 5-substituted 2-aminothiazole derivative. The 2-aminothiazole derivative is converted to a substituted urea derivative as described in earlier schemes.

Scheme 5

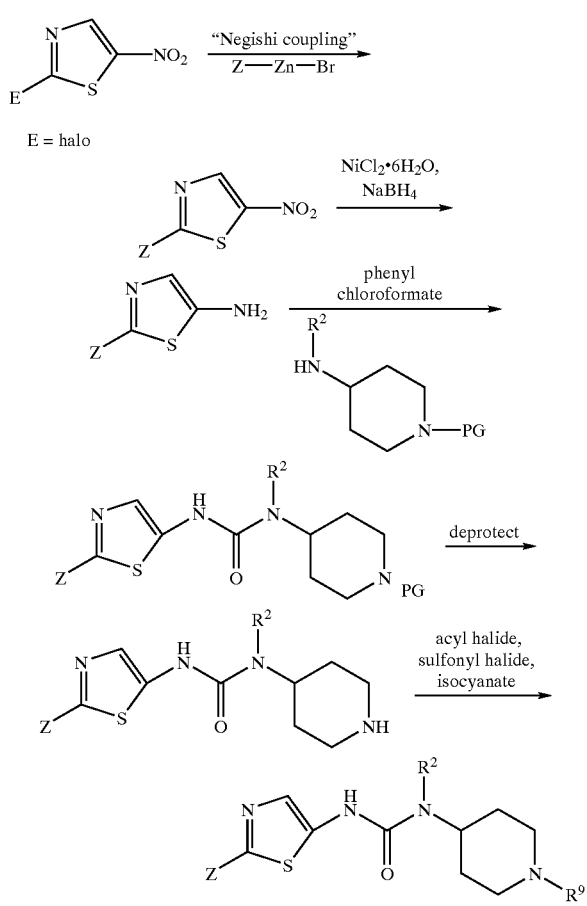

In Scheme 5, a 5-halo-2-nitrothiazole derivative is coupled to an arylzinc halide under palladium catalysis to give a 2-aryl-5-nitrothiazole derivative. The 5-nitrothiazole derivative is then converted to a substituted urea derivative as described in earlier Schemes.

The compounds of formula I exhibit selective neuropeptide Y Y5 receptor antagonizing activity, which has been correlated with pharmatcetucal activity for treating eating disorders, such as obesity and hyperphagia, and diabetes.

The compounds of formula I display pharmacological activity in test procedures designed to demonstrate neuropeptide Y Y5 receptor antagonist activity. The compounds are non-toxic at pharmaceutically therapeutic doses. Following are descriptions of the test procedures.

cAMP Assay

HEK-293 cells expressing the Y5 receptor subtype were maintained in Dulbecco's modified Eagles' media (Gico-BRL) supplemented with 10% FCS (ICN), 1% penicillin-streptomycin and 200 μg/ml Geneticin®(GibcoBRL #11811-031) under a humidified 5% $CO_2$ atmosphere. Two days prior to assay, cells were released from T-175 tissue culture flasks using cell dissociation solution (1×; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then preincubated with approximately 150 μl/well of assay buffer (HBSS supplemented with 4 mM $MgCl_2$, 10 mM HEPES, 0.2% BSA[HH]) containing 1 mM 3-isobutyl-1-methylxanthine ([IBMX] Sigma #I-587) with or without the antagonist compound of interest at 37° C. After 20 minutes the 1 mM IBMX-HH assay buffer (±antagonist compound) was removed and replaced with assay buffer containing 1.5 μM (CHO cells) or 5 μM (HEK-293 cells) forskolin (Sigma #F-6886) and various concentrations of NPY in the presence or absence of one concentration of the antagonist compound of interest. At the end of 10 minutes, the media were removed and the cell monolayers treated with 75 μl ethanol. The tissue culture plates were agitated on a platform shaker for 15 minutes, after which the plates were transferred to a warm bath in order to evaporate the ethanol. Upon bringing all wells to dryness, the cell residues were resolubilized with 250 1 FlashPlate® assay buffer. The amount of cAMP in each well was quantified using the [$^{125}$I]-cAMP FlashPlate® kit (NEN #SMP-001) and according to the protocol provided by the manufacturer. Data were expressed as either pmol cAMP/ml or as percent of control. All data points were determined in triplicate and $EC_{50}$'s (nM) were calculated using a nonlinear (sigmoidal) regression equation (GraphPad Prism™). The $K_B$ of the antagonist compound was estimated using the following formula:

$K_B=[B]/(1-\{[A']/[A]\})$ where [A] is the $EC_{50}$ of the agonist (NPY) in the absence of antagonist,

[A'] is the $EC_{50}$ of the agonist (NPY) in the presence of antagonist, and [B] is the concentration of the antagonist.

NPY Receptor Binding Assay

Human NPY Y5 receptors were expressed in CHO cells. Binding assays were performed in 50 mM HEPES, pH 7.2, 2.5 mM $CaCl_2$, 1 mM $MgCl_2$ and 0.1% BSA containing 5–10 μg of membrane protein and 0.1 nM $^{125}$L-peptide YY in a total volume of 200 μl. Non-specific binding was determined in the presence of 1 μM NPY. The reaction mixtures were incubated for 90 minutes at room temperature then filtered through Millipore MAFC glass fiber filter plates which had been pre-soaked in 0.5% polyethleneimine. The filters were washed with phosphate-buffered saline, and radioactivity was measured in a Packard TopCount scintillation counter.

For the compounds of this invention, a range of neuropeptide Y5 receptor binding activity from about 0.2 nM to about 500 nM was observed. Compounds of this invention preferably have a binding activity in the range of about 0.2 nM to 250 nM, more preferably about 0.2 to 100 nM, and most preferably about 0.2 to 10 nM.

Yet another aspect of this invention are combinations of a compound of Formula I or a pharmaceutically acceptable salt of said compound and other compounds as described below.

Accordingly, another aspect of this invention is a method for treating obesity comprising administering to a mammal (e.g., a female or male human)

a. an amount of a first compound, said first compound being a Formula I compound or a pharmaceutically acceptable salt of said compound; and b. an amount of a second compound, said second compound being an anti-obesity and/or anorectic agent such as a β$_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a first compound, said first compound being a Formula I compound or a pharmaceutically acceptable salt of said compound a second compound, said second compound being an anti-obesity and/or anorectic agent such as a β$_3$ agonist, a thyromimetic agent, an anoretic, or an NPY antagonist; and/or optionally a pharmaceutical carrier, vehicle or diluent.

Another aspect of this invention is a kit comprising:

a. an amount of a Formula I compound or a pharmaceutically acceptable salt of said compound and a pharmaceutically acceptable carrier, vehicle or diluent in a first unit dosage form;

b. an amount of an anti-obesity and/or anorectic agent such as a β$_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred anti-obesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a mammal (e.g., a female or male human)

a. an amount of a first compound, said first compound being a Formula I compound or a pharmaceutically acceptable salt of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a Formula I compound or a pharmaceutically acceptable salt of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a Formula I compound or a pharmaceutically acceptable salt of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

"Effective amount" or "therapeutically effective amount" is meant to describe an amount of compound of the present invention effective to treat a mammal (e.g., human) having a disease or condition mediated by MCH, and thus producing the desired therapeutic effect.

The effective amount of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The invention disclosed herein is exemplified by the following preparations and examples which should not be construed to limit the scope of the disclosure. Alternative mechanistic pathways and analogous structures may be apparent to those skilled in the art.

In the preparations and examples, the following abbreviations are used: room temperature (R.T.), phenyl (Ph), -t-butyloxycarbonyl (-Boc), methylamine (MeNH$_2$), sodium triacetoxyborohydride (NaBH(OAc)$_3$), ethyl acetate (EtOAc), methanol (MeOH), triethylamine (Et$_3$N), ether (Et$_2$O), tetrahydrofuran (THF), diisopropylethylamine (iPr$_2$NEt), 1,2 dimethoxyethane (DME), ethanol (EtOH), 1,1'-bis(diphenylphosphino)ferrocene (dppf) and preparative thin layer chromatography (PTLC), b (broad), bs (broad singlet).

Preparation 1

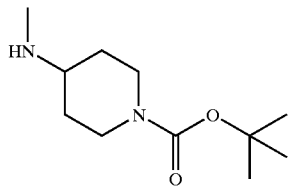

To a mixture of N-t-butoxycarbonyl-4-piperidone (10 g, 50 mmol) and aqueous methylamine (40% w/w, 10 ml) in 1,2-dichloroethane (125 ml) was added NaBH(OAc)$_3$ (16.0 g, 75 mmol). The reaction mixture was stirred overnight, then 1M NaOH (250 ml) was added and the whole was extracted with ether (700 ml). The organic layer was washed with sat'd NaCl, dried (MgSO$_4$), filtered, and concentrated to give the product (10.5 g, 97%) as an oil. $^1$H NMR (CDCl$_3$, 400 MHz) δ 4.09 (2H, m), 2.86 (2H, m), 2.55 (1H, m), 2.50 (3H, s), 1.90 (2H, m), 1.51 (9H, s), 1.30 (2H, m).

Preparation 2

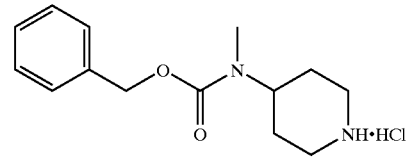

To a stirred solution of Preparation 1 (21.0 g, 83.7 mmol) and Et$_3$N (35 ml, 252 mmol) in CH$_2$Cl$_2$ (300 ml) was added benzyl chloroformate (18 ml, 126 mmol) dropwise. After 5 hr, sat'd NH$_4$Cl (200 ml) was added, and the organic layer was washed with H$_2$O (150 ml) and sat'd NaCl (150 ml), dried (MgSO$_4$), filtered and concentrated. To the residue (32 g) was added 4N HCl in 1,4-dioxane (300 ml), and the mixture was stirred for 4 hr. The reaction mixture was concentrated, acetone was added, and the reaction mixture was again concentrated. The solid residue was dissolved in MeOH (40 ml) and Et$_2$O was added. The resultant precipitate was collected, washed with Et$_2$O, and dried to give the product as a solid (20.2 g, 85%). MS m/e 249 (M+H$^+$, free base).

Preparation 3

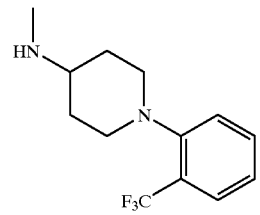

Step 1

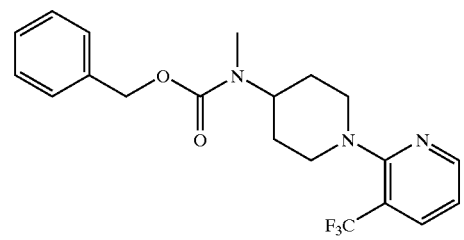

An N$_2$-purged mixture of Preparation 2 (1.03 g, 3.68 mmol), 2-bromo-3-trifluoromethylpyridine (1.60 g, 7.08 mmol), Pd(OAc)$_2$ (48 mg, 0.21 mmol), 1,3-bis-(diphenylphosphino)propane (0.82 g, 0.20 mmol), and sodium-t-butoxide (1.42 g, 14.8 mmol,) in toluene (10 ml) was heated at 100° C. for 3 hr. The reaction mixture was allowed to cool and filtered through celite. The filter pad was washed with CH$_2$Cl$_2$/water, and the organic layer was washed with sat'd NaCl, dried (MgSO$_4$), filtered and concentrated. The residue was subjected to flash chromatography (gradient; CH$_2$Cl$_2$ to 1:99 MeOH/CH$_2$Cl$_2$) to give the product (1.15 g, 80%). MS m/e 394 (M+H)$^+$.

Step 2

A mixture of the product of Step 1 (1.08 g, 2.75 mmol) in EtOH was stirred with 10% Pd/C (0.13 g) under an H$_2$ atmosphere. After one day, the catalyst was removed by filtration through Celite and the volatiles were evaporated to give the product (0.67 g, 94%). MS m/e 260 (M+H)$^+$.

The following compounds were made using essentially the same procedure and the appropriate starting materials:

Preparation 4

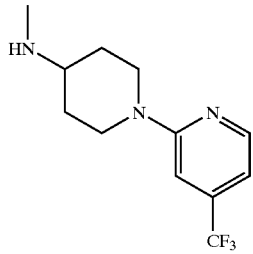

$^1$H NMR (CDCl$_3$, 400 MHz) δ 8.24 (1H, m), 6.8 (1H, s), 6.7 (1H, d), 4.3 (2H, m), 3.0 (2H, m), 2.7 (1H, m), 2.5 (3H, s), 2.0 (2H, m), 1.6 (1H, b), 1.4 (2H, m).

Preparation 5

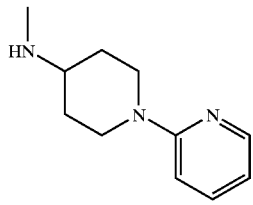

$^1$H NMR (CDCl$_3$, 400 MHz) δ 8.16 (1H, m), 7.43 (1H, m), 6.64 (1H, d, J=8.6 Hz), 6.56 (1H, m), 4.24 (2H, m), 2.90 (2H, m), 2.63 (1H, m), 2.47 (3H, s), 2.39 (1H, b), 2.00 (2H, m), 1.41 (1H, m). MS m/e 192 (M+H)$^+$.

Preparation 6

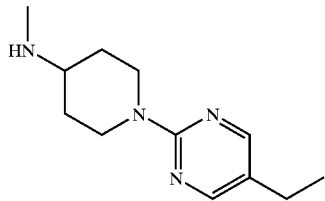

MS m/e 221 (M+H)$^+$.

Preparation 7

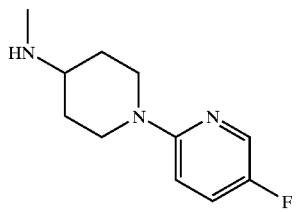

-continued

Step 1

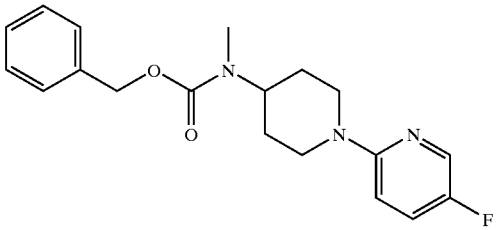

An N$_2$-purged mixture of Preparation 2 (0.94 g, 11 mmol), 2-chloro-5-fluoropyridine (0.94 g, 7.2 mmol; Synthesis, 1989, 905–908), Pd(OAc)$_2$ (64 mg, 0.29 mmol), (di-t-butylphosphino)biphenyl (0.16 mmol 49 mg), sodium-t-butoxide (22.2 mmol, 2.13 g) and toluene (40 ml) was heated at 100° C. for 3 hr. The reaction mixture was allowed to cool then filtered through celite, and the filter pad was washed with EtOAc. The combined filtrate and washings were washed with sat'd NaHCO$_3$, water and sat'd NaCl, then dried (MgSO$_4$), filtered and concentrated. The residue was subjected to flash chromatography (gradient; CH$_2$Cl$_2$ to 0.5:99.5 MeOH/CH$_2$Cl$_2$) to give the product (0.69 g, 28%). MS m/e 344 (M+H)$^+$.

Step 2

A mixture of the product of Step 1 (0.69 g, 2.0 mmol) and 10% Pd/C (80 mg) in EtOH (20 ml) was stirred under H$_2$ for 3 days. The reaction mixture was filtered through celite and the volatiles evaporated to yield the product (0.49 g, 100%) as a solid. $^1$H NMR (CDCl$_3$, 400 MHz) δ8.0 (1H, m), 7.2 (1H, m), 6.6 (1H, m), 4.2 (2H, m), 2.9 (2H, m), 2.6 (1H, m), 2.5 (3H, s), 2.0 (2H, m), 1.4 (2H, m).

The following compounds were prepared using the appropriate starting materials and essentially the same procedure.

Preparation 8

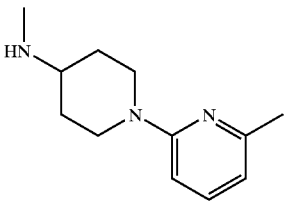

$^1$H NMR (CDCl$_3$, 400 MHz) δ 8.2 (1H, m), 7.35 (1H, m), 7.15 (1H, m), 4.25 (2H, m), 2.85 (2H, m), 2.65 (3H, s), 2.6 (1H, m), 2.5 (3H, s), 2.0 (2H, m), 1.9 (1H, b), 1.4 (2H, m).

Preparation 9

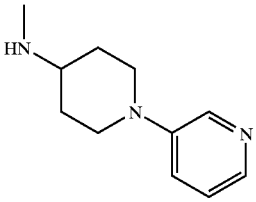

$^1$H NMR (CDCl$_3$, 400 MHz) δ 8.29 (1H, s), 8.07 (1H, b), 7.17 (2H, m), 4.2 (1H, b), 3.74 (2H, m), 2.82 (2H, m), 2.74 (3H, s), 1.70 (4H, m). MS m/e 192 (M+H)$^+$.

Preparation 10

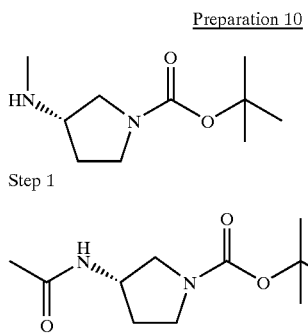

Step 1

A mixture of (3S)-(−)-3-acetamidopyrrolidine (3.04 g, 23.7 mmol), anhydrous CH$_2$Cl$_2$ (50 ml), di-tert-butyl dicarbonate (5.17 g, 23.7 mmol) and Et$_3$N (0.66 ml, 4.74 mmol) was stirred for 40 min., then partitioned between CH$_2$Cl$_2$ (200 ml) and H$_2$O. The organic layer was dried (Na$_2$SO$_4$), filtered and concentrated to give the product (5.17 g, 96%). $^1$HNMR (CDCl$_3$) δ 6.10–5.90 (d, b, 1H), 4.41 (m, 1H), 3.57 (s, b, 1H), 3.38 (m, b., 2H), 3.18 (m, b, 1H), 2.10 (m, 1H), 1.96 (s, 3H), 1.92 (s, b, 1H), 1.44 (s, 9H).

Step 2

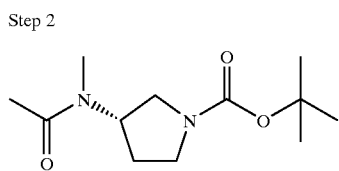

To a solution of the product of Step 1 (5.01 g, 21.9 mmol) in anhydrous THF (100 ml) was added NaH (95%, 0.665 g, 26.3 mmol) and CH$_3$I (4.1 ml, 66 mmol). The reaction mixture was stirred at R.T. for 16 hr. Additional NaH (60% in mineral oil, 0.263 g, 6.58 mmol) and CH$_3$I (4.1 ml, 65.8 mmol) were added. The reaction mixture was stirred for an additional 8 hr, quenched with CH$_3$OH (~5 ml) and poured into H$_2$O (100 ml). The whole was extracted with CH$_2$Cl$_2$ (3×200 ml) and the combined organic layers were dried (Na$_2$SO$_4$), filtered and evaporated. Subjection of the residue to flash chromatography (1:1 then 2:1 EtOAc/hexane, then 2:98 CH$_3$OH/CH$_2$Cl$_2$) gave the product (5.15 g, 97%). $^1$HNMR (CDCl$_3$) (mixture of rotamers) δ 5.10 (s, b., C-3H), 4.40 (s, b., C-3H), 3.60–3.00 (m, b., 4H), 2.89 (s) & 2.83 (s) (CH$_3$CO, 3H), 2.14 (s) & 2.09 (s) (CH$_3$N, 3H), 2.10–2.80 (m, b., 2H), 1.42 (d, 9H). MS m/e 243 (M+H)$^+$.

Step 3.

A mixture of the product of Step 2 (2.00 g, 8.26 mmol), CH$_3$OH (50 ml) and aq. 5N NaOH (6.7 ml) was refluxed for 2.5 days. The reaction mixture was allowed to cool then poured into H$_2$O (50 ml). The whole was extracted with CH$_2$Cl$_2$ (5×50 ml), and the combined organic layers were dried (Na$_2$SO$_4$), filtered and evaporated to give the product (1.40 g, 85%). $^1$HNMR (CDCl$_3$) δ 3.60–3.00 (m, 6H), 2.43 (s, 3H), 2.04 (m, 1H), 1.71 (m, 1H), 1.45 (d, 9H). MS m/e 201 (M+H)$^+$.

Preparation 11

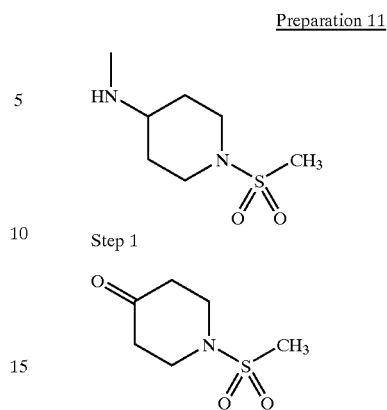

Step 1

To a stirred solution of 4-piperidone hydrate hydrochloride (40.00 g, 0.260 mol) in THF (320 ml) was added CH$_3$SO$_2$Cl (31.0 ml, 0.402 mol) and 15% aq. NaOH (156 ml) such that the reaction temperature was maintained between 26–32° C. After the addition was complete, the reaction was stirred at R.T. for 2 hr and transferred to a separatory funnel. The organic layer was collected and the aqueous layer was extracted with THF (2×250 ml). The combined organic layers were dried (Na$_2$SO$_4$). After filtration, the concentrated residue was washed with hexane to give the product (46.00 g, 100%) as a solid. $^1$H NMR (CDCl$_3$) δ 3.59 (t, J=6.00 Hz, 4H), 2.89 (s, 3H), 2.59 (t, J=5.6 Hz, 4H).

Step 2

A mixture of the product of Step 1 (40.00 g, 0.226 mol), CH$_3$CN (240 ml), and 40% CH$_3$NH$_2$ (20.4 ml, 0.263 mol) was stirred at R.T. for 1 hr. The mixture was slowly added to a −10° C. solution of NaBH(OAc)$_3$ (60.00 g, 0.283 mol) in CH$_3$CN (120 ml). After the addition was complete, the reaction was allowed to attain R.T. After 16 hr the reaction mixture was evaporated to a small volume, and 1N aq. NaOH (282 ml) was added. The resulting solution was extracted with CH$_2$Cl$_2$ (3×500 ml), then with toluene. The combined organic layers were dried (Na$_2$SO$_4$), filtered and evaporated to give the product (29.00 g, 63%) as a solid. $^1$H NMR (CDCl$_3$) δ 3.66 (m, 2H), 2.84 (m, 2H), 2.76 (s, 3H), 2.52 (m, 1H), 2.42 (s, 3H), 1.96 (m, 2H), 1.45 (m, 2H). MS m/e 193 (M+H)$^+$ Preparation 12

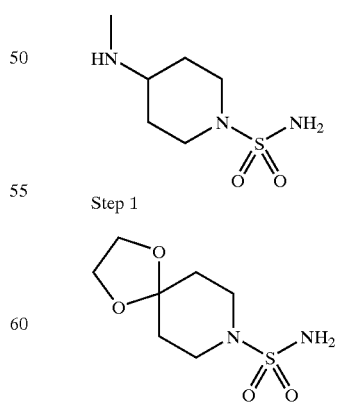

Step 1

A mixture of 4-piperidone ethylene ketal (0.64 ml, 5.0 mmol) and sulfamide (0.53 g, 5.5 mmol) in DME (20 ml) was refluxed for 16 hr. The mixture was concentrated to ca.

3 ml, dissolved in EtOAc (175 ml), washed with sat'd NH₄Cl (2×25 ml), water (2×25 ml), and brine (25 ml). The organic portion was dried, filtered, and evaporated to give the product (0.58 g, 52%). MS (ES) m/e 223 (M+H)⁺.

Step 2

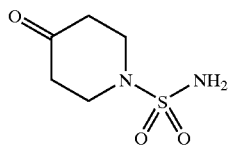

A mixture of the product of Step 1 (560 mg, 2.52 mmol) and pyridinium 4-toluenesulfonate (190 mg, 0.756 mmol) in acetone (25 ml) and water (0.5 ml) was refluxed for 64 hr. The mixture was evaporated to dryness and the residue was partitioned between CH₂Cl₂ (75 ml) and aq. NaHCO₃ (2×20 ml). The aqueous layer was extracted with CH₂Cl₂ and EtOAc sequentially. The EtOAc layer was evaporated to give the product (140 mg). ¹H NMR (CD₃OD, 400 MHz) δ 3.47 (1H, t, J=6.4 Hz), 3.15 (3H, m), 2.54 (1H, t, J=6.4 Hz), 1.81 (3H, m).

Step 3

A mixture of the product of Step 2 (135 mg, 0.757 mmol), 40% aqueous methylamine (0.3 ml, 2.4 mmol), and NaBH(OAc)₃ (375 mg, 1.77 mmol) in 1,2-dichloroethane (5 ml) was stirred at R.T. for 19 hr. The mixture was partitioned between 3N NaOH (5 ml) and EtOAc (3×50 ml). The organic layer was concentrated to give the crude product (40 mg). The aqueous layer was evaporated to dryness and the residue was suspended in EtOAc. The suspension was filtered and the filtrate concentrated to give another batch of the product (70 mg). MS (FAB) m/e 194 (M+H)⁺.

Preparation 13

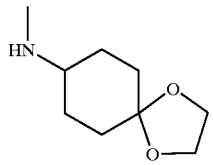

To a stirred mixture of 1,4-cyclohexanedione monoethylene ketal (4.68 g, 30 mmol) and 40% aq. methylamine (6.0 ml) in 1,2-dichloroethane (75 ml), was added NaBH(OAc)₃ (9.6 g, 45 mmol) in portions. The reaction mixture was vigorously stirred for 16 hr, then 1N NaOH (75 ml) was added. The organic layer was washed with sat'd NaCl, dried (MgSO₄), filtered, and evaporated to give an oil (4.60 g, 90%) that was used without further purification. ¹H NMR (CDCl₃, 400 MHz) δ 3.97 (4H, s), 2.47 (1H, m), 2.46 (3H, s), 1.91 (2H, m), 1.80 (2H, m), 1.59 (2H, m), 1.45 (2H, m).

EXAMPLE 1

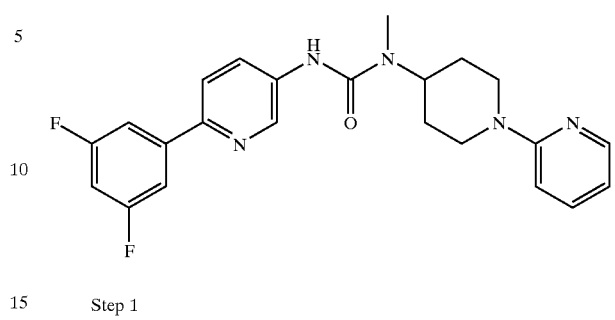

Step 1

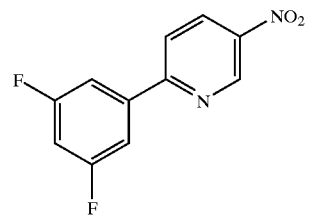

1-1

An N₂-purged mixture of 3,5-difluorophenylboronic acid (7.76 g, 24 mmol), 2-bromo-5-nitropyridine (2.46 g, 12 mmol), Pd(dppf)Cl₂·CH₂Cl₂ (0.40 g, 0.48 mmol), potassium phosphate (5.06 g, 23.9 mmol) and 1,2-dimethoxyethane (40 ml) was heated in a sealed tube at 80° C. for 5 hr. The reaction mixture was allowed to cool, filtered through celite, and the filtrate was concentrated. The residue was partitioned between sat'd Na₂CO₃ and EtOAc, and the organic layer was washed with water and sat'd NaCl, dried (MgSO₄), filtered and concentrated. Flash chromatography of the residue (1:99 EtOAc/hexane) to gave the product (2.16 g, 76%). MS m/e 237 (M+H)⁺.

Step 2

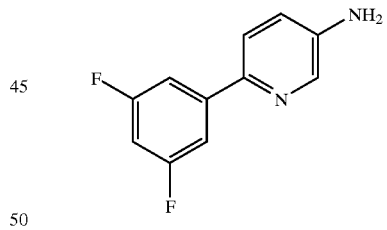

1-2

The product of Step 1 (240 mg, 1.0 mmol), 10% Pd/C (38 mg), and EtOH (25 ml) were stirred under an H₂ atmosphere for 3 days. The reaction mixture was filtered through celite and the volatiles were evaporated to give the product (171 mg, 83%). MS m/e 207 (M+H)⁺.

Step 3

A mixture of the product of Step 2 (145 mg, 0.70 mmol), triphosgene (70 mg, 0.24 mmol), and iPr₂NEt (0.61 ml, 3.5 mmol) in toluene (5 ml) was heated at 110° C. for 2 hr. The reaction mixture was allowed to cool and Preparation 5 (140 mg, 0.73 mmol) was added. After 16 hr, the reaction mixture was concentrated, and partitioned between CH₂Cl₂ (40 ml) and H₂O (20 ml). The organic layer was dried (MgSO₄), filtered and evaporated. The residue was subjected to PTLC (5:95 MeOH/CH₂Cl₂) to give the product (148 mg, 50%). ¹H NMR (CDCl₃, 400 MHz) δ 8.51 (1H, d, J=2.8 Hz), 8.18

(2H, m), 7.64 (1H, d, J=8.8 Hz), 7.50 (3H, m), 6.80 (1H, m), 6.70 (1H, d, J=8.8 Hz), 6.63 (1H, dd, J=7.1, 4.9 Hz), 6.54 (1H, s), 4.54 (1H, m), 4.45 (2H, m), 2.94 (2H, m), 2.93 (3H, s), 1.80–1.73 (4H, m). MS (m/e) 424 (M+H)$^+$.

EXAMPLE 2

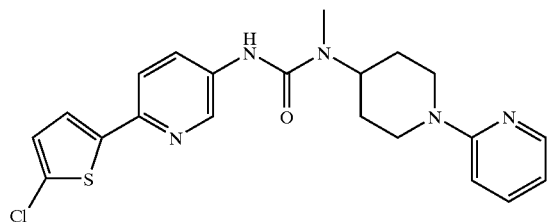

2

Step 1

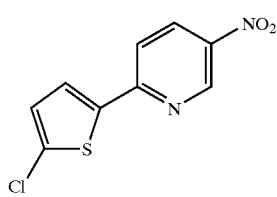

2-1

Reaction of 5-chlorothiophene-2-boronic acid with 2-chloro-5-nitropyridine by essentially the procedure of Example 1, Step 1 gave the product. MS m/e 241 (M+H)$^+$.

Step 2

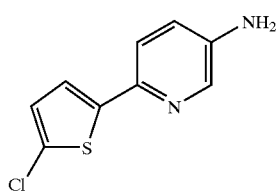

2-2

To an ice-cold suspension of the product of Step 1 (400 mg, 1.66 mmol) and NiCl$_2$.6H$_2$O (790 mg, 3.3 mmol) in MeOH (20 ml) was added NaBH$_4$ (252 mg, 6.67 mmol) in portions. After 20 min., H$_2$O (10 ml) and CH$_2$Cl$_2$ (20 ml) were added, and the whole was filtered through celite. The organic layer was dried (Na$_2$SO$_4$), filtered and concentrated to give a solid (286 mg, 82%). $^1$H NMR (CDCl$_3$, 400 MHz) δ 8.02 (1H, d, J=2.9 Hz), 7.38 (1H, d, J=8.4 Hz), 7.12 (1H, dd, J=3.8, 0.4 Hz), 6.98 (1H, dd, J=8.7, 2.7 Hz), 6.85 (1H, dd, J=3.8, 0.4 Hz), 3.76 (2H, b).

Step 3

To an ice-cold solution of the product of Step 2 (50 mg, 0.24 mmol) and pyridine (0.06 ml, 0.7 mmol) in THF (5 ml) was added N,N'-disuccinimidyl carbonate (60 mg, 0.24 mmol) and the reaction mixture was allowed to warm to R.T. After 1 hr, Preparation 5 (52 mg, 0.26 mmol) was added and the reaction mixture was stirred for 2 hr. The reaction mixture was poured into H$_2$O (20 ml) and extracted with CH$_2$Cl$_2$. The organic layer was dried (MgSO$_4$), filtered and evaporated. The residue was subjected to PTLC (5:95 MeOH/CH$_2$Cl$_2$) to give the product (84 mg, 82%). $^1$H NMR (CDCl$_3$, 400 MHz) δ 8.32 (1H, d, J=2.6 Hz), 8.16 (1H, m), 8.03 (1H, dd, J=8.6, 2.1 Hz), 7.46 (1H, d, J=8.6 Hz), 7.19 (1H, dd, J=4.0, 0.6 Hz), 6.91 (1H, s), 6.86 (1H, dd, J=8.7, 2.7 Hz), 6.85 (1H, dd, J=4.0, 0.6 Hz), 6.65 (1H, d, J=8.1 Hz), 6.60 (1H, m), 4.45 (1H, m), 4.38 (2H, m), 2.87 (2H, m), 2.84 (3H, s), 1.74–1.66 (4H, m).

EXAMPLE 3

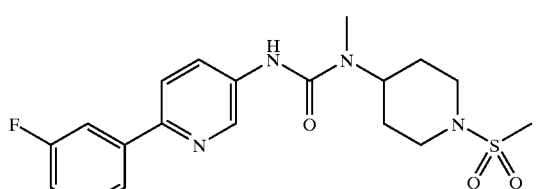

3

Step 1

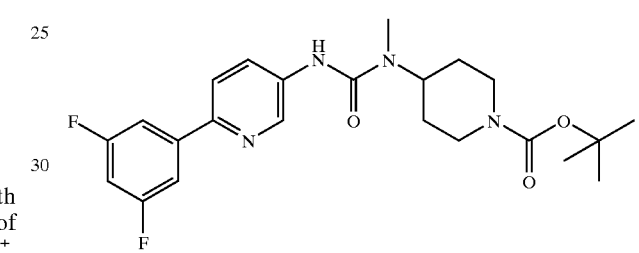

3-1

A mixture of the product from Example 1, Step 2 (1-2) (500 mg, 2.43 mmol), triphosgene (240 mg, 0.81 mmol) and iPr$_2$NEt (2.1 ml, 12 mmol) in toluene (15 ml) was heated at reflux for 2 hr. The reaction mixture was allowed to cool to R.T. and Preparation 1 (880 mg, 4.1 mmol) was added. The reaction mixture was stirred for 24 hr, diluted with CH$_2$Cl$_2$, and washed with sat'd NaHCO$_3$, H$_2$O, and sat'd NaCl. The organic layer was dried (Na$_2$SO$_4$), filtered and concentrated. Flash chromatography of the residue (gradient; CH$_2$Cl$_2$ to 1.5:98.5 MeOH/CH$_2$Cl$_2$) gave the product (650 mg, 60%). $^1$H NMR (CDCl$_3$) δ 8.49 (d, J=2.5 Hz, 1H), 8.12 (m, 1H), 7.60 (d, J=8.8 Hz, 1H), 7.46 (m, 2H), 6.78 (m, 1H), 6.74 (s, 1H), 4.40 (m, 1H), 4.20 (m, 2H), 2.90 (s, 3H), 2.78 (m, 2H), 1.67–1.55 (m, 4H), 1.45 (s, 9H). MS m/e 447 (M+H)$^+$.

Step 2

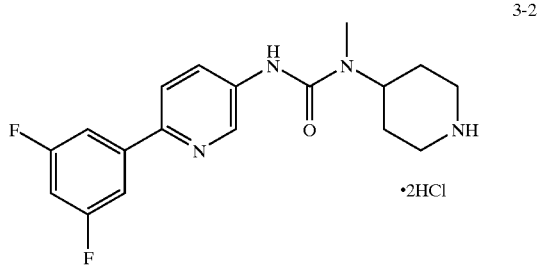

3-2

To a solution of the product of Step 1, 3-1, (510 mg, 1.14 mmol) in THF (15 ml) was added 2N HCl (10 ml). After 6 hr, the volatiles were evaporated and the residue was washed with ether (3×10 ml) to give the product (480 mg, 100%). $^1$H NMR (CD$_3$OD) δ 9.28 (s, 1H), 8.69 (d, J=8.8 Hz, 1H), 8.29 (d, J=8.6 Hz, 1H), 7.60 (d, J=5.8 Hz, 2H), 7.30 (t, 1H), 4.49 (m, 1H), 3.52 (d, 2H), 3.18 (t, 2H), 3.04 (s, 3H), 2.12 (m, 2H), 1.97 (m, 2H). MS m/e 347 (M+H)$^+$.

Step 3

To the product from Step 2 (0.19 mmol, 80 mg) in CH$_2$Cl$_2$ (2 ml) was added Et$_3$N (0.7 mmol, 0.1 ml) and methanesulfonyl chloride (0.44 mmol, 50 mg). The reaction was stirred at R.T. for 1 hr, concentrated, and the residue was subjected to PTLC (5:95 MeOH/CH$_2$Cl$_2$) to give the product (70 mg, 87%). 1H NMR (CDCl$_3$, 400 MHz) δ 8.50 (1H, d), 8.15 (1H, m), 7.7 (1H, d), 7.5 (2H, m), 6.8 (1H, m), 6.65 (1H, b), 4.5 (1H, m), 3.95 (2H, m), 3.0 (3H, s), 2.8 (5H, m), 1.8 (4H, m). MS m/e 425 (M+H)$^+$.

EXAMPLE 4

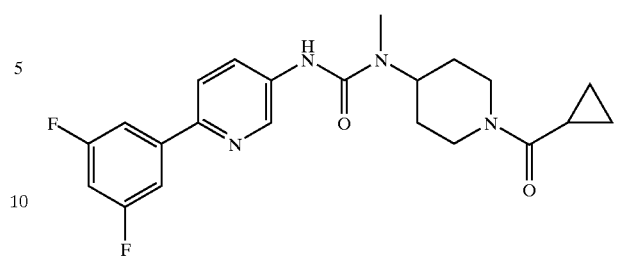

To a solution of the amine 3-2 (51 mg, 0.12 mmol) in CH$_2$Cl$_2$ (2 ml) was added Et$_3$N (0.1 ml, 0.7 mmol) and cyclopropylcarbonyl chloride (0.02 ml, 0.2 mmol). The reaction mixture was stirred at R.T. for 40 min. then subjected directly to PTLC (5:95 MeOH/CH$_2$Cl$_2$) to give the product (49 mg, 99%). $^1$H NMR (CDCl$_3$, 400 MHz) δ 8.50 (1H, m), 8.16 (1H, m), 7.65 (1H, m), 7.49 (2H, m), 6.82 (1H, m), 6.57 (1H, b), 4.75 (1H, m), 4.56 (1H, m), 4.32 (1H, b), 3.21 (1H, m), 2.93 (3H, s), 2.66 (1H, m), 1.80 (5H, m), 0.99 (2H, m), 0.77 (2H, m). MS m/e 415 (M+H)$^+$.

Using the appropriate reagents and Preparations the following Examples were prepared by essentially the same procedures:

| STRUCTURE | $^1$H NMR | MS (M + H)$^+$ |
|---|---|---|
| 1A | (CDCl$_3$) δ 8.52 (d, J = 2.5 Hz, 1H), 8.43 (m, 1H), 8.17 (m, 1H), 7.94 (m, 2H), 7.86 (m, 1H), 7.69 (d, J = 8.6 Hz, 1H), 7.45 (t, 2H), 7.39 (t, 1H), 7.01 (m, 1H), 6.60 (s, 1H), 4.47 (m, 1H), 3.68 (d, b, 2H), 3.04 (t, 2H), 2.98 (s, 3H), 1.87 (m, 2H), 1.78 (m, 2H). | 456 |
| 1B | (CDCl$_3$) δ 8.57 (d, J = 2.5 Hz, 1H), 8.30 (m, 1H), 8.18 (m, 1H), 7.93 (d, 2H), 7.70 (d, 1H), 7.43 (t, 2H), 7.39 (m, 1H), 6.82 (s, 1H), 6.77 (m, 1H), 6.58 (s, 1H), 4.59 (m, 1H), 4.48 (m, 2H), 3.01 (m, 2H), 2.96 (s, 3H), 1.83 (m, 2H), 1.70 (m, 2H). | 456 |
| 1C | (CDCl$_3$) δ 8.50 (d, J = 2.6 Hz, 1H), 8.17 (s, 2H), 8.14 (m, 1H), 7.94 (m, 2H), 7.68 (d, J = 8.8 Hz, 1H), 7.44 (t, 2H), 7.38 (m, 1H), 6.59 (s, 1H), 4.86 (m, 2H), 4.54 (m, 1H), 2.93 (m, 2H), 2.89 (s, 3H), 2.45 (q, 2H), 1.76 (m, 2H), 1.64 (m, 2H), 1.19 (t, 3H). | 417 |

-continued
| STRUCTURE | ¹H NMR | MS (M + H)⁺ |
|---|---|---|
| 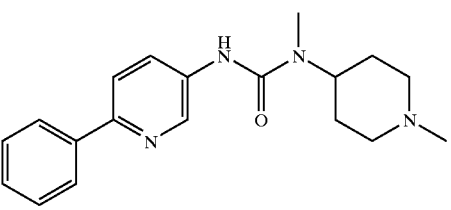
1D | (CDCl₃) δ 8.50 (d, J = 2.7 Hz, 1H), 8.10 (m, 1H), 7.91 (d, J = 7.3 Hz, 2H), 7.65 (d, J = 8.6 Hz, 1H), 7.43 (t, 2H), 7.37 (m, 1H), 6.63 (s, 1H), 4.24 (m, 1H), 2.94–2.90 (m, 5H), 2.28 (s, 3H), 2.05 (m, 2H), 1.82–1.64 (m, 4H). | 325 |
| 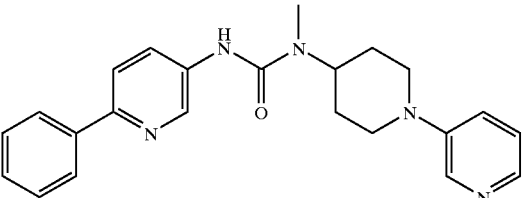
1E | (CDCl₃) δ 8.51 (d, J = 2.7 Hz, 1H), 8.32 (d, J = 1.8 Hz, 1H), 8.11 (m, 2H), 7.93 (d, J = 8.4 Hz, 2H), 7.64 (d, J = 8.8 Hz, 1H), 7.45 (t, 2H), 7.38 (m, 1H), 7.18 (m, 2H), 6.72 (s, 1H), 4.46 (m, 1H), 3.77 (m, 2H), 2.94 (s, 3H), 2.89 (m, 2H), 1.81 (m, 4H). | 388 |
| 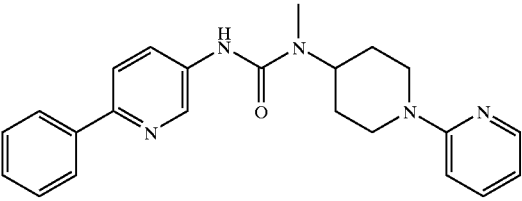
1F | (CDCl₃) δ 8.51 (d, J = 2.2 Hz, 1H), 8.19 (m, 1H), 8.15 (m, 1H), 7.95 (d, J = 8.4 Hz, 2H), 7.69 (d, J = 8.4 Hz, 1H), 7.50–7.37 (m, 4H), 6.70–6.56 (m, 3H), 4.53 (m, 1H), 4.43 (m, 2H), 2.98–2.90 (m, 5H), 1.78–1.71 (m, 4H). | 388 |
| 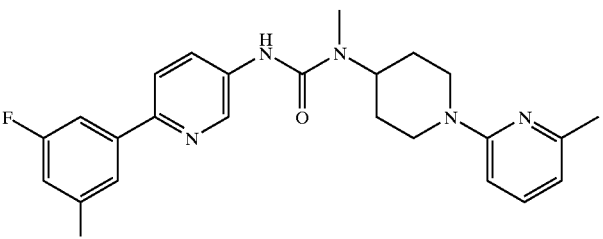
1G | (CDCl₃) δ 8.51 (m, 1H), 8.17 (m, 1H), 7.66 (d, 1H), 7.50 (m, 2H), 7.38 (t, 1H), 6.80 (m, 1H), 6.49 (m, 3H), 4.45 (m, 3H), 2.91 (m, 5H), 2.40 (s, 3H), 1.83–1.70 (m, 4H). | 438 |
| 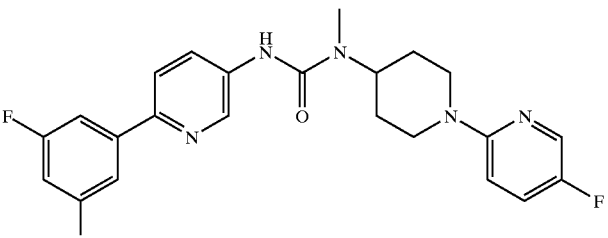
1H | (CDCl₃) δ 8.53 (m, 1H), 8.18 (m, 1H), 8.04 (d, 1H), 7.66 (d, 1H), 7.50 (m, 2H), 7.26 (m, 1H), 6.80 (m, 1H), 6.65 (m, 1H), 6.53 (s, 1H), 4.50 (m, 1H), 4.29 (m, 2H), 2.91 (m, 5H), 1.83–1.67 (m, 4H). | 442 |

| STRUCTURE | ¹H NMR | MS (M + H)⁺ |
|---|---|---|
| 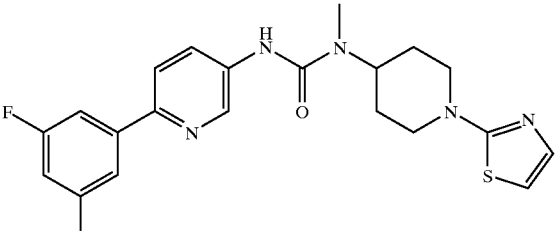<br>1I | (CDCl₃) δ 8.51 (m, 1H), 8.14 (m, 1H), 7.64 (m, 1H), 7.48 (m, 2H), 7.19 (m, 1H), 6.80 (m, 1H), 6.58 (m, 1H), 6.53 (s, 1H), 4.54 (m, 1H), 4.13 (m, 2H), 3.13 (m, 2H), 2.94 (s, 3H), 1.82 (m, 4H). | 430 |
| 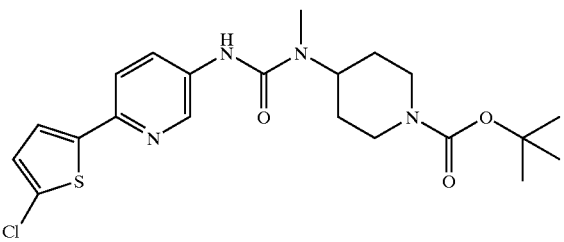<br>2A | (CDCl₃) δ 8.32 (d, J = 2.2 Hz, 1H), 8.08 (m, 1H), 7.50 (d, J = 8.7 Hz, 1H), 7.23 (d, J = 4.1 Hz, 1H), 6.88 (d, J = 4.0 Hz, 1H), 6.58 (s, 1H), 4.40 (m, 1H), 4.32 (m, 2H), 2.90 (s, 3H), 2.78 (m, 2H), 1.68–1.50 (m, 4H), 1.46 (s, 9H). | 451 |
| 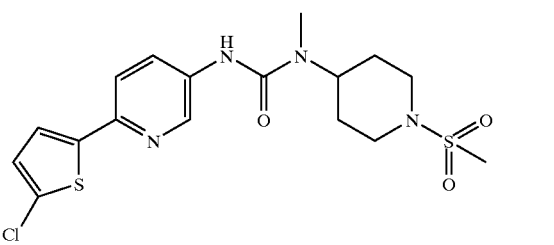<br>2B | (CDCl₃) δ 8.39 (d, J = 2.4 Hz, 1H), 8.07 (m, 1H), 7.52 (d, J = 8.8 Hz, 1H), 7.26 (m, 1H), 6.90 (d, J = 4.0 Hz, 1H), 6.60 (s, 1H), 4.42 (m, 1H), 3.92 (m, 2H), 2.94 (s, 3H), 2.80 (m, 5H), 1.84–1.79 (m, 4H). | 429 |
| 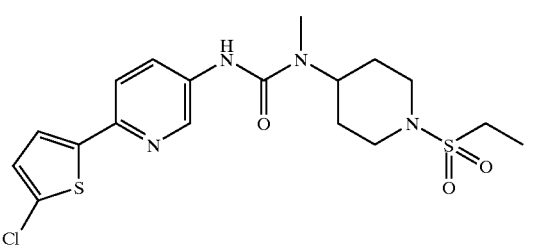<br>2C | (CDCl₃) δ 8.38 (s, 1H), 8.08 (m, 1H), 7.52 (d, J = 8.8 Hz, 1H), 7.27 (m, 1H), 6.90 (d, J = 3.8 Hz, 1H), 6.55 (bs, 1H), 4.45 (m, 1H), 3.92 (m, 2H), 2.94 (m, 7H), 1.84–1.76 (m, 4H), 1.37 (t, 3H). | 443 |
| 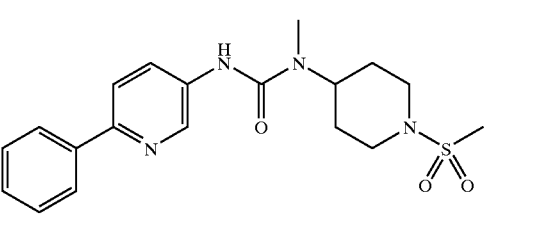<br>3A | (CDCl₃) δ 8.58 (s, b, 1H), 8.10 (m, 1H), 7.95 (m, 2H), 7.70 (m, 1H), 7.43 (t, 2H), 7.39 (m, 1H), 6.57 (s, b, 1H), 4.42 (m, 1H), 3.83 (m, 2H), 2.94 (s, 3H), 2.82 (m, 5H), 1.82 (m, 4H). | 389 |

-continued

| STRUCTURE | ¹H NMR | MS (M + H)⁺ |
|---|---|---|
| 3B | (CDCl₃) δ 8.60 (s, 1H), 8.15 (m, 1H), 7.93 (m, 2H), 7.70 (d, J = 8.8 Hz, 1H), 7.46 (t, 2H), 7.39 (m, 1H), 6.64 (s, b, 1H), 4.47 (m, 1H), 3.93 (m, 2H), 2.96 (m, 7H), 1.80 (m, 4H), 1.37 (t, 3H). | 403 |
| 3C | (CDCl₃) δ 8.52 (d, J = 2.6 Hz, 1H), 8.10 (m, 1H), 7.93 (m, 2H), 7.68 (d, J = 8.8 Hz, 1H), 7.49–7.35 (m, 3H), 6.58 (s, 1H), 4.46 (m, 1H), 3.95 (m, 2H), 3.18 (m, 1H), 3.03–2.85 (m, 5H), 1.76 (m, 4H), 1.33 (d, 6H). | 417 |
| 3D | (CDCl₃) δ 8.55 (d, J = 2.4 Hz, 1H), 8.10 (m, 1H), 7.93 (m, 2H), 7.68 (d, J = 8.8 Hz, 1H), 7.46–7.36 (m, 3H), 6.64 (s, 1H), 4.44 (m, 1H), 3.91 (m, 2H), 2.93–2.82 (m, 7H), 1.86–1.76 (m, 6H), 1.06 (t, 3H). | 417 |
| 3E | (CD₃OD) δ 9.20 (d, J = 2.4 Hz, 1H), 8.53 (m, 1H), 8.25 (d, J = 9.2 Hz, 1H), 7.58 (m, 2H), 7.29 (m, 1H), 4.30 (m, 1H), 3.86 (m, 2H), 3.00 (m, 5H), 2.50 (m, 1H), 1.95–1.78 (m, 4H), 1.05 (m, 4H). | 451 |
| 3F | (CDCl₃) δ 8.52 (d, J = 2.4 Hz, 1H), 8.12 (m, 1H), 7.63 (d, J = 8.8 Hz, 1H), 7.49 (m, 2H), 6.80 (m, 1H), 6.59 (s, 1H), 4.45 (m, 1H), 3.93 (m, 2H), 2.93 (m, 7H), 1.79 (m, 4H), 1.36 (t, 3H). | 439 |

| STRUCTURE | ¹H NMR | MS (M + H)⁺ |
|---|---|---|
| 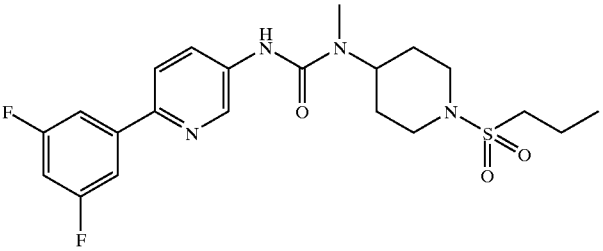<br>3G | (CD₃OD) δ 9.21 (d, J = 2.4 Hz, 1H), 8.55 (m, 1H), 8.25 (d, J = 9.2 Hz, 1H), 7.59 (m, 2H), 7.28 (m, 1H), 4.30 (m, 1H), 3.85 (m, 2H), 2.95 (m, 7H), 1.81 (m, 6H), 1.07 (t, 3H). | 453 |
| 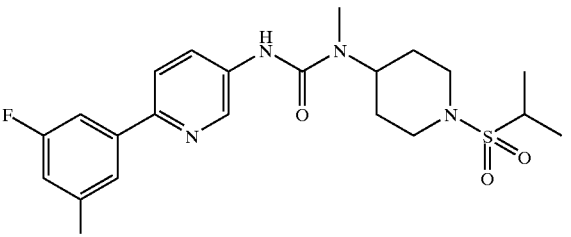<br>3H | (CDCl₃) δ 8.52 (d, J = 2.4 Hz, 1H), 8.13 (m, 1H), 7.63 (d, J = 8.8 Hz, 1H), 7.49 (m, 2H), 6.81 (m, 1H), 6.57 (s, 1H), 4.47 (m, 1H), 3.93 (m, 2H), 3.18 (m, 1H), 2.99 (m, 2H), 2.95 (s, 3H), 1.78 (m, 4H), 1.33 (d, 6H). | 453 |
| 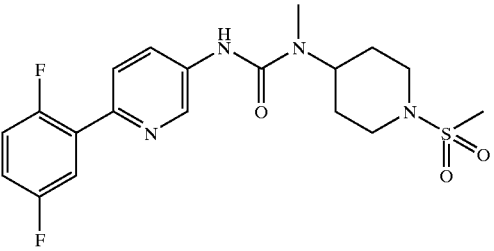<br>3I | (CDCl₃) δ 8.59 (d, J = 2.4 Hz, 1H), 8.07 (m, 1H), 7.78 (m, 1H), 7.71 (m, 1H), 7.28 (m, 2H), 6.53 (s, 1H), 4.44 (m, 1H), 3.91 (m, 2H), 2.96 (s, 3H), 2.79 (m, 5H), 1.82 (m, 4H). | 425 |
| 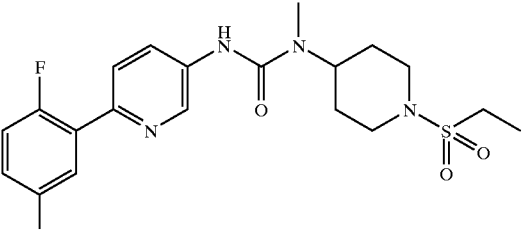<br>3J | (CDCl₃) δ 8.59 (d, J = 2.4 Hz, 1H), 8.06 (m, 1H), 7.78 (m, 1H), 7.71 (m, 1H), 7.07 (m, 1H), 7.02 (m, 1H), 6.54 (s, 1H), 4.46 (m, 1H), 3.93 (d, J = 11.2 Hz, 2H), 2.94 (m, 7H), 1.80 (m, 4H), 1.37 (t, 3H). | 439 |
| 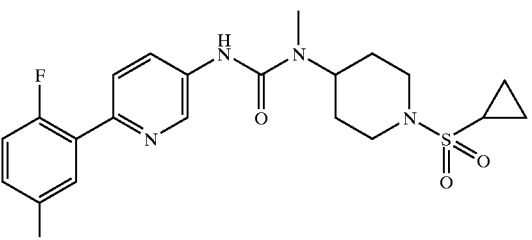<br>3K | (CDCl₃) δ 8.60 (s, 1H), 8.06 (m, 1H), 7.77 (d, J = 7.2 Hz, 1H), 7.68 (m, 1H), 7.07 (m, 1H), 7.01 (m, 1H), 6.66 (s, 1H), 4.43 (s, 1H), 3.90 (d, 2H), 2.91 (m, 5H), 2.60 (m, 1H), 1.78 (m, 4H), 1.15 (m, 2H), 1.00 (m, 2H). | 451 |

-continued

| STRUCTURE | ¹H NMR | MS (M + H)⁺ |
|---|---|---|
| 3L | (CDCl₃) δ 8.61 (s, 1H), 8.06 (m, 1H), 7.78 (d, J = 6.8 Hz, 1H), 7.71 (m, 1H), 7.07 (m, 1H), 7.01 (m, 1H), 6.64 (s, 1H), 4.44 (m, 1H), 3.91 (d, J = 12.4 Hz, 2H), 2.93 (s, 3H), 2.86 (m, 4H), 1.82 (m, 6H), 1.06 (t, 3H). | 453 |
| 3N | (CD₃OD) δ 9.20 (m, 1H), 8.55 (m, 1H), 8.25 (m, 1H), 7.71 (m, 3H), 7.41 (m, 1H), 4.29 (m, 1H), 3.85 (m, 2H), 3.01 (s, 3H), 2.87 (m, 5H), 1.94–1.76 (m, 4H). | 407 |
| 3O | (CDCl₃) δ 8.52 (d, J = 2.5 Hz, 1H), 8.12 (m, 1H), 7.71 (m, 3H), 7.38 (m, 1H), 7.07 (m, 1H), 6.47 (m, 1H), 4.43 (s, 1H), 3.92 (d, 2H), 2.96 (m, 5H), 2.28 (m, 1H), 1.81 (m, 4H), 1.17 (m, 2H), 1.00 (m, 2H). | 433 |
| 4A | (CDCl₃) δ 8.51 (d, J = 2.6 Hz, 1H), 8.13 (m, 1H), 7.93 (d, J = 7.3 Hz, 2H), 7.68 (d, J = 8.6 Hz, 1H), 7.45 (t, 2H), 7.38 (m, 1H), 6.61 (s, 1H), 4.42 (m, 1H), 4.20 (m, 2H), 2.91 (s, 3H), 2.79 (m, 2H), 1.76–1.55 (m, 4H), 1.45 (s, 9H). | 411 |
| 4B | (CDCl₃) δ 8.69 (d, J = 5.3 Hz, 2H), 8.55 (d, J = 2.7 Hz, 1H), 8.14 (m, 1H), 7.62 (d, J = 8.6 Hz, 1H), 7.47 (m, 2H), 7.28 (m, 2H), 6.95 (s, 1H), 6.79 (m, 1H), 4.82 (m, 1H), 4.56 (m, 1H), 3.68 (m, 1H), 3.17 (m, 1H), 2.94 (s, 3H), 2.85 (m, 1H), 1.90–1.45 (m, 4H). | 452 |

-continued
| STRUCTURE | ¹H NMR | MS (M + H)⁺ |
|---|---|---|
| 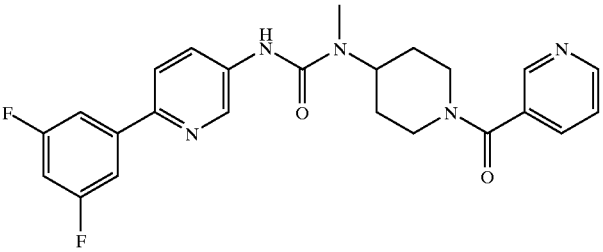<br>4C | (CDCl₃) δ 8.68 (m, 2H), 8.55 (m, 1H), 8.12 (m, 1H), 7.78 (m, 1H), 7.64 (d, J = 8.6 Hz, 1H), 7.47 (m, 2H), 7.37 (m, 1H), 6.82 (m, 1H), 6.65 (s, 1H), 4.86 (m, 1H), 4.59 (m, 1H), 3.82 (m, 1H), 3.22 (m, 1H), 2.96 (s, 3H), 2.85 (m, 1H), 1.90–1.45 (m, 4H). | 452 |
| 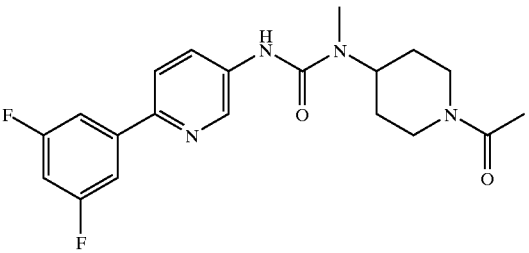<br>4D | (CDCl₃) δ 8.50 (d, J = 2.8 Hz, 1H), 8.12 (d, J = 8.8 Hz, 1H), 7.62 (d, J = 8.8 Hz, 1H), 7.45 (m, 2H), 6.80 (m, 2H), 4.75 (m, 1H), 4.50 (m, 1H), 3.90 (m, 1H), 3.18 (m, 1H), 2.90 (s, 3H), 2.59 (m, 1H), 2.11 (s, 3H), 1.80–1.56 (m, 4H). | 389 |
| 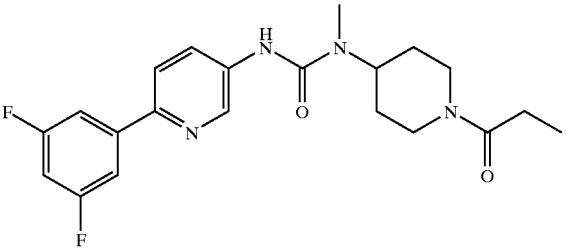<br>4E | (CDCl₃) δ 8.50 (d, J = 2.0 Hz, 1H), 8.13 (m, 1H), 7.62 (d, J = 8.8 Hz, 1H), 7.46 (m, 2H), 6.78 (m, 2H), 4.76 (m, 1H), 4.51 (m, 1H), 3.92 (m, 1H), 3.11 (m, 1H), 2.90 (s, 3H), 2.59 (m, 1H), 2.35 (q, 2H), 1.76–1.54 (m, 4H), 1.15 (m, 3H). | 403 |
| 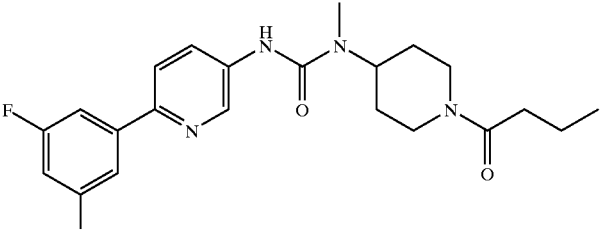<br>4F | (CD₃OD) δ 9.26 (d, J = 2.4 Hz, 1H), 8.59 (m, 1H), 8.29 (d, J = 8.8 Hz, 1H), 7.60 (m, 2H), 7.32 (m, 1H), 4.70 (m, 1H), 4.39 (m, 1H), 4.10 (m, 1H), 3.21 (m, 1H), 2.98 (s, 3H), 2.71 (m, 1H), 2.42 (m, 2H), 1.79–1.62 (m, 6H), 0.99 (m, 3H). | 417 |
| 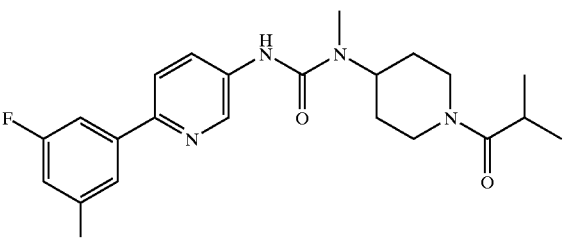<br>4G | (CDCl₃) δ 8.50 (d, J = 2.4 Hz, 1H), 8.15 (m, 1H), 7.61 (d, J = 8.4 Hz, 1H), 7.47 (m, 2H), 6.87 (s, 1H), 6.78 (m, 1H), 4.76 (m, 1H), 4.50 (m, 1H), 4.05 (m, 1H), 3.11 (m, 1H), 2.90 (s, 3H), 2.80 (m, 1H), 2.59 (m, 1H), 1.82–1.54 (m, 4H), 1.13 (m, 6H). | 417 |

-continued

| STRUCTURE | ¹H NMR | MS (M + H)⁺ |
|---|---|---|
| 4H | (CDCl₃) δ 8.50 (d, J = 2.4 Hz, 1H), 8.14 (m, 1H), 7.66 (d, J = 6.4 Hz, 1H), 7.49 (m, 2H), 6.81 (m, 1H), 6.49 (s, 1H), 4.76 (m, 2H), 4.12 (m, 1H), 3.25 (m, 1H), 2.95 (s, 3H), 2.86 (m, 1H), 1.89–1.60 (m, 4H). | 443 |
| 4I | (CDCl₃) δ 8.50 (d, J = 2.0 Hz, 1H), 8.13 (m, 1H), 7.62 (d, J = 8.4 Hz, 1H), 7.46 (m, 2H), 6.80 (m, 2H), 4.70 (m, 1H), 4.52 (m, 1H), 4.10 (q, 2H), 3.94 (m, 1H), 3.42 (s, 3H), 3.10 (m, 1H), 2.90 (s, 3H), 2.64 (m, 1H), 1.79–1.57 (m, 4H). | 419 |
| 4J | (CDCl₃) δ 8.50 (d, J = 2.4 Hz, 1H), 8.12 (m, 1H), 7.64 (d, J = 8.8 Hz, 1H), 7.47 (m, 2H), 6.80 (m, 1H), 6.67 (s, 1H), 4.79 (m, 1H), 4.56 (m, 1H), 3.86 (m, 1H), 3.24 (m, 3H), 2.96 (s, 3H), 2.67 (m, 1H), 1.85–1.59 (m, 4H). | 457 |
| 4K | (CDCl₃) δ 8.50 (d, J = 2.4 Hz, 1H), 8.15 (m, 1H), 7.63 (d, J = 8.8 Hz, 1H), 7.46 (m, 3H), 7.30 (d, 1H), 7.03 (m, 1H), 6.80 (m, 2H), 4.59 (m, 3H), 3.06 (m, 2H), 2.93 (s, 3H), 1.81–1.64 (m, 4H). | 457 |
| 4L | (CDCl₃) δ 8.49 (d, J = 2.0 Hz, 1H), 8.15 (m, 1H), 7.62 (d, J = 8.8 Hz, 1H), 7.47 (m, 2H), 6.80 (m, 1H), 6.69 (s, 1H), 4.42 (m, 1H), 3.77 (m, 2H), 2.92–2.83 (m, 11H), 1.68 (m, 4H). | 418 |

| STRUCTURE | ¹H NMR | MS (M + H)⁺ |
|---|---|---|
| 4M | (CDCl₃) δ 8.50 (d, J = 2.4 Hz, 1H), 8.14 (m, 1H), 7.61 (d, J = 8.0 Hz, 1H), 7.45 (m, 2H), 6.80 (m, 2H), 4.40 (m, 1H), 3.72 (m, 2H), 3.20 (m, 4H), 2.90 (s, 3H), 2.84 (m, 2H), 1.70 (m, 4H), 1.11 (m, 6H). | 446 |
| 4N | (CDCl₃) δ 8.50 (d, J = 2.4 Hz, 1H), 8.15 (m, 1H), 7.62 (d, J = 8.8 Hz, 1H), 7.45 (m, 2H), 6.79 (m, 2H), 4.76 (m, 1H), 4.50 (m, 1H), 3.78 (m, 1H), 3.26 (m, 1H), 3.04 (m, 1H), 2.90 (s, 3H), 2.60 (m, 1H), 2.35–2.13 (m, 4H), 1.99–1.42 (m, 6H). | 429 |
| 4O | (CDCl₃) δ 8.50 (d, J = 2.8 Hz, 1H), 8.15 (m, 1H), 7.64 (d, J = 8.8 Hz, 1H), 7.49 (m, 2H), 6.80 (m, 1H), 6.54 (s, 1H), 4.80 (m, 1H), 4.54 (m, 1H), 4.06 (m, 1H), 3.13 (m, 1H), 2.90 (m, 4H), 2.61 (m, 1H), 1.82–1.55 (m, 12H). | 443 |
| 4P | (CDCl₃) δ 8.50 (d, J = 2.8 Hz, 1H), 8.15 (m, 1H), 7.63 (d, J = 8.8 Hz, 1H), 7.46 (m, 2H), 6.79 (m, 2H), 4.74 (m, 1H), 4.52 (m, 1H), 4.00 (m, 1H), 3.11 (m, 1H), 2.91 (s, 3H), 2.52 (m, 2H), 1.79–1.24 (m, 14H). | 457 |
| 4Q | (CDCl₃) δ 8.50 (m, 1H), 8.15 (m, 1H), 7.64 (d, J = 8.8 Hz, 1H), 7.49 (m, 3H), 7.33–7.19 (m, 2H), 6.80 (m, 1H), 6.50 (s, 1H), 4.91 (m, 1H), 4.58 (m, 1H), 3.50 (m, 1H), 3.21 (m, 1H), 2.94 (s, 3H), 2.86 (m, 1H), 1.87–1.67 (m, 4H). | 519 |

| STRUCTURE | ¹H NMR | MS (M + H)⁺ |
|---|---|---|
| 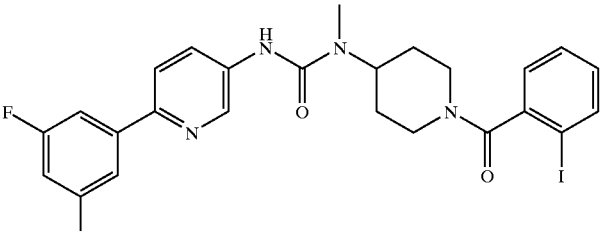<br>4R | (CDCl₃) δ 8.50 (m, 1H), 8.15 (m, 1H), 7.83 (m, 1H), 7.65 (d, J = 8.8 Hz, 1H), 7.50 (m, 2H), 7.41 (m, 1H), 7.24 (m, 1H), 7.10 (m, 1H), 6.80 (m, 1H), 6.48 (s, 1H), 4.92 (m, 1H), 4.60 (m, 1H), 3.50 (m, 1H), 3.21 (m, 1H), 2.96 (s, 3H), 2.85 (m, 1H), 1.98–1.50 (m, 4H). | 577 |
| 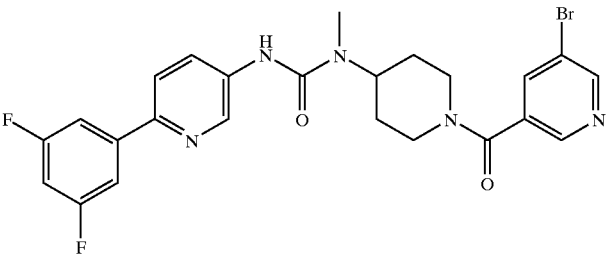<br>4S | (CDCl₃) δ 8.74 (d, J = 2.4 Hz, 1H), 8.58 (m, 1H), 8.50 (d, J = 2.0 Hz, 1H), 8.15 (m, 1H), 7.92 (m, 1H), 7.66 (d, J = 8.4 Hz, 1H), 7.50 (m, 2H), 6.80 (m, 1H), 6.50 (s, 1H), 4.86 (m, 1H), 4.62 (m, 1H), 3.80 (m, 1H), 3.21 (m, 1H), 2.97 (s, 3H), 2.88 (m, 1H), 1.94–1.70 (m, 4H). | 530<br>532 |
| 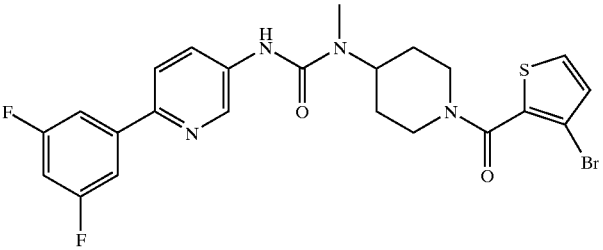<br>4T | (CDCl₃) δ 8.50 (d, J = 2.4 Hz, 1H), 8.14 (m, 1H), 7.64 (d, J = 8.8 Hz, 1H), 7.50 (m, 2H), 7.35 (d, 1H), 6.99 (d, 1H), 6.80 (m, 1H), 6.60 (s, 1H), 4.80 (m, 1H), 4.60 (m, 1H), 3.80 (m, 1H), 3.21 (m, 2H), 2.94 (s, 3H), 1.77 (m, 4H). | 535<br>537 |
| 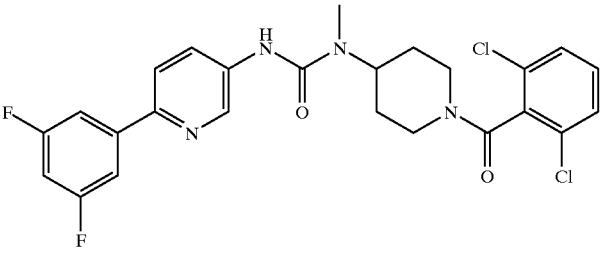<br>4U | (CDCl₃) δ 8.51 (m, 1H), 8.10 (m, 1H), 7.62 (d, J = 8.4 Hz, 1H), 7.47 (m, 2H), 7.33 (m, 2H), 7.25 (m, 1H), 6.84 (s, 1H), 6.77 (m, 1H), 4.92 (m, 1H), 4.56 (m, 1H), 3.41 (m, 1H), 3.20 (m, 1H), 2.90 (s, 3H), 2.87 (m, 1H), 1.83–1.67 (m, 4H). | 519 |
| 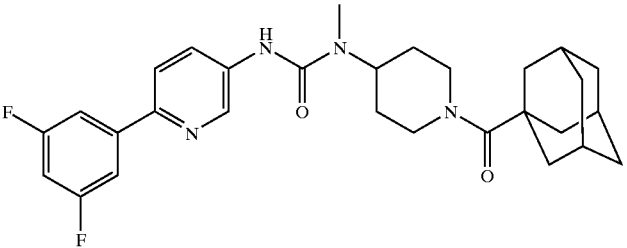<br>4V | (CDCl₃) δ 8.50 (d, J = 2.4 Hz, 1H), 8.13 (m, 1H), 7.62 (d, J = 8.4 Hz, 1H), 7.46 (m, 2H), 6.83 (s, 1H), 6.78 (m, 1H), 4.64 (m, 2H), 4.52 (m, 1H), 2.89 (s, 3H), 2.84 (m, 2H), 2.04–1.54 (m, 19H). | 509 |

| STRUCTURE | ¹H NMR | MS (M + H)⁺ |
|---|---|---|
| 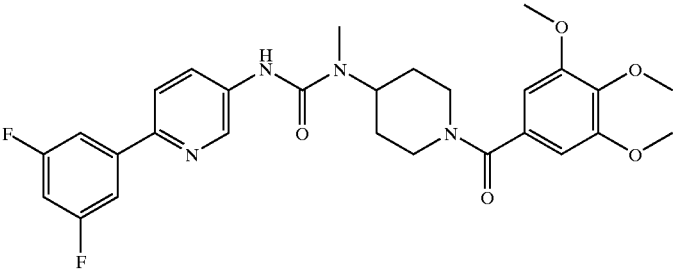<br>4W | (CDCl₃) δ 8.52 (m, 1H), 8.15 (m, 1H), 7.63 (d, J = 8.8 Hz, 1H), 7.48 (m, 2H), 6.80 (m, 1H), 6.69 (s, 1H), 6.63 (m, 2H), 4.82 (m, 1H), 4.56 (m, 1H), 3.86 (m, 10H), 3.15 (m, 1H), 2.94 (m, 4H), 1.76 (m, 4H). | 541 |
| 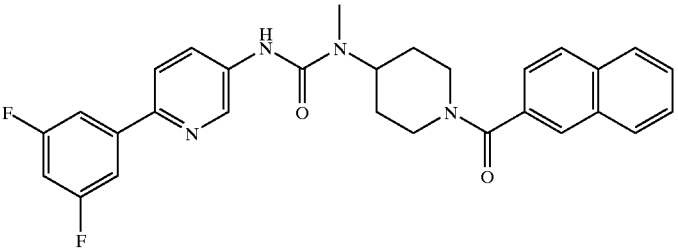<br>4X | (CDCl₃) δ 8.51 (m, 2H), 8.15 (m, 1H), 7.92 (m, 3H), 7.65 (m, 2H), 7.50 (m, 4H), 6.80 (m, 1H), 6.51 (s, 1H), 4.92 (m, 1H), 4.60 (m, 1H), 3.98 (m, 1H), 3.21 (m, 1H), 2.97 (m, 4H), 1.88–1.50 (m, 4H). | 501 |
| 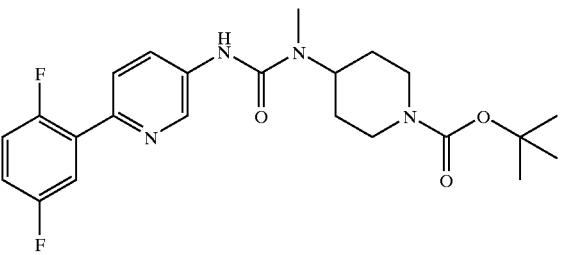<br>4Y | (CDCl₃) δ 8.57 (d, J = 2.8 Hz, 1H), 8.11 (m, 1H), 7.80 (m, 1H), 7.74 (m, 1H), 7.08 (m, 1H), 7.01 (m, 1H), 6.50 (s, 1H), 4.44 (m, 1H), 4.22 (m, 2H), 2.92 (s, 3H), 2.81 (m, 2H), 1.71–1.57 (m, 4H), 1.47 (s, 9H). | 447 |
| 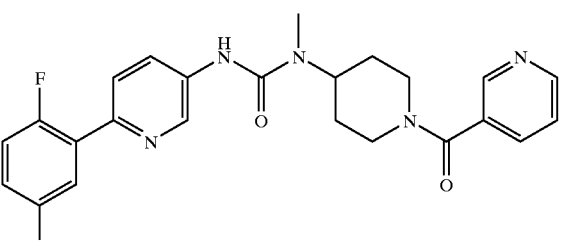<br>4Z | (CD₃OD) δ 9.30 (d, J = 2.4 Hz, 1H), 9.09 (s, 1H), 8.97 (d, J = 5.6 Hz, 1H), 8.74 (d, J = 8.4 Hz, 1H), 8.65 (m, 1H), 8.19 (m, 2H), 7.62 (m, 1H), 7.45 (m, 2H), 4.80 (m, 1H), 4.50 (m, 1H), 3.76 (m, 1H), 4.46 (m, 1H), 3.38 (m, 1H), 3.04 (s, 4H), 2.00–1.65 (m, 4H). | 452 |
| 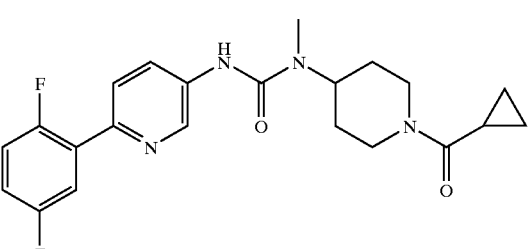<br>4AA | (CDCl₃) δ 8.57 (m, 1H), 8.10 (m, 1H), 7.79 (d, J = 7.6 Hz, 1H), 7.71 (m, 1H), 7.08 (m, 1H), 7.01 (m, 1H), 6.52 (s, 1H), 4.75 (m, 1H), 4.56 (m, 1H), 4.33 (m, 1H), 3.21 (m, 1H), 2.91 (s, 3H), 2.66 (m, 1H), 1.82–1.62 (m, 5H), 0.99 (m, 2H), 0.78 (m, 2H). | 415 |

| STRUCTURE | ¹H NMR | MS (M + H)⁺ |
|---|---|---|
| 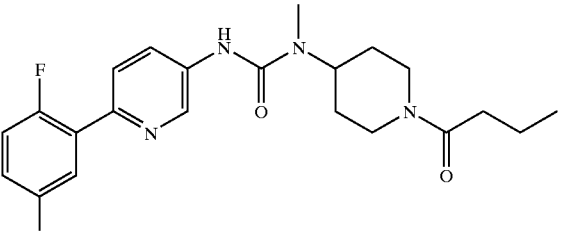 4BB | (CDCl₃) δ 8.57 (d, J = 2.8 Hz, 1H), 8.09 (m, 1H), 7.78 (d, J = 8.0 Hz, 1H), 7.69 (m, 1H), 7.07 (m, 1H), 7.01 (m, 1H), 6.64 (s, 1H), 4.47 (m, 1H), 4.53 (m, 1H), 3.94 (m, 1H), 3.13 (t, 1H), 2.91 (s, 3H), 2.60 (t, 1H), 2.33 (t, 2H), 1.78–1.54 (m, 6H), 0.96 (t, 3H). | 417 |
| 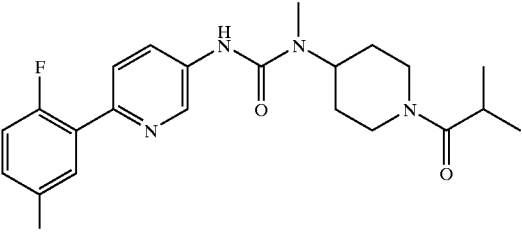 4CC | (CD₃OD) δ 8.29 (d, J = 2.0 Hz, 1H), 8.60 (m, 1H), 8.19 (d, J = 9.2 Hz, 1H), 7.61 (m, 1H), 7.45 (m, 2H), 4.70 (m, 1H), 4.41 (m, 1H), 4.18 (m, 1H), 3.21 (m, 1H), 2.93 (s, 4H), 2.69 (m, 1H), 1.77 (m, 4H), 1.14–1.09 (m, 6H). | 417 |
| 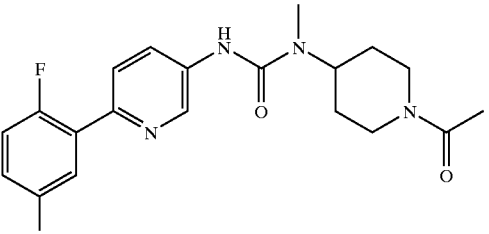 4DD | (CDCl₃) δ 8.57 (s, 1H), 8.08 (m, 1H), 7.76 (d, J = 6.8 Hz, 1H), 7.68 (m, 1H), 7.10 (m, 1H), 7.02 (m, 1H), 6.80 (s, 1H), 4.75 (d, 1H), 4.51 (m, 1H), 3.88 (d, 1H), 3.16 (t, 1H), 2.90 (s, 3H), 2.59 (t, 1H), 2.11 (s, 3H), 1.80–1.56 (m, 4H). | 389 |
| 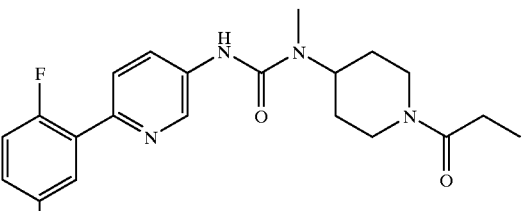 4EE | (CDCl₃) δ 8.56 (s, 1H), 8.08 (d, J = 8.8 Hz, 1H), 7.77 (d, J = 7.2 Hz, 1H), 7.68 (m, 1H), 7.08 (m, 1H), 7.01 (m, 1H), 6.72 (s, 1H), 4.77 (d, 1H), 4.51 (m, 1H), 3.94 (d, 1H), 3.11 (t, 1H), 2.90 (s, 3H), 2.60 (t, 1H), 2.34 (q, 2H), 1.80–1.54 (m, 4H), 1.15 (t, 3H). | 403 |
| 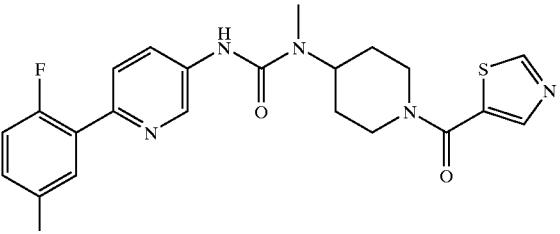 4FF | (CDCl₃) δ 8.89 (s, 1H), 8.62 (s, 1H), 8.12 (m, 1H), 8.07 (s, 1H), 7.80 (d, J = 6.4 Hz, 1H), 7.70 (m, 1H), 7.11 (m, 1H), 7.01 (m, 1H), 6.64 (bs, 1H), 4.80–4.20 (m, 3H), 3.35–2.80 (m, 5H), 1.86–1.69 (m, 4H). | 459 |

EXAMPLE 5

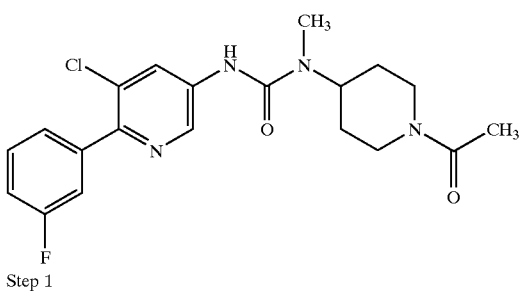

Step 1

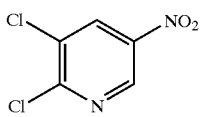
5-1

A solution of 2-hydroxy-5-nitropyridine (11.2 g, 79.9 mmol) in conc. HCl (57 ml) was warmed to 50° C. and KCl₃ (3.4 g, 27.7 mmol) in water (50 ml) was added dropwise at such a rate that the temperature was kept below 60° C. During the addition the product began to separate. After TLC monitoring indicated complete consumption of starting material the mixture was cooled to 0° C. and the product was isolated by vacuum filtration. The solid was washed with water and dried at 50° C. under vacuum to give the product (12.3 g, 88%) as a solid. $^1$HNMR (DMSO-$d_6$) δ 8.68 (d, J=3.2 Hz, 1H), 8.40 (d, J=3.2 Hz, 1H). MS m/e 175 (M+H)$^+$.

Step 2

5-2

Cl—[pyridine]—NO₂
   |
   Cl

To phosphoryl chloride (10.5 g, 68.7 mmol) was added successively, with cooling at 5° C., quinoline (4.4 g, 34.1 mmol) and the product of Step 1 (12.0 g, 68.7 mmol). The resultant mixture was heated for 2 hr at 120° C. under N₂. After the reaction was complete as indicated by TLC monitoring, the reaction mixture was allowed to cool to 100° C., and water (26 ml) was added. The solution was then cooled in an ice bath and the product was isolated by vacuum filtration. The solid was washed with water and dried at 40° C. under vacuum to give the product (12.5 g, 94%). $^1$HNMR (DMSO-$d_6$) δ 9.19 (d, J=2.4 Hz, 1H), 8.97 (d, J=2.4 Hz, 1H).

Step 3

5-3

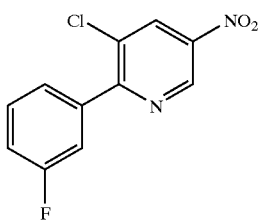

A flask charged with 3-fluorophenylboronic acid (1.63 g, 11.65 mmol), the product of Step 2 (1.50 g, 7.77 mmol), ethylene glycol dimethyl ether (18 ml) and potassium phosphate (4.95 g, 23.3 mmol) was purged with N₂. PdCl₂(dppf)₂·CH₂Cl₂ (0.26 g, 0.32 mmol) was added. The reaction mixture was heated at 80° C. under N₂ for 2 hr, allowed to cool, and filtered through celite. The filtrate was extracted with EtOAc (60 ml) was then washed with saturated sodium carbonate (40 ml), water (40 ml), brine (30 ml), dried (Na₂SO₄), filtered and concentrated. The residue was subjected to flash chromatography (1:5 CH₂Cl₂/hexane) to give the product (1.96 g, 100%). $^1$HNMR (CDCl₃) δ 9.39 (d, J=2.4 Hz, 1H), 8.62 (d, J=2.4 Hz, 1H), 7.62 (m, 1H), 7.54 (m, 2H), 7.22 (m, 1H). MS m/e 253 (M+H)$^+$.

Step 4

5-4

Cl—[pyridine]—NH₂
   |
   [3-fluorophenyl]

To an ice-cold solution of the product of Step 3 (2.25 g, 8.9 mmol) and nickel chloride hexahydrate (4.23 g, 17.8 mmol) in MeOH (100 ml) was added sodium borohydride (1.11 g, 29.5 mmol) in portions. The resulting mixture was stirred at 0–5° C. for 30 min., water (5 ml) was added and the whole was concentrated. The residue was treated with EtOAc (100 ml) and filtered through celite. The filtrate was dried (MgSO₄), filtered and concentrated to give the product (2.3 g). $^1$HNMR (CDCl₃) δ7.53 (s, 1H), 6.97 (m, 1H), 6.84 (m, 2H), 6.63 (s, 1H), 6.53 (m, 1H), 3.90 (s, b, 2H).

Step 5

5-5

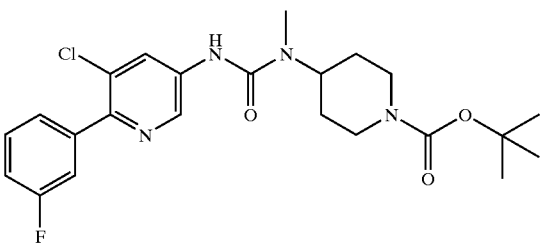

To a solution of the product of Step 4 (500 mg, 2.25 mmol) in anhydrous pyridine (6 ml) was added phenyl chloroformate (390 mg, 2.49 mmol) dropwise. The reaction mixture was stirred for 16 hr then evaporated in vacuo. The residue was taken up in chloroform (10 ml), and Et₃N (1 ml) and Preparation 1 (722 mg, 3.37 mmol) was added. The mixture was heated at 65° C. for 3 hr. The residue was allowed to cool, diluted with CH₂Cl₂ (50 ml) and washed with sat'd NaHCO₃ (30 ml), water (30 ml), and NaCl (30 ml). The organic layer was dried (MgSO₄), filtered and evaporated. The residue was subjected to flash chromatography (2:98 CH₃OH/CH₂Cl₂) to give the product (530 mg, 51%). $^1$H NMR (CDCl₃) δ 8.41 (d, J=2.4 Hz, 1H), 8.28 (d, J=2.4 Hz, 1H), 7.50 (m, 1H), 7.42 (m, 2H), 7.10 (m, 1H), 6.61 (s, 1H), 4.41 (m, 1H), 4.22 (m, 2H), 2.92 (s, 3H), 2.80 (m, 2H), 1.70–1.57 (m, 4H), 1.45 (s, 9H).

Step 6

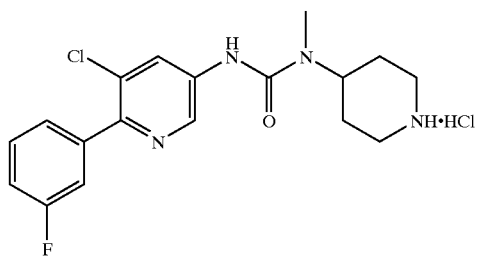

5-6

The product of Step 5 (90 mg, 0.194 mmol) was treated with 4N HCl/1,4-dioxane (4 ml) for 16 hr. The reaction mixture was concentrated and the residue was triturated with Et$_2$O and dried to give the product (85 mg) as a solid.

$^1$HNMR (CD$_3$OD) δ 8.92 (d, J=2.4 Hz, 1H), 8.50 (d, J=2.4 Hz, 1H), 7.58 (m, 1H), 7.51 (m, 2H), 7.30 (m, 1H), 4.45 (m, 1H), 3.50 (m, 2H), 3.16 (m, 2H), 3.02 (s, 3H), 2.10–1.90 (m, 4H).

Step 7

To a solution of the product of Step 6 (42 mg, 0.096 mmol) and Et$_3$N (0.2 ml) in CH$_2$Cl$_2$ (2 ml) was slowly added acetic ankydride (112 mg, 1.10 mmol). The reaction mixture was stirred at R.T. for 2 hr. The concentrated residue was separated by PTLC (1:20 CH$_3$OH/CH$_2$Cl$_2$) to give the product (31 mg, 80%). $^1$HNMR (CDCl$_3$) δ 8.44 (d, J=2.4 Hz, 1H), 8.27 (d, J=2.4 Hz, 1H), 7.50 (m, 1H), 7.42 (m, 2H), 7.10 (m, 1H), 6.92 (s, 1H), 4.75 (m, 1H), 4.50 (m, 1H), 3.92 (m, 1H), 3.17 (t, 1H), 2.90 (s, 3H), 2.60 (m, 1H), 2.11 (s, 3H), 1.81–1.60 (m, 4H). MS m/e 405 (M+H)$^+$.

Use of the appropriate reagents and procedures afforded the following compounds:

| STRUCTURE | $^1$H NMR | MS (M + H)$^+$ |
|---|---|---|
| 5A | (CDCl$_3$) δ 8.44 (d, J = 2.4 Hz, 1H), 8.24 (d, J = 2.4 Hz, 1H), 7.49 (m, 1H), 7.43 (m, 2H), 7.10 (m, 1H), 6.65 (s, 1H), 4.43 (m, 1H), 3.92 (m, 2H), 2.93 (s, 3H), 2.78 (m, 5H), 1.81 (m, 4H). | 441 |
| 5B | (CDCl$_3$) δ 8.44 (d, J = 2.4 Hz, 1H), 8.25 (d, J = 2.4 Hz, 1H), 7.50 (m, 1H), 7.41 (m, 2H), 7.10 (m, 1H), 6.61 (s, 1H), 4.44 (m, 1H), 3.93 (m, 2H), 2.93 (m, 7H), 1.81 (m, 4H), 1.36 (t, 3H). | 455 |
| 5C | (CDCl$_3$) δ 8.44 (d, J = 2.0 Hz, 1H), 8.24 (d, J = 2.4 Hz, 1H), 7.50 (m, 1H), 7.41 (m, 2H), 7.10 (m, 1H), 6.67 (s, 1H), 4.44 (m, 1H), 3.93 (m, 2H), 2.90 (m, 7H), 1.81 (m, 6H), 1.06 (t, 3H). | 469 |

-continued
| STRUCTURE | ¹H NMR | MS (M + H)⁺ |
|---|---|---|
| 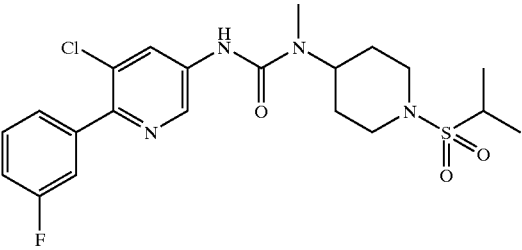<br>5D | (CDCl₃) δ 8.43 (d, J = 2.4 Hz, 1H), 8.26 (d, J = 2.4 Hz, 1H), 7.51 (m, 1H), 7.43 (m, 2H), 7.10 (m, 1H), 6.60 (s, 1H), 4.46 (m, 1H), 3.96 (m, 2H), 3.19 (m, 1H), 3.01 (m, 2H), 2.93 (s, 3H), 1.79 (m, 4H), 1.34 (d, 6H). | 469 |
| 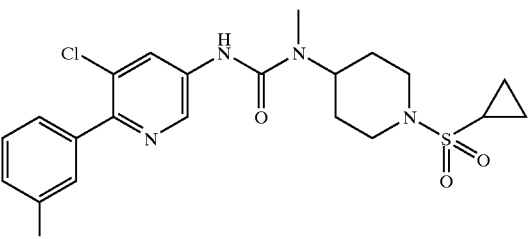<br>5E | (CDCl₃) δ 8.43 (d, J = 2.4 Hz, 1H), 8.26 (d, J = 2.4 Hz, 1H), 7.51 (m, 1H), 7.43 (m, 2H), 7.10 (m, 1H), 6.64 (s, 1H), 4.43 (m, 1H), 3.92 (m, 2H), 2.93 (m, 5H), 2.27 (m, 1H), 1.81 (m, 4H), 1.16 (m, 2H), 1.00 (m, 2H). | 467 |
| 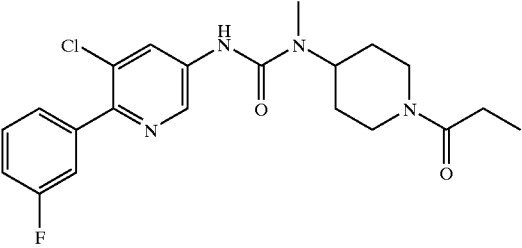<br>5F | (CDCl₃) δ 8.44 (d, J = 2.0 Hz, 1H), 8.26 (d, J = 2.4 Hz, 1H), 7.48 (m, 1H), 7.40 (m, 2H), 7.10 (m, 1H), 6.92 (s, 1H), 4.76 (m, 1H), 4.50 (m, 1H), 3.94 (m, 1H), 3.12 (t, 1H), 2.90 (s, 3H), 2.60 (m, 1H), 2.36 (q, 2H), 1.80–1.55 (m, 4H), 1.15 (t, 3H). | 419 |
| 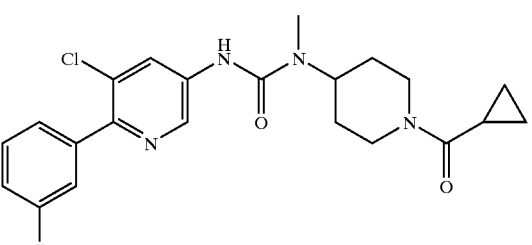<br>5G | (CDCl₃) δ 8.43 (d, J = 2.4 Hz, 1H), 8.26 (d, J = 2.4 Hz, 1H), 7.50 (m, 1H), 7.40 (m, 2H), 7.10 (m, 1H), 6.89 (s, 1H), 4.76 (m, 1H), 4.51 (m, 1H), 3.32 (m, 1H), 3.12 (m, 1H), 2.90 (s, 3H), 2.64 (m, 1H), 1.89–1.55 (m, 5H), 0.98 (m, 2H), 0.77 (m, 2H). | 431 |
| 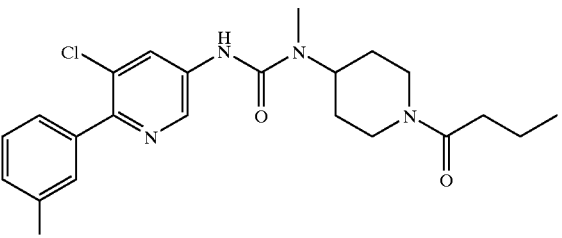<br>5H | (CDCl₃) δ 8.43 (d, J = 2.4 Hz, 1H), 8.27 (d, J = 2.4 Hz, 1H), 7.50 (m, 1H), 7.40 (m, 2H), 7.10 (m, 1H), 6.78 (s, 1H), 4.79 (m, 1H), 4.50 (m, 1H), 3.96 (m, 1H), 3.13 (t, 1H), 2.91 (s, 3H), 2.60 (m, 1H), 2.33 (q, 2H), 1.81–1.55 (m, 6H), 0.97 (t, 3H). | 433 |

-continued

| STRUCTURE | ¹H NMR | MS (M + H)⁺ |
|---|---|---|
| 5I | (CDCl₃) δ 8.43 (d, J = 2.4 Hz, 1H), 8.25 (d, J = 2.4 Hz, 1H), 7.48 (m, 1H), 7.38 (m, 2H), 7.08 (m, 1H), 7.02 (s, 1H), 4.39 (m, 1H), 3.75 (m, 2H), 2.90–2.80 (m, 11H), 1.67 (m, 4H). | 434 |
| 5J | (CDCl₃) δ 8.43 (d, J = 2.4 Hz, 1H), 8.30 (d, J = 2.4 Hz, 1H), 7.50 (m, 1H), 7.43 (m, 2H), 7.08 (m, 1H), 6.69 (s, 1H), 4.41 (m, 1H), 3.75 (m 2H), 3.20 (q, 4H), 2.90 (s, 3H), 2.85 (m, 2H), 1.69 (m, 4H), 1.27 (t, 6H). | 462 |
| 5K | (CDCl₃) δ 8.43 (d, J = 2.0 Hz, 1H), 8.27 (d, J = 2.4 Hz, 1H), 7.49 (m, 1H), 7.40 (m, 2H), 7.09 (m, 1H), 6.87 (s, 1H), 4.80 (m, 1H), 4.51 (m, 1H), 4.05 (m, 1H), 3.14 (m, 1H), 2.90 (s, 3H), 2.80 (m, 1H), 2.59 (m, 1H), 1.82–1.56 (m, 4H), 1.13 (m, 6H). | 433 |
| 5L | (CDCl₃) δ 8.40 (d, J = 2.0 Hz, 1H), 8.32 (d, J = 2.4 Hz, 1H), 7.29 (m, 2H), 6.85 (m, 1H), 6.49 (m, 1H), 4.42 (m, 1H), 4.23 (m, 2H), 2.93 (s, 3H), 2.81 (m, 2H), 1.70–1.57 (m, 4H), 1.45 (m, 9H). | 481 |
| 5M | (CDCl₃) δ 8.44 (d, J = 2.0 Hz, 1H), 8.24 (d, J = 2.0 Hz, 1H), 7.27 (m, 2H), 6.84 (m, 1H), 6.73 (s, 1H), 4.41 (m, 1H), 3.92 (m, 2H), 2.93 (s, 3H), 2.78 (m, 5H), 1.81 (m, 4H). | 459 |

-continued
| STRUCTURE | ¹H NMR | MS (M + H)⁺ |
|---|---|---|
| 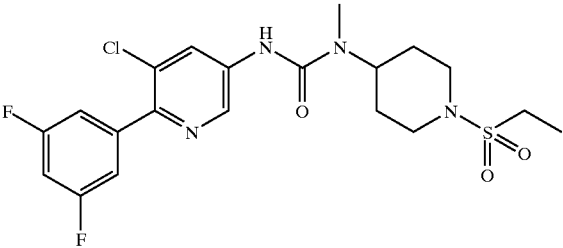<br>5N | (CDCl₃) δ 8.43 (m, 1H), 8.28 (m, 1H), 7.28 (m, 2H), 6.84 (m, 1H), 6.54 (s, 1H), 4.45 (m, 1H), 3.94 (m, 2H), 2.95 (m, 7H), 1.81 (m, 4H), 1.36 (t, 3H). | 473 |
| 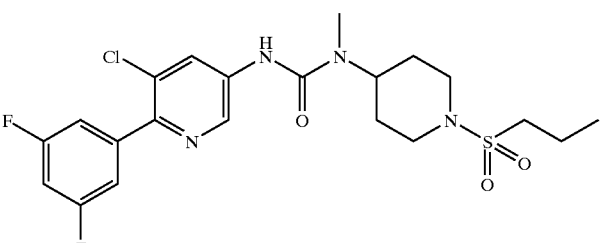<br>5O | (CDCl₃) δ 8.42 (d, J = 2.0 Hz, 1H), 8.28 (d, J = 2.0 Hz, 1H), 7.27 (m, 2H), 6.84 (m, 1H), 6.52 (s, 1H), 4.45 (m, 1H), 3.94 (m, 2H), 2.95 (s, 3H), 2.88 (m, 4H), 1.85 (m, 6H), 1.07 (t, 3H). | 487 |
| 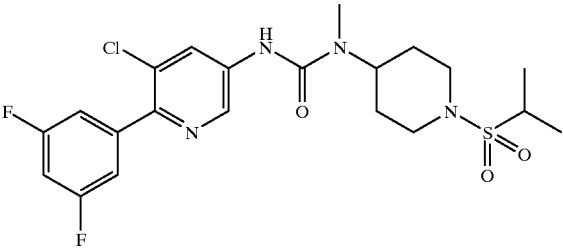<br>5P | (CDCl₃) δ 8.43 (d, J = 2.4 Hz, 1H), 8.27 (d, J = 2.4 Hz, 1H), 7.27 (m, 2H), 6.84 (m, 1H), 6.58 (s, 1H), 4.45 (m, 1H), 3.94 (m, 2H), 3.19 (m, 1H), 3.00 (m, 2H), 2.95 (s, 3H), 1.75 (m, 4H), 1.35 (d, 6H). | 487 |
| 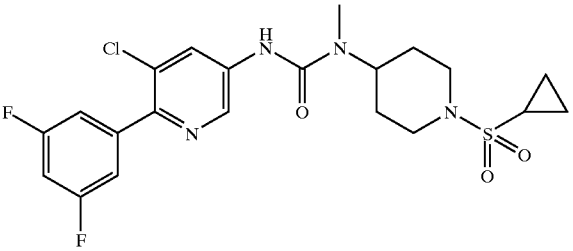<br>5Q | (CDCl₃) δ 8.44 (d, J = 2.0 Hz, 1H), 8.27 (d, J = 2.4 Hz, 1H), 7.27 (m, 2H), 6.84 (m, 1H), 6.60 (s, 1H), 4.41 (m, 1H), 3.92 (m, 2H), 2.95 (m, 5H), 2.28 (m, 1H), 1.81 (m, 4H), 1.17 (m, 2H), 1.00 (m, 2H). | 485 |

EXAMPLE 6

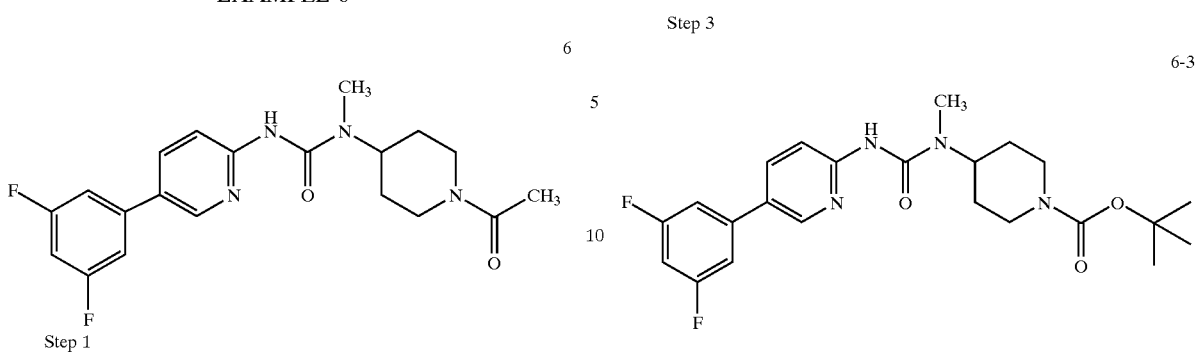

Step 1

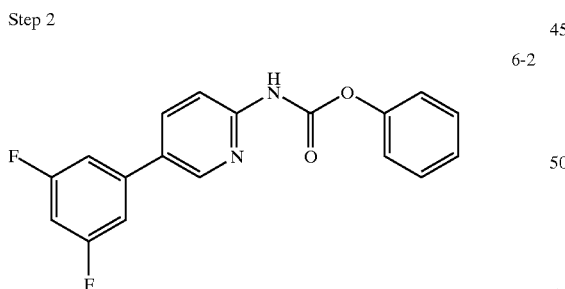

A round bottom flask charged with 3,5-difluorophenylboronic acid (6.60 g, 41.8 mmol), 2-amino-5-bromo pyridine (6.00 g, 34.7 mmol), benzene (80 ml), and 2M aq. Na$_2$CO$_3$ (40 ml) was purged with N$_2$ for 5 min. Pd(PPh$_3$)$_4$ (1.20 g, 1.04 mmol) was added and the reaction mixture was heated to 100° C. for 16 hr. After cooling, the reaction mixture was poured into cold water (100 ml). The whole was extracted with CH$_2$Cl$_2$ (3×150 ml), dried (Na$_2$SO$_4$), and filtered. The concentrated residue was subjected to flash column chromatography (1:10 acetone/hexane) to give the product (4.90 g, 69%). $^1$H NMR (CDCl$_3$) δ 8.28 (d, J=2.4 Hz, 1H), 7.63 (dd, J=8.8, 2.4 Hz, 1H), 7.01 (m, 2H), 6.76 (m, 1H), 6.58 (d, J=8.4 Hz, 1H), 4.65 (s, b, 2H). MS m/e 207 (M+H)$^+$.

Step 2

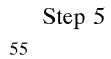

To a solution of the product of Step 1 (0.300 g, 1.45 mmol) in anhydrous pyridine (5 ml) was added phenyl chloroformate (0.20 ml, 1.60 mmol) dropwise under argon. The reaction mixture was stirred at R.T. for 16 hr and evaporated in vacuo to give crude the product (0.388 g). $^1$H NMR (CDCl$_3$) δ 8.53 (m, 1H), 8.42 (t, 2H), 8.15 (d, 1H), 7.41 (t, 2H), 7.24 (m, 3H), 7.07 (m, 2H), 6.83 (m, 1H) MS m/e 327 (M+H)$^+$.

Step 3

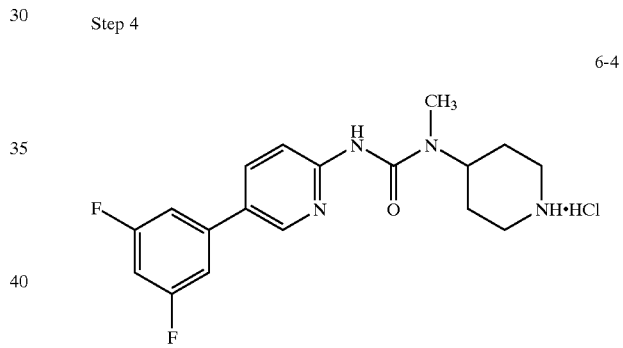

To a solution of the product of Step 2 (0.200 g, 0.613 mmol) in chloroform (10 ml) was added Preparation 1 (HCl salt) (0.230 g, 0.919 mmol) and Et$_3$N (0.43 ml, 3.06 mmol). The reaction mixture was refluxed for 16 hr, then allowed to cool and concentrated. Subjection of the residue to PTLC (1:2 EtOAc/hexane) gave the product (0.062 g, 23%) as a solid. $^1$HNMR (CDCl$_3$) δ 8.40 (s, 1H), 8.16 (d, 1H), 7.85 (m, 1H), 7.27 (s, 1H), 7.07 (m, 2H), 6.69 (m, 1H), 4.42 (m, 1H), 4.25 (s, b, 2H), 2.92 (s, 3H), 2.82 (m, 2H), 1.67 (m, 4H), 1.47 (s, 9H). MS m/e 447 (M+H)$^+$.

Step 4

A mixture of the product of Step 3 (0.205 g, 0.460 mmol) and 4N HCl/1,4-dioxane (5 ml) was stirred at R.T. for 1 hr, then evaporated to give the product (0.137 g, 100%) as a solid. MS m/e 347 (M+H)$^+$.

Step 5

To a solution of the product of Step 4 (0.042 g, 0.11 mmol) and iPr$_2$NEt (0.057 ml, 0.33 mmol) in CH$_2$Cl$_2$ (2.0 ml) was slowly added acetyl chloride (7.0 μl, 0.1 mmol). The reaction mixture was stirred at R.T. for 16 hr, then concentrated. Subjection of the residue to PTLC (1:10 MeOH/CH$_2$Cl$_2$) gave the product (0.030 g, 78%) as a solid. $^1$HNMR (CDCl$_3$) δ 8.39 (m, 1H), 8.15 (m, 1H), 7.83 (dd, J=8.8,2.4 Hz, 1H), 7.28 (s, 1H), 7.06 (m, 2H), 6.79 (m, 1H), 4.78 (m, 1H), 4.51 (m, 1H), 3.92 (m, 1H), 3.18 (m, 1H), 2.91 (s, 3H), 2.62 (m, 1H), 2.12 (s, 3H), 1.78 (m, 2H), 1.60 (m, 2H). MS m/e 389 (M+H)$^+$.

| STRUCTURE | ¹H NMR | MS (M + H)⁺ |
|---|---|---|
| 6A | ¹H NMR (DMSO-d6) δ 8.44 (1H, s), 8.11 (1H, m), 7.88 (1H, m), 7.55 (2H, m), 7.45 (2H, m), 7.35 (1H, m), 4.39 (1H, m), 3.20 (2H, m), 2.97 (3H, s), 2.49 (3H, s), 2.40 (2H, m), 2.13 (2H, m), 1.76 (2H, m). | 325 |
| 6B | (CDCl₃) δ 8.40 (d, J = 2.0 Hz, 1H), 8.14 (d, J = 8.8 Hz, 1H), 7.84 (dd, J = 8.8 Hz, 1H), 7.29 (s, 1H), 7.07 (m, 2H), 6.80 (m, 1H), 4.44 (m, 1H), 3.93 (m, 2H), 2.96 (s, 3H), 2.81 (s, 3H), 2.80 (m, 2H), 1.84 (m, 4H) | 425 |
| 6C | (CDCl₃) δ 8.39 (d, J = 2.4 Hz, 1H), 8.15 (d, J = 8.8 Hz, 1H), 7.83 (dd, J = 8.8, 2.4 Hz, 1H), 7.30 (s, 1H), 7.06 (m, 2H), 6.79 (m, 1H), 4.79 (m, 1H), 4.51 (m, 1H), 3.94 (d, b, 1H), 3.13 (m, 1H), 2.91 (s, 3H), 2.61 (m, 1H), 2.37 (q, J = 7.6 Hz, 2H), 1.78 (m, 2H), 1.60 (m, 2H), 1.16 (t, J = 7.6 Hz, 3H) | 403 |
| 6D | (CDCl₃) δ 8.40 (d, J = 2.0 Hz, 1H), 8.15 (d, J = 8.8 Hz, 1H), 7.83 (dd, J = 8.8, 2.4 Hz, 1H), 7.27 (s, 1H), 7.60 (m, 2H), 6.79 (m, 1H), 4.82 (m, 1H), 4.51 (m, 1H), 3.97 (d, b, 1H), 3.14 (m, 1H), 2.91 (s, 3H), 2.61 (m, 1H), 2.33 (t, J = 6.8 Hz, 2H), 1.90–1.50 (m, 6H), 0.98 (t, J = 7.6 Hz, 3H) | 417 |
EXAMPLE 7
Step 1
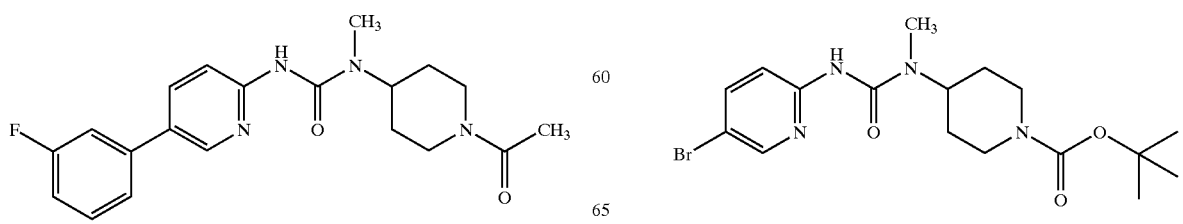

To a solution of 2-amino-5-bromopyridine (5.00 g, 28.9 mmol) in anhydrous pyridine (50 ml) was added phenyl chloroformate (4.0 ml, 31.8 mmol) dropwise under argon. The reaction mixture was stirred for 22 hr, then poured into EtOAc (200 ml). The resultant precipitate was collected, washed with EtOAc, and dried in vacuo.

To a solution of the crude product was added Preparation 1 (6.19 g, 28.9 mmol), Et$_3$N (12.0 ml, 86.7 mmol) and CHCl$_3$ (100 ml). The reaction mixture was refluxed for 24 hr, allowed to cool and poured into cold H$_2$O (~200 ml). The whole was extracted with CH$_2$Cl$_2$ (3×200 ml), dried (Na$_2$SO$_4$), filtered and evaporated. The residue was subjected to flash chromatography (1:4 then 1:2 EtOAc/hexane) to give the product as a solid (7.20 g, 60%). $^1$H NMR (CDCl$_3$) δ 8.17 (m, 1H), 7.94 (m, 1H), 7.68 (m, 1H), 7.22 (s, 1H), 4.32 (m, 1H), 4.18 (s, b, 2H), 2.83 (s, 3H), 2.74 (m, 2H), 1.58 (m, 4H), 1.41 (s, 9H). MS m/e 413 (M+H)$^+$.

Step 2

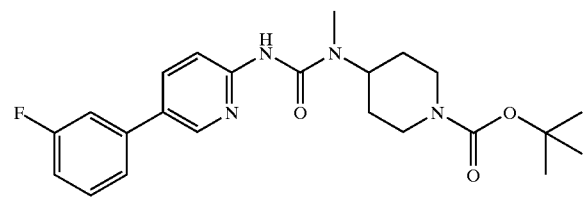

7-2

A flask charged with 3-fluorophenyl boronic acid (0.537 g, 3.87 mmol), the product of Step 1 (7-1), (0.800 g, 1.94 mmol), Cs$_2$CO$_3$ (0.695 g, 2.13 mmol), toluene (30 ml) and H$_2$O (1 ml) was purged with N$_2$. PdCl$_2$(dppf)$_2$·CH$_2$Cl$_2$ (0.317 g, 0.387 mmol) was added, and the reaction mixture was refluxed for 1.5 hr, allowed to cool, then poured into cold water (100 ml). The whole was extracted with CH$_2$Cl$_2$ (3×100 ml) and dried (Na$_2$SO$_4$). The concentrated residue was subjected to PTLC (1:2 acetone/hexane) to give the product (0.382 g, 46%) as a film. $^1$H NMR (CDCl$_3$) δ 8.41 (d, 1H), 8.15 (d, 1H), 7.86 (dd, 1H), 7.42–7.20 (m, 4H), 7.05 (m, 1H), 4.42 (m, 1H), 4.33 (s, b, 2H), 2.92 (s, 3H), 2.82 (m, 2H), 1.78–1.50 (m, 4H), 1.46 (m, 9H). MS m/e 429 (M+H)$^+$.

Step 3

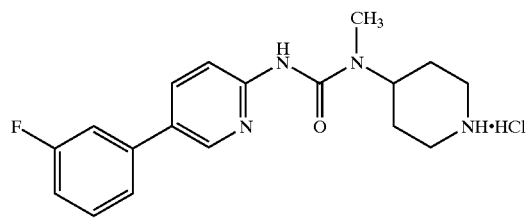

7-3

Reaction of the product of Step 2 by the method of Example 6, Step 4 gave the product. MS m/e 329 (M+H)$^+$.

Step 4

Using essentially the same procedure as Example 4, reaction of the product of Step 3 with CH$_3$COCl and Et$_3$N gave the product. $^1$H NMR (CDCl$_3$) δ 8.42 (d, 1H), 8.13 (m, 1H), 7.87 (m, 1H), 7.45–7.20 (m, 4H), 7.05 (m, 1H), 4.78 (m, 1H), 4.51 (m, 1H), 3.92 (m, 1H), 3.18 (m, 1H), 2.91 (s, 3H), 2.63 (m, 1H), 2.12 (s, 3H), 1.78 (m, 2H), 1.60 (m, 2H). MS m/e 371 (M+H)$^+$.

Using appropriate procedures, the following Examples were prepared.

| STRUCTURE | $^1$H NMR | MS (M + H)$^+$ |
|---|---|---|
| 7A | (CDCl$_3$) δ 8.37 (s, 1H), 8.15 (d, 1H), 7.83 (m, 1H), 7.28 (s, 1H), 7.13 (m, 2H), 7.01 (m, 1H), 4.41 (m, 1H), 4.22 (s, b, 2H), 2.91 (s, 3H), 2.80 (m, 2H), 1.75–1.50 (m, 4H), 1.46 (s, 9H) | 447 |
| 7B | (CDCl$_3$) δ 8.39 (s, 1H), 8.15 (d, 1H), 7.85 (d, 1H), 7.32 (s, b, 1H), 7.14 (m, 2H), 7.03 (m, 1H), 4.43 (m, 1H), 3.94 (d, b, 2H), 2.95 (s, 3H), 2.81 (s, 3H), 2.78 (m, 2H), 1.84 (m, 4H) | 425 |

| STRUCTURE | ¹H NMR | MS (M + H)⁺ |
|---|---|---|
| 7C | (CDCl₃) δ 8.39 (s, 1H), 8.14 (d, 1H), 7.84 (d, 1H), 7.26 (s, 1H), 7.14 (m, 2H), 7.00 (m, 1H), 4.78 (d, b, 1H), 4.51 (m, 1H), 3.91 (d, b, 1H), 3.18 (m, 1H), 2.91 (s, 3H), 2.62 (m, 1H), 2.12 (s, 3H), 1.78 (m, 2H), 1.61 (m, 2H) | 389 |
| 7D | (CDCl₃) δ 8.39 (s, 1H), 8.15 (d, 1H), 7.85 (m, 1H), 7.27 (s, 1H), 7.14 (m, 2H), 7.02 (m, 1H), 4.81 (d, b, 1H), 4.51 (m, 1H), 3.95 (d, b, 1H), 3.14 (m, 1H), 2.91 (s, 3H), 2.62 (m, 1H), 2.37 (q, 2H), 1.77 (m, 2H), 1.61 (m, 2H), 1.16 (t, 3H) | 403 |
| 7E | (CDCl₃) δ 8.39 (s, 1H), 8.14 (dd, 1H), 7.85 (m, 1H), 7.26 (s, 1H), 7.12 (m, 2H), 7.02 (m, 1H), 4.81 (m, 1H), 4.51 (m, 1H), 3.97 (d, b, 1H), 3.14 (m, 1H), 2.91 (s, 3H), 2.61 (m, 1H), 2.33 (t, 2H), 1.90–1.50 (m, 6H), 0.98 (t, 3H) | 417 |
| 7F | (CDCl₃) δ 8.42 (d, 1H), 8.13 (d, 1H), 7.87 (dd, 1H), 7.45–7.20 (m, 4H), 7.06 (m, 1H), 4.45 (m, 1H), 3.93 (m, 2H), 3.05 (s, 3H), 2.81 (s, 3H), 2.80 (m, 2H), 1.83 (m, 4H) | 407 |
| 7G | (CDCl₃) δ 8.41 (d, 1H), 8.13 (d, 1H), 7.86 (dd, 1H), 7.45–7.20 (m, 4H), 7.05 (m, 1H), 4.81 (m, 1H), 4.52 (m, 1H), 3.95 (m, 1H), 3.13 (m, 1H), 2.91 (s, 3H), 2.62 (m, 1H), 2.36 (q, 2H), 1.75 (m, 2H), 1.58 (m, 2H), 1.16 (t, 3H) | 385 |

EXAMPLE 8

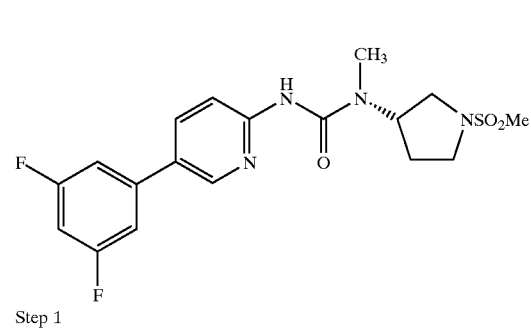

Step 1

8-1

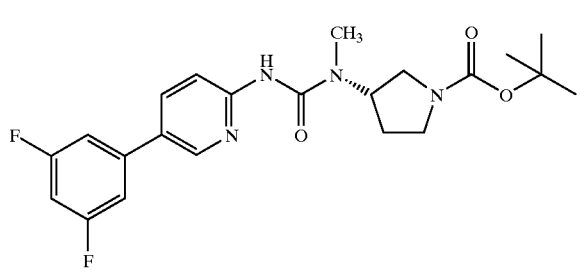

Reaction of 6-2 with Preparation 10 using the procedure of Example 6, Step 3, gave the product. ¹HNMR (CDCl₃) δ 8.38 (d, J=2.0 Hz, 1H), 8.13 (d, J=8.8 Hz, 1H), 7.82 (dd, J=8.8, 2.4 Hz, 1H), 7.36 (s, 1H), 7.06 (m, 2H), 6.78 (m, 1H), 5.04 (m, 1H), 3.70–3.10 (m, 4H), 2.98 (s, 3H), 2.10 (m, 1H), 1.97 (m, 1H), 1.45 (s, 9H). MS m/e 433 (M+H)⁺.

Step 2

8-2

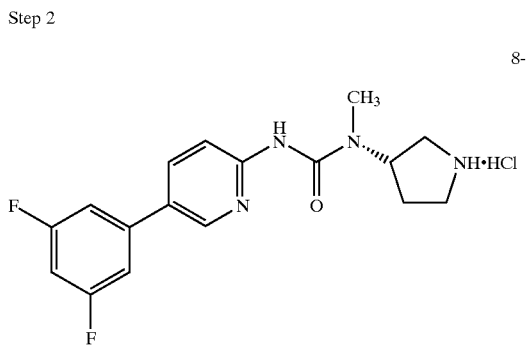

The product of Step 1 was treated with HCl by the procedure of Example 6, Step 4, to give the product. ¹H NMR (CD₃OD) δ 8.63 (m, 2H), 7.85 (d, 1H), 7.42 (m, 2H), 7.13 (m, 1H), 4.82 (m, 1H), 4.80–4.40 (m, 4H), 3.22 (s, 3H), 2.43 (m, 1H), 2.32 (m, 1H). MS m/e 333 (M+H)⁺.

Step 3

Using the procedure of Example 3, Step 3, the product was synthesized in 56% yield as a solid. ¹H NMR (CDCl₃) δ 8.38 (d, 1H), 8.22 (d, 1H), 7.90 (m, 1H), 7.26 (s, 1H), 7.06 (m, 2H), 6.83 (m, 1H), 5.15 (m, 1H), 3.67 (m, 1H), 3.52 (m, 1H), 3.35 (m, 1H), 3.25 (m, 1H), 3.07 (s, 3H), 2.90 (s, 3H), 2.25 (m, 1H), 2.08 (m, 1H). MS m/e 411 (M+H)⁺.

EXAMPLE 9

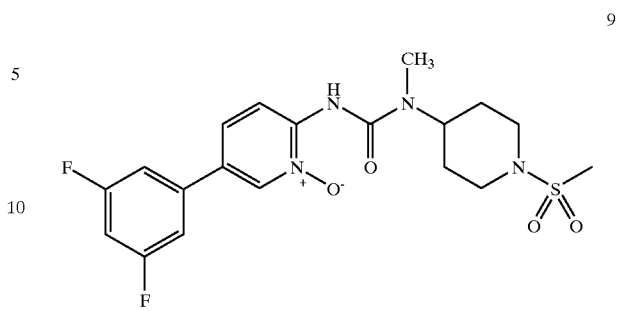

A mixture of Example 6B (0.030 g, 0.071 mmol), CH₂Cl₂ (5 ml) and mCPBA (57–80%, 0.032 g) was stirred at R.T. for 1.5 hr, then poured into H₂O (10 ml). The whole was extracted with CH₂Cl₂ (3×20 ml), dried (Na₂SO₄), filtered and concentrated. Subjection of the residue to PTLC (1:20 CH₃OH/CH₂Cl₂) gave the product (0.0194 mg, 62%) as a solid. ¹H NMR (CDCl₃) δ 9.81 (s, 1H), 8.46 (d, J=2.0 Hz, 1H), 8.37 (d, J=9.2 Hz, 1H), 7.49 (dd, J=8.8, 2.0 Hz, 1H), 7.04 (m, 2H), 6.86 (m, 1H), 4.39 (s, b, 1H), 3.95 (d, b, 2H), 3.02 (s, 3H), 2.83 (m, 5H), 1.88 (m, 4H). MS m/e 441 (M+H)⁺.

EXAMPLE 10

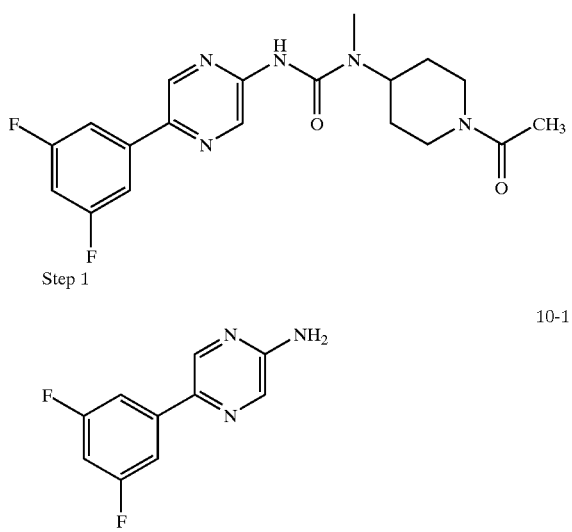

Step 1

10-1

A flask charged with 2-amino-5-bromopyrazine (4.00 g, 23.0 mmol), 3,5-difluorophenylboronic acid (5.44 g, 34.5 mmol), toluene (150 ml), water (5 ml) and cesium carbonate (8.24 g, 25.3 mmol) was purged with N₂. PdCl₂(dppf) .CH₂Cl₂ (0.93 g, 1.15 mmol) was added and the mixture was refluxed 2 hr, allowed to cool, then poured into cold water (100 ml). The whole was extracted with CH₂Cl₂ (3×200 ml), dried (Na₂SO₄), and filtered. The concentrated residue was subjected to flash column chromatography (1:4 then 1:2 acetone/hexane) to give the product (4.42 g, 93%). ¹HNMR (CDCl₃) δ 8.42 (d, J=1.6 Hz, 1H), 8.05 (d, J=1.2 Hz, 1H), 7.42 (m, 2H), 6.79 (m, 1H), 4.75 (s, 2H). MS m/e 208 (M+H)⁺.

Step 2

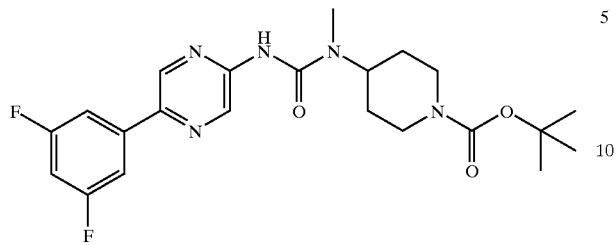
10-2

To a solution of the product of Step 1 (2.00 g, 9.65 mmol) in anhydrous pyridine (40 ml) was added phenyl chloroformate dropwise under argon. The reaction mixture was stirred for 16 hr, then concentrated. To the residue was added chloroform (50 ml), followed by Preparation 1 (3.10 g, 14.5 mmol) and Et$_3$N (4.0 ml, 28.9 mmol). The reaction mixture was refluxed for 4 hr, then allowed to cool and poured into water. The whole was extracted with CH$_2$Cl$_2$ (3×200 ml) and dried (Na$_2$SO$_4$), filtered and concentrated. Crystallization of the residue (acetone/hexane) gave the product (2.52 g, 58%). The mother liquor was concentrated and subjected to flash chromatography (1:5 acetone/hexane) to afford additional product (0.943 g, total 80%). $^1$H NMR (CDCl$_3$) δ 9.45 (d, J=1.6 Hz, 1H), 8.55 (d, J=1.2 Hz, 1H), 7.51 (m, 2H), 7.17 (s, 1H), 6.85 (m, 1H), 4.43 (m, 1H), 4.24 (m, 2H), 2.95 (s, 3H), 2.82 (m, 2H), 1.63 (m, 4H), 1.47 (s, 9H). MS m/e 448 (M+H)$^+$.

Step 3

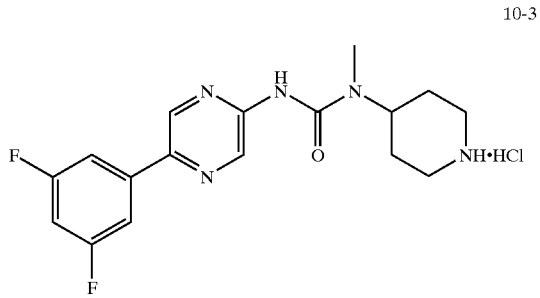
10-3

The product of Step 2 (2.50 g, 5.59 mmol) was treated with 4M HCl/1,4-dioxane (30 ml) by the procedure of Example 6, Step 4 to afford the product. $^1$H NMR (CD$_3$OD) δ 9.19 (s, b, 1H), 8.79 (s, b, 1H), 7.66 (m, 2H), 7.03 (m, 1H), 4.42–3.49 (m, 5H), 3.16 (m, 2H), 3.04 (s, 3H), 2.20–1.95 (m, 4H). MS m/e 348 (M+H)$^+$.

Step 4

To a mixture of the product of Step 3 (2.15 g, 5.59 mmol), and Et$_3$N (3.9 ml, 28.0 mmol) in CH$_2$Cl$_2$ (50 ml) was added acetic anhydride (0.58 ml, 6.15 mmol). The reaction mixture was stirred for 16 hr, then poured into water (100 ml). The whole was extracted with CH$_2$Cl$_2$ (3×200 ml), dried (Na$_2$SO$_4$), filtered, and evaporated. The residue was subjected to flash chromatography (gradient 1:100–5:95 MeOH/CH$_2$Cl$_2$) to give the product (1.71 g, 78%). $^1$H NMR (CDCl$_3$) δ 9.44 (d, J=1.2 Hz, 1H), 8.55 (d, J=1.6 Hz, 1H), 7.51 (m, 2H), 7.23 (s, 1H), 6.84 (m, 1H), 4.79 (m, 1H), 4.53 (m, 1H), 3.91 (m, 1H), 3.20 (m, 1H), 2.94 (s, 3H), 2.63 (m, 1H), 2.12 (s, 3H), 1.86–1.55 (m, 4H). MS m/e 390 (M+H)$^+$.

Use of the appropriate procedures afforded the following compounds:

| STRUCTURE | $^1$H NMR | MS (M + H)$^+$ |
| --- | --- | --- |
| 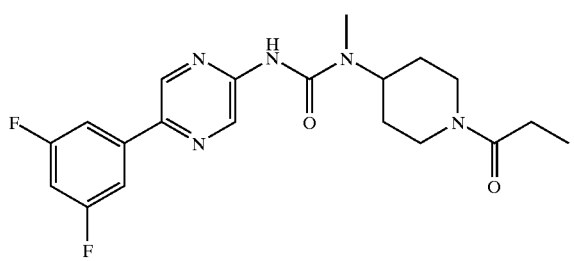<br>10A | (CDCl$_3$) δ 9.44 (bs, 1H), 8.55 (bs, 1H), 7.52 (m, 2H), 7.22 (s, 1H), 6.85 (m, 1H), 4.79 (m, 1H), 4.53 (m, 1H), 3.91 (m, 1H), 3.20 (m, 1H), 2.94 (s, 3H), 2.63 (m, 1H), 2.37 (m, 2H), 1.86–1.55 (m, 4H), 1.16 (m, 3H). | 404 |
| 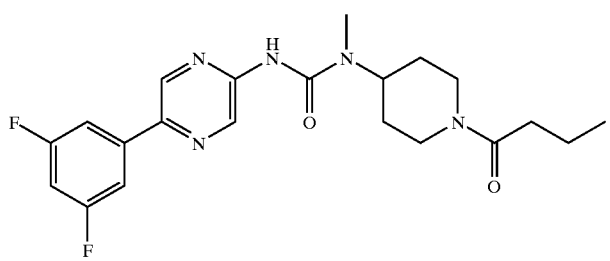<br>10B | (CDCl$_3$) δ 9.45 (bs, 1H), 8.56 (bs, 1H), 7.52 (m, 2H), 7.19 (s, 1H), 6.85 (m, 1H), 4.81 (m, 1H), 4.53 (m, 1H), 3.98 (m, 1H), 3.15 (m, 1H), 2.94 (s, 3H), 2.62 (m, 1H), 2.33 (m, 2H), 1.83–1.56 (m, 6H), 0.98 (m, 3H). | 418 |

-continued
| STRUCTURE | ¹H NMR | MS (M + H)⁺ |
|---|---|---|
| 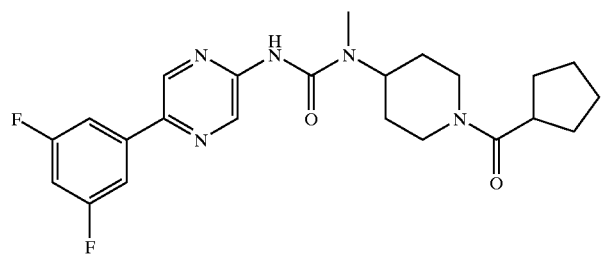<br>10C | (CDCl₃) δ 9.45 (bs, 1H), 8.56 (bs, 1H), 7.52 (m, 2H), 7.26 (s, 1H), 6.85 (t, 1H), 4.82 (b, 1H), 4.53 (m, 1H), 4.10 (b, 1H), 3.15 (t, 1H), 2.93 (m, 4H), 2.62 (t, 1H), 1.90–1.50 (m, 12H). | 444 |
| 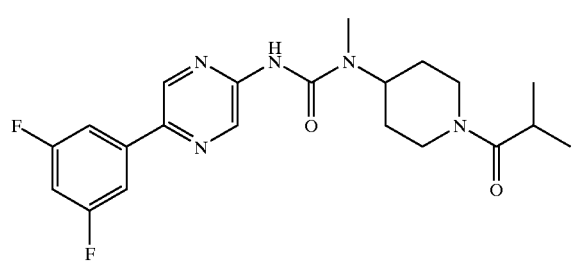<br>10D | (CDCl₃) δ 9.45 (d, J = 1.2 Hz, 1H), 8.56 (d, J = 1.2 Hz, 1H), 7.51 (m, 2H), 7.21 (s, 1H), 6.84 (m, 1H), 4.83 (m, 1H), 4.54 (m, 1H), 4.05 (m, 1H), 3.16 (m, 1H), 2.94 (s, 3H), 2.84 (m, 1H), 2.62 (m, 1H), 1.82 (m, 2H), 1.58 (m, 2H), 1.14 (m, 6H) | 418 |
| 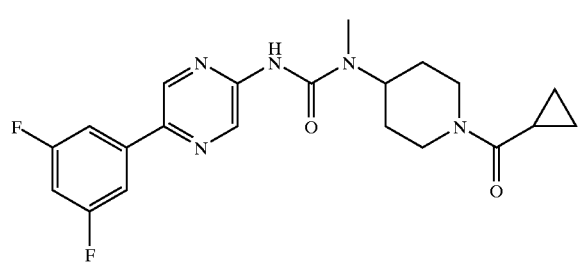<br>10E | (CDCl₃) δ 9.45 (d, J = 1.2 Hz, 1H), 8.56 (d, J = 1.2 Hz, 1H), 7.51 (m, 2H), 7.22 (s, 1H), 6.84 (m, 1H), 4.77 (m, 1H), 4.56 (m, 1H), 4.38 (m, 1H), 3.22 (m, 1H), 2.94 (s, 3H), 2.67 (m, 1H), 1.90–1.55 (m, 5H), 1.00 (m, 2H), 0.78 (m, 2H) | 416 |
| 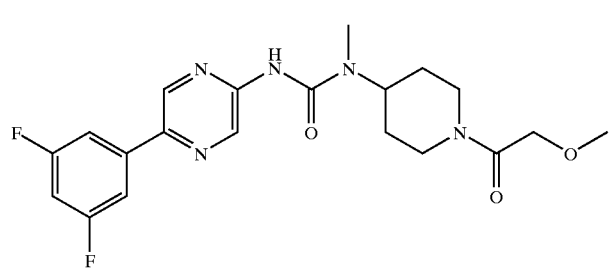<br>10F | (CDCl₃) δ 9.43 (d, J = 1.6 Hz, 1H), 8.55 (d, J = 1.6 Hz, 1H), 7.51 (m, 2H), 7.28 (s, 1H), 6.84 (m, 1H), 4.76 (m, 1H), 4.56 (m, 1H), 4.11 (q, 2H), 4.02 (m, 1H), 3.43 (s, 3H), 3.17 (m, 1H), 2.93 (s, 3H), 2.68 (m, 1H), 1.95–1.57 (m, 4H) | 420 |
| 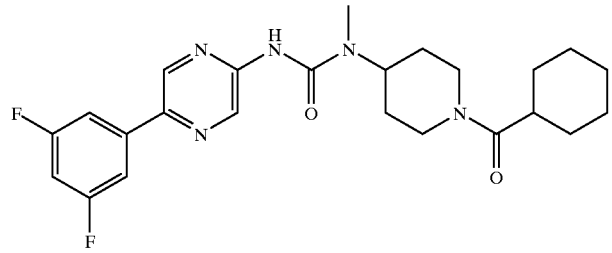<br>10G | (CDCl₃) δ 9.45 (d, J = 1.6 Hz, 1H), 8.55 (d, J = 1.2 Hz, 1H), 7.51 (m, 2H), 7.24 (s, 1H), 6.84 (m, 1H), 4.82 (m, 1H), 4.53 (m, 1H), 4.03 (m, 1H), 3.15 (m, 1H), 2.93 (s, 3H), 2.61 (m, 1H), 2.49 (m, 1H), 1.95–1.20 (m, 14H) | 458 |

-continued

| STRUCTURE | ¹H NMR | MS (M + H)⁺ |
|---|---|---|
| 10H | (CDCl₃) δ 9.44 (d, J = 1.6 Hz, 1H), 8.55 (d, J = 1.6 Hz, 1H), 7.51 (m, 2H), 7.23 (s, 1H), 6.84 (m, 1H), 4.82 (m, 1H), 4.53 (m, 1H), 4.00 (m, 1H), 3.15 (m, 1H), 2.93 (s, 3H), 2.61 (m, 1H), 2.23 (m, 2H), 2.14 (m, 1H), 1.90–1.50 (m, 4H), 0.98 (m, 6H) | 432 |
| 10I | (CDCl₃) δ 9.44 (s, 1H), 8.55 (s, 1H), 7.51 (m, 2H), 7.25 (s, 1H), 6.84 (m, 1H), 4.85 (m, 1H), 4.53 (m, 1H), 4.05 (m, 1H), 3.17 (m, 1H), 2.93 (s, 3H), 2.61 (m, 1H), 2.28 (q, 2H), 1.90–1.50 (m, 4H), 1.04 (m, 9H) | 446 |
| 10J | (CDCl₃) δ 9.42 (d, J = 1.6 Hz, 1H), 8.53 (d, J = 1.6 Hz, 1H), 7.49 (m, 2H), 7.32 (s, 1H), 6.83 (m, 1H), 4.82 (m, 1H), 4.57 (m, 1H), 3.97 (m, 1H), 3.18 (m, 1H), 2.93 (s, 3H), 2.62 (m, 1H), 2.30 (m, 2H), 1.85–1.50 (m, 4H), 1.03 (m, 1H), 0.57 (m, 2H), 0.17 (m, 2H) | 430 |
| 10K | (CDCl₃) δ 9.45 (s, 1H), 8.55 (s, 1H), 7.51 (m, 2H), 7.24 (s, 1H), 6.83 (m, 1H), 4.55 (m, 3H), 2.93 (m, 3H), 2.84 (m, 2H), 1.90–1.50 (m, 4H), 1.29 (s, 9H) | 432 |
| 10L | (CDCl₃) δ 9.44 (d, J = 1.6 Hz, 1H), 8.55 (d, J = 1.6 Hz, 1H), 7.49 (m, 2H), 7.45 (m, 1H), 7.31 (m, 1H), 7.28 (s, 1H), 7.05 (m, 1H), 6.84 (m, 1H), 4.62 (m, 3H), 3.08 (m, 2H), 2.97 (s, 3H), 1.90–1.60 (m, 4H) | 458 |

-continued

| STRUCTURE | ¹H NMR | MS (M + H)⁺ |
|---|---|---|
| 10M | (CDCl₃) δ 9.44 (d, J = 1.6 Hz, 1H), 8.55 (d, J = 1.6 Hz, 1H), 7.52 (m, 2H), 7.42 (m, 5H), 7.26 (s, 1H), 6.85 (m, 1H), 4.90 (bs, 1H), 4.78 (m, 1H), 3.90 (bs, 1H), 3.15 (m, b, 1H), 2.97 (s, 3H), 2.87 (bs, 1H), 2.90–1.50 (m, b, 4H) | 452 |
| 10N | (CDCl₃) δ 9.45 (d, J = 1.6 Hz, 1H), 8.55 (d, J = 1.2 Hz, 1H), 7.51 (m, 2H), 7.22 (s, 1H), 6.85 (m, 1H), 4.82 (b, 1H), 4.58 (m, 1H), 4.07 (b, 1H), 3.17 (m, 1H), 2.94 (s, 3H), 2.75 (m, 1H), 2.61 (m, 1H), 1.90–1.50 (m, 5H), 1.38 (m, 3H), 1.12 (m, 3H), 0.92 (m, 3H) | 446 |
| 10O | (CDCl₃) δ 9.44 (d, J = 1.2 Hz, 1H), 8.55 (s, 1H), 7.51 (m, 2H), 7.22 (s, 1H), 6.85 (m, 1H), 4.78 (m, 1H), 4.52 (m, 1H), 3.81 (m, 1H), 3.27 (m, 1H), 3.08 (m, 1H), 2.92 (s, 3H), 2.65 (m, 1H), 2.34 (m, 2H), 2.16 (m, 2H), 2.10–1.40 (m, 6H) | 430 |
| 10P | (CDCl₃) δ 9.44 (s, 1H), 8.55 (s, 1H), 7.51 (m, 2H), 7.28 (s, 1H), 6.83 (m, 1H), 4.92 (b, 1H), 4.55 (m, 1H), 4.15 (b, 1H), 3.17 (m, 1H), 2.92 (s, 3H), 2.62 (m, 1H), 2.54 (m, 1H), 1.90–1.40 (m, 8H), 0.87 (m, 6H) | 446 |
| 10Q | (CDCl₃) δ 9.42 (d, J = 1.6 Hz, 1H), 8.68 (bs, 2H), 8.55 (d, J = 1.6 Hz, 1H), 7.76 (m, 1H), 7.51 (m, 2H), 7.38 (m, 1H), 7.28 (s, 1H), 6.83 (m, 1H), 4.90 (bs, 1H), 3.25 (bs, 1H), 2.97 (s, 3H), 2.90 (bs, 1H), 2.00–1.50 (m, b, 4H) | 453 |

-continued
| STRUCTURE | ¹H NMR | MS (M + H)⁺ |
|---|---|---|
| 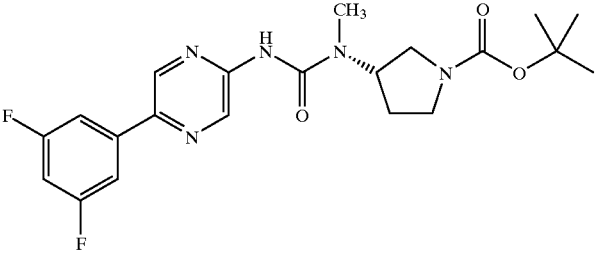<br>10R | ¹HNMR (CDCl₃) δ 9.44 (d, 1H), 8.62 (bs, 1H), 8.55 (d, 1H), 7.51 (m, 2H), 6.84 (m, 1H), 5.06 (m, 1H), 3.70–3.10 (m, 4H), 3.01 (s, 3H), 2.12 (m, 1H), 1.98 (m, 1H), 1.47 (s, 9H). | 434 |
| 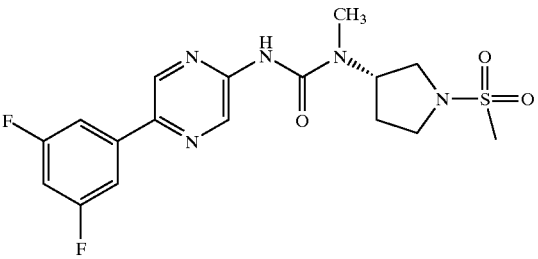<br>10S | (CDCl₃) δ 9.42 (s, 1H), 8.58 (s, 1H), 7.52 (m, 2H), 7.24 (s, 1H), 6.85 (m, 1H), 5.16 (m, 1H), 3.67 (m, 1H), 3.51 (m, 1H), 3.37 (m, 1H), 3.25 (m, 1H), 3.09 (s, 3H), 2.89 (s, 3H), 2.26 (m, 1H), 2.10 (m, 1H) | 412 |
| 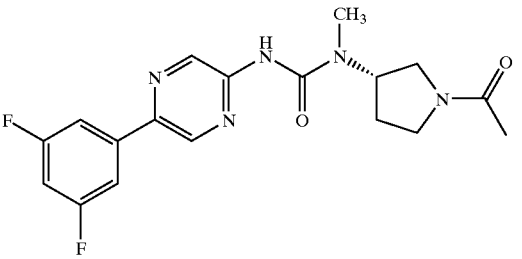<br>10T | (CDCl₃) δ 9.42 (s, 1H), 8.56 (m, 1H), 7.50 (m, 2H), 7.32 (d, 1H), 6.84 (m, 1H), 5.11 (m, 1H), 3.82–3.28 (m, 4H), 3.01 (d, 3H), 2.32–1.90 (m, 5H) | 376 |
| 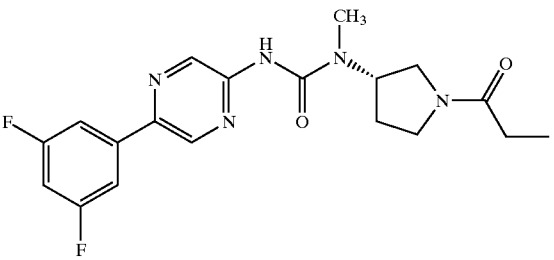<br>10U | (CDCl₃) δ 9.42 (s, 1H), 8.56 (m, 1H), 7.50 (m, 2H), 7.27 (d, 1H), 6.84 (m, 1H), 5.11 (m, 1H), 4.87–3.25 (m, 4H), 3.02 (d, 3H), 2.40–1.90 (m, 4H), 1.15 (m, 3H) | 390 |
| 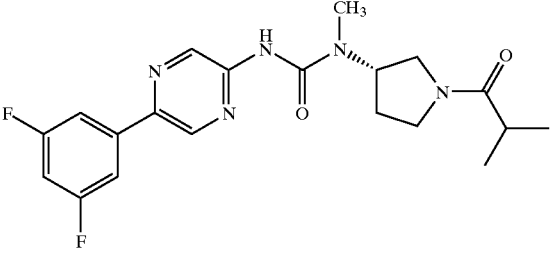<br>10V | (CDCl₃) δ 9.43 (s, 1H), 8.57 (bs, 1H), 7.51 (m, 2H), 2.27 (s, 1H), 6.83 (m, 1H), 5.09 (m, 1H), 3.90–3.30 (m, 4H), 3.03 (d, 3H), 2.65 (m, 1H), 2.30–1.90 (m, 2H), 1.14 (m, 6H) | 404 |

| STRUCTURE | ¹H NMR | MS (M + H)⁺ |
|---|---|---|
| 10W | (CDCl₃) δ 9.44 (s, 1H), 8.56 (s, 1H), 7.52 (m, 2H), 7.25 (s, 1H), 6.85 (m, 1H), 4.43 (m, 1H), 3.94 (b, 2H), 2.98 (s, 3H), 2.81 (m, 5H), 1.84 (m, 4H) | 426 |
| 10X | (CDCl₃) δ 9.42 (s, 1H), 8.58 (s, 1H), 7.71 (m, 2H), 7.42 (m, 1H), 7.19 (s, 1H), 7.10 (m, 1H), 4.42 (m, 1H), 3.92 (m, 2H), 2.97 (s, 3H), 2.80 (s, 5H), 1.83 (m, 4H). | 408 |
| 10Y | (CDCl₃) δ 9.42 (d, J = 1.6 Hz, 1H), 8.57 (s, 1H), 7.72 (m, 2H), 7.42 (m, 1H), 7.24 (s, 1H), 7.08 (m, 1H), 4.79 (m, 1H), 4.53 (m, 1H), 3.91 (m, 1H), 3.19 (m, 1H), 2.93 (s, 3H), 2.62 (m, 1H), 2.12 (s, 3H), 1.90–1.50 (M, 4H) | 372 |
| 10Z | (CDCl₃) δ 9.44 (d, J = 1.6 Hz, 1H), 8.57 (d, J = 1.6 Hz, 1H), 7.71 (m, 2H), 7.46 (m, 1H), 7.25 (s, 1H), 7.10 (m, 1H), 4.90 (b, 1H), 4.53 (m, 1H), 3.95 (b, 1H), 3.14 (m, 1H), 2.93 (s, 3H), 2.61 (m, 1H), 2.37 (q, 2H), 1.90–1.50 (m, 4H), 1.16 (t, 3H) | 386 |
| 10AA | (CDCl₃) δ 9.44 (d, J = 1.6 Hz, 1H), 8.58 (d, J = 1.2 Hz, 1H), 7.71 (m, 2H), 7.43 (m, 1H), 7.19 (s, 1H), 7.11 (m, 1H), 4.93 (b, 1H), 4.58 (m, 1H), 4.08 (b, 1H), 3.18 (m, 1H), 2.94 (s, 3H), 2.82 (m, 1H), 2.63 (m, 1H), 1.90–1.50 (m, 4H), 1.14 (m, 6H) | 400 |

| STRUCTURE | ¹H NMR | MS (M + H)⁺ |
|---|---|---|
| 10BB | (CDCl₃) δ 9.45 (s, 1H), 8.59 (s, 1H), 7.72 (m, 2H), 7.45 (m, 1H), 7.20 (s, 1H), 7.11 (m, 1H), 4.78 (m, 1H), 4.58 (m, 1H), 4.37 (b, 1H), 3.24 (m, 1H), 2.95 (s, 3H), 2.88 (m, 1H), 1.90–1.50 (m, 5H), 0.99 (m, 2H), 0.78 (m, 2H) | 398 |
| 10CC | (CDCl₃) δ 9.48 (d, J = 1.6 Hz, 1H), 8.72 (d, J = 1.6 Hz, 1H), 7.79 (m, 1H), 7.21 (s, 1H), 7.15 (m, 1H), 7.07 (m, 1H), 4.81 (b, 1H), 4.57 (m, 1H), 3.93 (b, 1H), 3.21 (t, 1H), 2.94 (s, 3H), 2.63 (t, 1H), 2.12 (s, 3H), 1.90–1.50 (m, 4H) | 390 |
| 10DD | (CDCl₃) δ 9.47 (d, J = 1.6 Hz, 1H), 8.71 (m, 1H), 7.78 (m, 1H), 7.27 (s, 1H), 7.15 (m, 1H), 7.07 (m, 1H), 4.81 (b, 1H), 4.57 (m, 1H), 3.95 (b, 1H), 3.15 (t, 1H), 2.93 (s, 3H), 2.63 (t, 1H), 2.37 (q, 2H), 1.90–1.50 (m, 4H), 1.16 (t, 3H) | 404 |
| 10EE | (CDCl₃) δ 9.48 (d, J = 1.6 Hz, 1H), 8.72 (m, 1H), 7.78 (m, 1H), 7.23 (s, 1H), 7.15 (m, 1H), 7.07 (m, 1H), 4.82 (b, 1H), 4.55 (m, 1H), 4.04 (b, 1H), 3.17 (b, 1H), 2.94 (s, 3H), 2.82 (m, 1H), 2.62 (b, 1H), 1.90–1.50 (m, 4H), 1.15 (m, 6H) | 418 |
| 10FF | (CDCl₃) δ 9.48 (d, J = 1.6 Hz, 1H), 8.71 (m, 1H), 7.78 (m, 1H), 7.31 (s, 1H), 7.15 (m, 1H), 7.07 (m, 1H), 4.78 (b, 1H), 4.55 (m, 1H), 4.35 (b, 1H), 3.15 (b, 1H), 2.94 (s, 3H), 2.65 (b, 1H), 1.90–1.50 (m, 5H), 0.98 (m, 2H), 0.77 (m, 2H) | 416 |

| STRUCTURE | ¹H NMR | MS (M + H)⁺ |
|---|---|---|
| 10GG | (CDCl₃) δ 9.48 (d, J = 1.2 Hz, 1H), 8.70 (m, 1H), 7.78 (m, 1H), 7.31 (s, 1H), 7.15 (m, 1H), 7.07 (m, 1H), 4.81 (b, 1H), 4.55 (m, 1H), 4.09 (b, 1H), 3.15 (b, 1H), 2.93 (s, 3H), 2.87 (m, 1H), 2.63 (b, 1H), 1.90–1.50 (m, 12H). | 444 |
| 10HH | (CDCl₃) δ 9.43 (d, J = 1.2 Hz, 1H), 8.57 (d, J = 1.2 Hz, 1H), 7.97 (d, J = 1.6 Hz, 1H), 7.83 (m, 1H), 7.40 (m, 2H), 7.22 (s, 1H), 4.78 (m, 1H), 4.53 (m, 1H), 3.90 (m, 1H), 3.19 (m, 1H), 2.93 (s, 3H), 2.62 (m, 1H), 2.12 (s, 3H), 1.79 (m, 2H), 1.59 (m, 2H) | 388 |
| 10II | (CDCl₃) δ 9.43 (d, J = 1.6 Hz, 1H), 8.57 (d, J = 1.6 Hz, 1H), 7.97 (m, 1H), 7.85 (m, 1H), 7.40 (m, 2H), 7.23 (s, 1H), 4.81 (m, 1H), 4.55 (m, 1H), 3.97 (b, 1H), 3.15 (b, 1H), 2.93 (s, 3H), 2.64 (b, 1H), 2.37 (q, 2H), 1.90–1.50 (m, 4H), 1.16 (t, 3H) | 402 |
| 10JJ | (CDCl₃) δ 9.42 (d, J = 1.6 Hz, 1H), 8.56 (d, J = 2.0 Hz, 1H), 7.95 (m, 1H), 7.81 (m, 1H), 7.39 (m, 2H), 7.21 (s, 1H), 4.81 (b, 1H), 4.55 (m, 1H), 4.05 (b, 1H), 3.17 (b, 1H), 2.92 (s, 3H), 2.81 (m, 1H), 2.61 (b, 1H), 1.78 (m, 2H), 1.59 (m, 2H), 1.12 (m, 6H) | 416 |
| 10KK | (CDCl₃) δ 9.44 (d, J = 1.2 Hz, 1H), 8.57 (d, J = 1.2 Hz, 1H), 7.97 (m, 1H), 7.82 (m, 1H), 7.39 (m, 2H), 7.22 (s, 1H), 4.78 (m, 1H), 4.55 (m, 1H), 4.35 (m, 1H), 3.23 (m, 1H), 2.94 (s, 3H), 2.86 (m, 1H), 1.90–1.50 (m, 5H), 0.99 (m, 2H), 0.78 (m, 2H) | 414 |

-continued
| STRUCTURE | $^1$H NMR | MS (M + H)$^+$ |
|---|---|---|
| 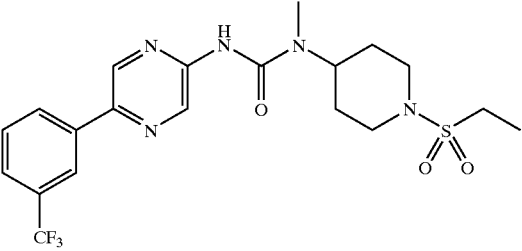<br>10LL | (CDCl$_3$) δ 9.46 (s, 1H), 8.64 (s, 1H), 8.24 (s, 1H), 8.14 (d, 1H), 7.63 (m, 2H), 7.20 (s, 1H), 4.48 (m, 1H), 3.97 (b, 2H), 2.98 (m, 7H), 1.81 (m, 4H), 1.37 (t, 3H) | 458 |
| 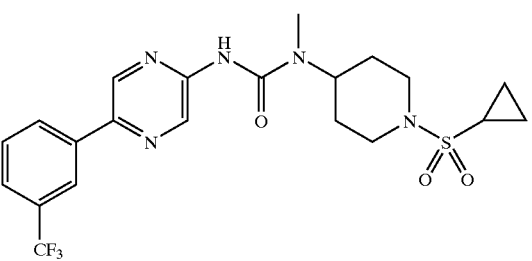<br>10MM | (CDCl$_3$) δ 9.46 (s, 1H), 8.64 (s, 1H), 8.24 (s, 1H), 8.14 (d, 1H), 7.61 (m, 2H), 7.21 (s, 1H), 4.45 (m, 1H), 3.93 (b, 2H), 2.98 (m, 5H), 2.28 (m, 1H), 1.82 (m, 4H), 1.19 (m, 2H), 0.99 (m, 2H) | 484 |
| 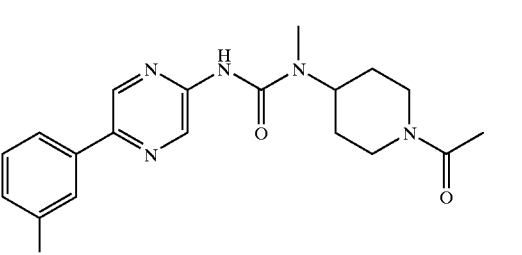<br>10NN | (CDCl$_3$) δ 9.48 (s, 1H), 8.63 (s, 1H), 8.24 (s, 1H), 8.17 (d, 1H), 7.63 (m, 2H), 7.24 (s, 1H), 4.79 (b, 1H), 4.57 (m, 1H), 3.92 (b, 1H), 3.12 (t, 1H), 2.95 (s, 3H), 2.63 (t, 1H), 2.13 (s, 3H), 1.90 (m, 2H), 1.82 (m, 2H) | 422 |
| 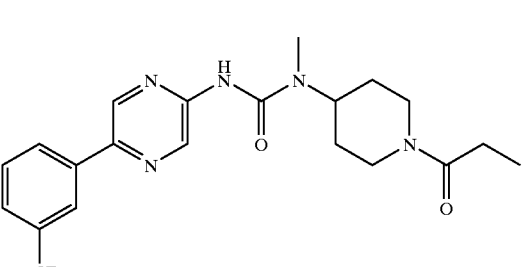<br>10OO | (CDCl$_3$) δ 9.47 (s, 1H), 8.63 (s, 1H), 8.24 (s, 1H), 8.17 (d, 1H), 7.63 (m, 2H), 7.21 (s, 1H), 4.83 (b, 1H), 4.55 (m, 1H), 3.98 (b, 1H), 3.18 (t, 1H), 2.94 (s, 3H), 2.63 (t, 1H), 2.38 (q, 2H), 1.90–1.50 (m, 4H), 1.16 (t, 3H) | 436 |
| 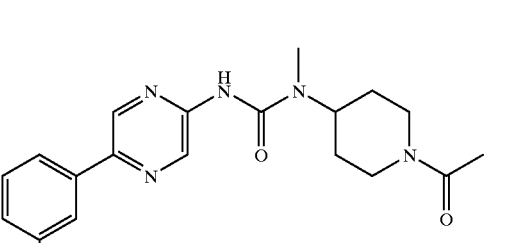<br>10PP | (CDCl$_3$) δ 9.47 (s, 1H), 8.63 (s, 1H), 8.24 (s, 1H), 8.15 (d, 1H), 7.62 (m, 2H), 7.22 (s, 1H), 4.83 (b, 1H), 4.58 (m, 1H), 4.05 (b, 1H), 3.19 (t, 1H), 2.94 (s, 3H), 2.82 (m, 1H), 2.63 (b, 1H), 1.90–1.50 (m, 4H), 1.14 (m, 6H) | 450 |

| STRUCTURE | ¹H NMR | MS (M + H)⁺ |
|---|---|---|
| 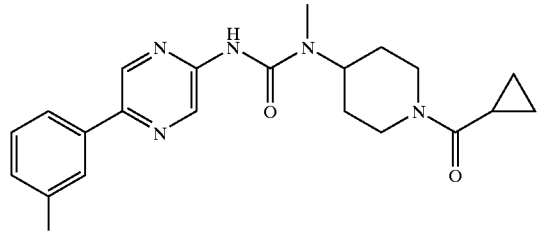<br>10QQ | (CDCl₃) δ 9.48 (s, 1H), 8.63 (s, 1H), 8.24 (s, 1H), 8.15 (d, 1H), 7.62 (m, 2H), 7.22 (s, 1H), 4.79 (b, 1H), 4.58 (m, 1H), 4.37 (b, 1H), 3.22 (b, 1H), 2.95 (s, 3H), 2.67 (b, 1H), 2.90–1.50 (m, 5H), 0.99 (m, 2H), 0.78 (m, 2H) | 448 |
| 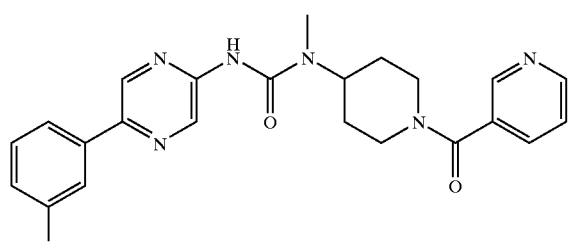<br>10RR | (CDCl₃) δ 9.46 (d, J = 1.2 Hz, 1H), 8.71 (bs, 2H), 8.63 (s, J = 1.2 Hz, 1H), 8.24 (s, 1H), 8.15 (d, J = 8.0 Hz, 1H), 7.78 (d, J = 7.6 Hz, 1H), 7.67 (d, J = 8.4 Hz, 1H), 7.60 (t, J = 8.0 Hz, 1H), 7.39 (m, b, 1H), 7.29 (s, 1H), 4.90 (bs, 1H), 4.62 (m, 1H), 3.83 (bs, 1H), 3.23 (bs, 1H), 2.99 (s, 3H), 2.90 (bs, 1H), 1.90–1.50 (m, 4H) | 485 |

EXAMPLE 11

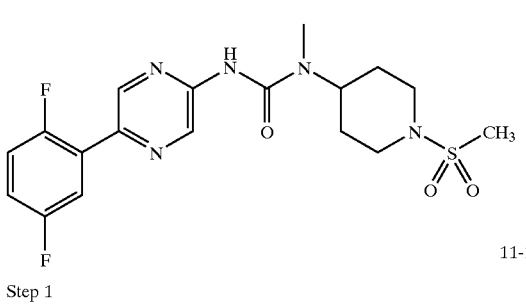

Step 1.

Reaction of 2-amino-5-bromopyrazine and Preparation 11 by the procedure of Example 10, Step 2 gave the product. ¹HNMR (CDCl₃) δ 9.18 (d, J=1.2 Hz, 1H), 8.26 (d, J=1.2 Hz, 1H), 7.11 (s, 1H), 4.42 (m, 1H), 3.93 (m, 2H), 2.95 (s, 3H), 2.79 (m, 5H), 1.81 (m, 4H). MS m/e 394 (M+H)⁺.

Step 2.

A flask charged with 11-1 (0.090 g, 0.23 mmol), 2,5-difluorophenylboronic acid (0.044 g, 0.28 mmol), toluene (10 ml), water (0.3 ml) and cesium carbonate (0.082 g, 0.25 mmol) was purged with N₂. PdCl₂(dppf)₂CH₂Cl₂ (0.015 g, 0.019 mmol) was added and the reaction mixture was refluxed for 3 hr, allowed to cool, and filtered. The concentrated filtrate was subjected to PTLC (1:1 acetone/hexane) to give the product (0.046 g, 47%). ¹H NMR (CDCl₃) δ 9.47 (d, J=1.6 Hz, 1H), 8.72 (m, 1H), 7.78 (m, 1H), 7.22 (s, 1H), 7.15 (m, 1H), 7.06 (m, 1H), 4.48 (m, 1H), 3.95 (m, 2H), 2.98 (s, 3H), 2.83 (m, 5H), 1.86 (m, 4H). MS m/e 426 (M+H)⁺.

Use of the appropriate boronic acid and essentially the same procedure afforded the following compounds:

| STRUCTURE | ¹H NMR | MS (M + H)⁺ |
|---|---|---|
| 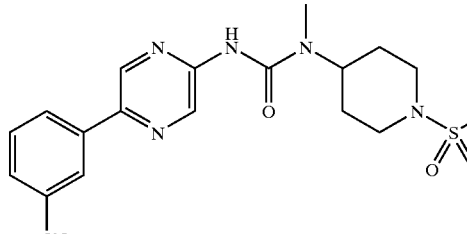<br>11A | (CDCl₃) δ 9.46 (s, 1H), 8.62 (s, 1H), 8.29 (s, 1H), 8.20 (m, 1H), 7.69 (m, 1H), 7.60 (m, 1H), 7.22 (m, 1H), 4.44 (m, 1H), 3.95 (m, 2H), 2.98 (s, 3H), 2.81 (m, 5H), 1.83 (m, 4H). | 415 |

| STRUCTURE | ¹H NMR | MS (M + H)⁺ |
|---|---|---|
| 11B | (CDCl₃) δ 9.43 (s, 1H), 8.59 (s, 1H), 7.80 (s, 1H), 7.75 (d, 1H), 7.37 (t, 1H), 7.25 (d, 1H), 7.16 (s, 1H), 4.50 (m, 1H), 3.95 (b, 2H), 2.97 (s, 3H), 2.82 (m, 5H), 2.44 (s, 3H), 1.84 (m, 4H) | 404 |
| 11C | (CDCl₃) δ 9.42 (d, J = 1.6 Hz, 1H), 8.59 (s, 1H), 7.52 (m, 2H), 7.39 (t, 1H), 7.16 (s, 1H), 6.97 (m, 1H), 4.48 (m, 1H), 3.94 (b, 2H), 3.89 (s, 3H), 2.97 (s, 3H), 2.81 (m, 5H), 1.84 (m, 4H) | 420 |
| 11D | (CDCl₃) δ 9.47 (s, 1H), 8.64 (s, 1H), 8.24 (s, 1H), 8.14 (d, 1H), 7.63 (m, 2H), 7.26 (s, 1H), 4.49 (bs, 1H), 3.94 (b, 2H), 2.98 (s, 3H), 2.81 (bs, 5H), 1.85 (bs, 4H) | 458 |
| 11E | (CDCl₃) δ 9.42 (s, 1H), 8.60 (s, 1H), 7.98 (s, 1H), 7.84 (m, 1H), 7.40 (m, 2H), 7.19 (s, 1H), 4.42 (m, 1H), 3.90 (m, 2H), 2.97 (s, 3H), 2.81 (m, 5H), 1.84 (m, 4H). | 424 |

EXAMPLE 12

Step 1

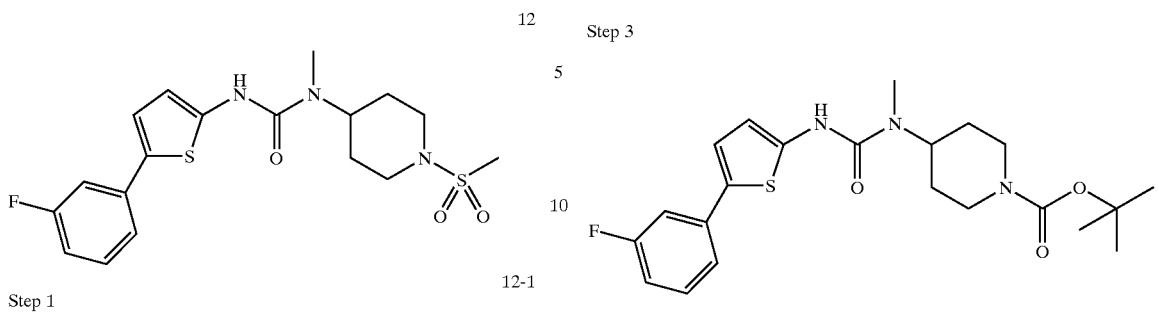

12-1

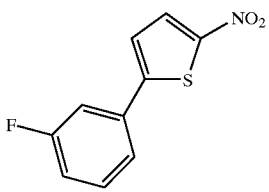

Reaction of 3-fluorophenylboronic acid with 2-bromo-5-nitrothiophene by essentially the procedure of Example 1, Step 1 gave the product. $^1$H NMR (CDCl$_3$, 400 MHz) δ 7.91 (1H, m), 7.42 (2H, m), 7.32 (1H, m), 7.25 (1H, m), 7.14 (1H, m).

Step 2

12-2

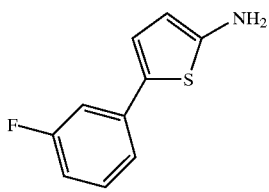

Reaction of the product of Step 1 with NiCl$_2$.6H$_2$O and NaBH$_4$ by essentially the procedure of Example 2, Step 2 gave the product. $^1$H NMR (CDCl$_3$, 400 MHz) δ 7.25 (2H, m), 7.14 (1H, m), 6.48 (1H, d, J=2 Hz), 6.85 (1H, m), 6.15 (1H, d, J=2 Hz), 3.87 (2H, b).

Step 3

12-3

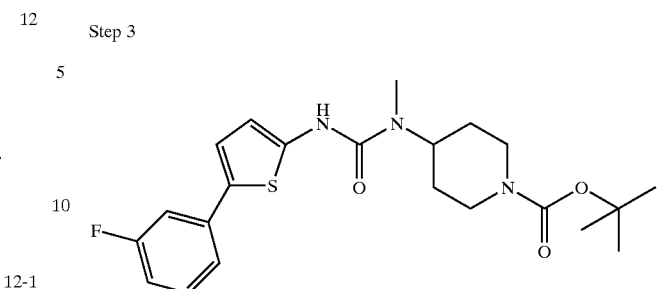

Reaction of the product of Step 2 with N,N'-disuccinimidyl carbonate and Preparation 1 by the procedure of Example 2, Step 3 gave the product. $^1$H NMR (CDCl$_3$, 400 MHz) δ 7.25 (3H, m), 7.06 (1H, m), 7.05 (1H, d, J=4 Hz), 6.89 (1H, m), 6.50 (1H, d, J=4 Hz), 4.44 (1H, m), 4.22 (2H, m), 2.86 (3H, s), 2.79 (2H, m), 1.60 (4H, m) 1.47 (9H, s). MS m/e 434 (M+H)$^+$.

Step 4

12-4

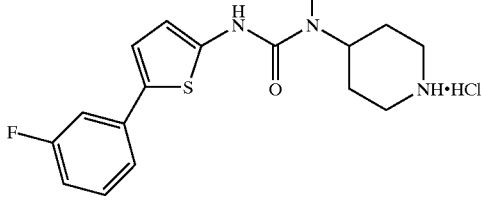

Reaction of the product of Step 3 with HCl by essentially the procedure of Example 6, Step 4 gave the product. $^1$H NMR (CD$_3$OD, 400 MHz) δ 7.36–7.24 (4H, m), 6.90 (1H, m), 6.73 (1H, m), 4.37 (1H, m), 3.50 (2H, m), 3.13 (2H, m), 2.96 (3H, s), 2.09–1.91 (4H, m).

Step 5

Reaction of the product of Step 4 with methanesulfonyl chloride by essentially the procedure of Example 3, Step 3 gave the product. $^1$H NMR (CDCl$_3$, 400 MHz) δ 7.45 (1H, s), 7.29 (3H, m), 7.05 (1H, d, J=4 Hz), 6.88 (1H, m), 6.54 (1H, d, J=4 Hz), 4.40 (1H, m), 3.86 (2H, m), 2.87 (3H, s), 2.74 (3H, s), 2.68 (2H, m), 1.76 (4H, m). MS m/e 412 (M+H)$^+$.

Use of the appropriate reagents and procedures afforded the following compounds.

| STRUCTURE | $^1$H NMR | MS (M + H)$^+$ |
|---|---|---|
|  12A | | 430 |

| STRUCTURE | ¹H NMR | MS (M + H)⁺ |
|---|---|---|
| 12B | | 444 |
| 12C | | 484 |
| 12D | (CDCl₃) δ 7.46 (1H, s), 7.28 (3H, m), 7.03 (1H, s), 6.86 (1H, m), 6.51 (1H, s), 4.74 (1H, m), 4.53 (1H, m), 3.85 (1H, m), 3.14 (1H, m), 2.86 (3H, s), 2.58 (1H, m), 2.10 (3H, s), 1.78 (2H, m), 1.58 (2H, m) | 376 |
| 12E | (CDCl₃) δ 7.63 91H, s), 7.29 (3H, m), 7.03 (1H, d, J = 4 Hz), 6.87 (1H, m), 6.49 (1H, d, J = 4 Hz), 4.70 (1H, m), 4.52 (1H, m), 4.30 (1H, m), 3.15 (1H, m), 2.85 (3H, s), 2.61 (1H, m), 1.72 (3H, m), 1.58 (2H, m), 0.95 (2H, m), 0.74 (2H, m). | 402 |
| 12F | (CDCl₃) δ 8.66 (2H, m), 7.75 (1H, d, J = 7.6 Hz), 7.56 (1H, s), 7.38 (1H, m), 7.28 (3H, m), 7.07 (1H, d, J = 4 Hz), 6.87 (1H, m), 6.49 (1H, d, J = 4 Hz), 4.87 (1H, m), 4.57 (1H, m), 3.78 (1H, m), 3.17 (1H, m), 2.88 (3H, s), 2.84 (1H, m), 1.81–1.56 (4H, m). | 439 |

-continued
| STRUCTURE | ¹H NMR | MS (M + H)⁺ |
|---|---|---|
| 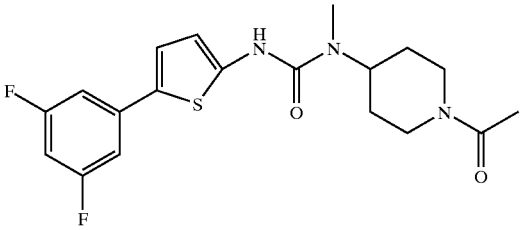<br>12G | (CDCl₃) δ 7.68 (s, 1H), 7.03 (m, 3H), 6.61 (m, 1H), 6.50 (m, 1H), 4.75 (m, 1H), 4.50 (m, 1H), 3.89 (m, 1H), 3.15 (m, 1H), 2.87 (s, 3H), 2.59 (m, 1H), 2.10 (s, 3H), 1.75 (m, 2H), 1.58 (m, 2H). | 394 |
| 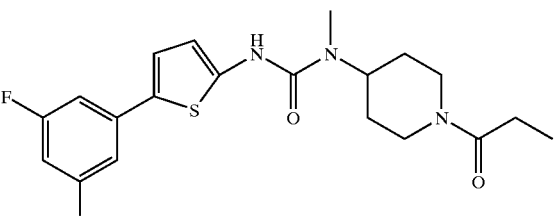<br>12H | (CDCl₃) δ 7.46 (s, 1H), 7.04 (m, 3H), 6.62 (m, 1H), 6.50 (m, 1H), 4.77 (m, 1H), 4.51 (m, 1H), 3.94 (m, 1H), 3.09 (m, 1H), 2.87 (s, 3H), 2.59 (m, 1H), 2.36 (q, J = 7.6 Hz, 2H), 1.75 (m, 2H), 1.57 (m, 2H), 1.15 (t, J = 7.6 Hz, 3H). | 408 |
| 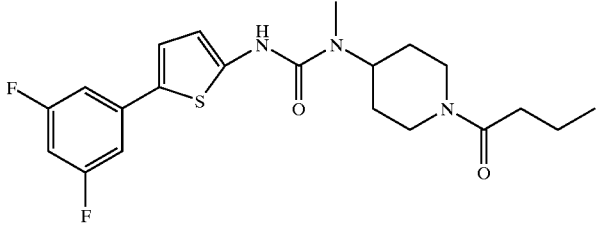<br>12I | (CDCl₃) δ 7.33 (s, 1H), 7.03 (m, 3H), 6.63 (m, 1H), 6.50 (m, 1H), 4.78 (m, 1H), 4.52 (m, 1H), 3.95 (m, 1H), 3.11 (m, 1H), 2.87 (s, 3H), 2.58 (m, 1H), 2.33 (m, 2H), 1.4–1.8 (m, 6H), 0.97 (t, J = 7.6 Hz, 3H). | 422 |
| 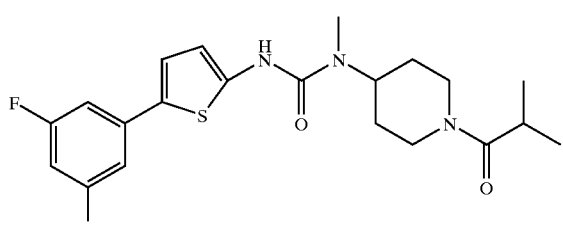<br>12J | (CDCl₃) δ 7.27 (s, 1H), 7.04 (m, 3H), 6.63 (m, 1H), 6.50 (m, 1H), 4.79 (m, 1H), 4.54 (m, 1H), 4.02 (m, 1H), 3.13 (m, 1H), 2.88 (s, 3H), 2.82 (m, 1H), 2.58 (m, 1H), 1.75 (m, 2H), 1.56 (m, 2H), 1.14 (m, 6H). | 422 |
| 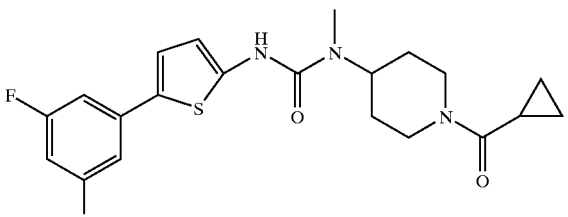<br>12K | (CDCl₃) δ 7.44 (b, 1H), 7.05 (m, 3H), 6.63 (m, 1H), 6.49 (m, 1H), 4.74 (m, 1H), 4.54 (m, 1H), 4.32 (m, 1H), 3.18 (m, 1H), 2.87 (s, 3H), 2.63 (m, 1H), 1.5–1.9 (m, 5H), 0.97 (m, 2H), 0.78 (m, 2H). | 420 |

-continued

| STRUCTURE | ¹H NMR | MS (M + H)⁺ |
|---|---|---|
| 12L | (CDCl₃) δ 7.26 (s, 1H), 7.04 (m, 3H), 6.63 (m, 1H), 6.50 (m, 1H), 4.73 (m, 1H), 4.54 (m, 1H), 4.11 (m, 2H), 3.97 (m, 1H), 3.43 (s, 3H), 3.10 (m, 1H), 2.88 (s, 3H), 2.64 (m, 1H), 1.77 (m, 2H), 1.60 (m, 2H). | 424 |
| 12M | (CDCl₃) δ 7.22 (m, 1H), 7.04 (m, 3H), 6.64 (m, 1H), 6.52 (m, 1H), 4.45 (m, 1H), 3.92 (m, 2H), 2.90 (s, 3H), 2.84 (m, 4H), 1.80 (m, 6H), 1.06 (t, J = 7.4 Hz, 3H). | 458 |
| 12N | (CDCl₃) δ 7.23 (m, 1H), 7.04 (m, 3H), 6.63 (m, 1H), 6.52 (m, 1H), 4.47 (m, 1H), 3.94 (m, 2H), 3.19 (m, 1H), 2.96 (m, 2H), 2.90 (s, 3H), 1.74 (m, 4H), 1.33 (d, J = 7.2 Hz, 6H). | 458 |

EXAMPLE 13

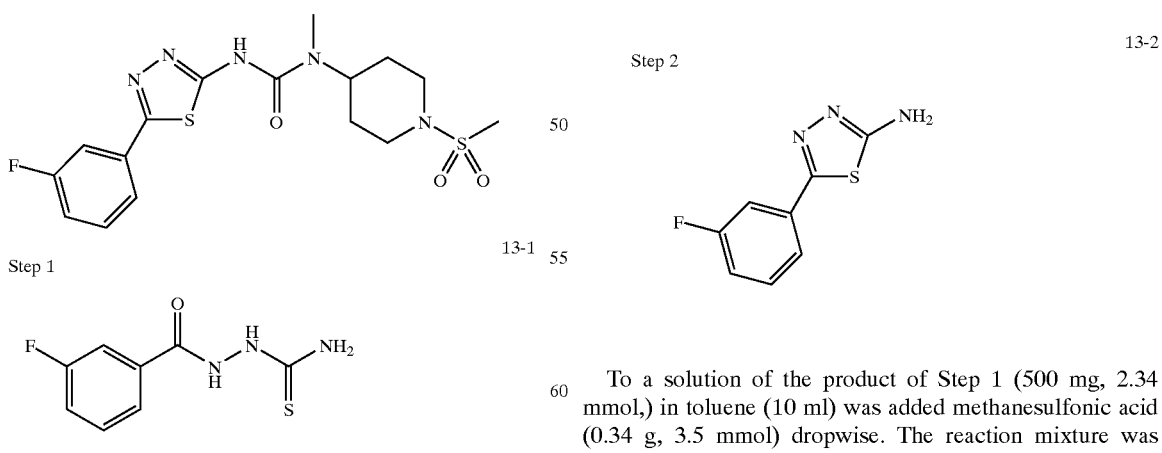

Step 1

To an ice-cold solution of 3-fluorobenzoyl chloride (2.0 g, 13 mmol) in pyridine (100 ml) was added thiosemicarbazide (0.96 g, 11 mmol) and the reaction mixture was allowed to warm to R.T. After stirring overnight, the pyridine was evaporated, the residue was taken up in water, and the precipitate was collected, washed with water, and air-dried to give the product (0.85 g, 32%). MS m/e 214 (M+H)⁺.

Step 2

To a solution of the product of Step 1 (500 mg, 2.34 mmol,) in toluene (10 ml) was added methanesulfonic acid (0.34 g, 3.5 mmol) dropwise. The reaction mixture was refluxed for 4 hr, cooled, and the precipitate was collected, washed with ether, and dried. The solid was then taken up in water, the solution was basified with ammonia to pH 8, and the precipitate was collected, washed with water, and dried to give the product (206 mg, 46%). MS m/e 196 (M+H)⁺.

Step 3

13-3

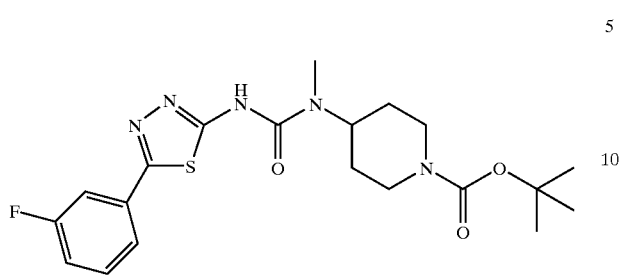

To a solution of the product of Step 2 (50 mg, 0.26 mmol) in CH$_2$Cl$_2$ (5 ml) was added Et$_3$N (0.1 ml, 0.8 mmol) followed by 4-nitrophenyl chloroformate (52 mg, 0.26 mmol). The reaction mixture was stirred for 1 hr, then Preparation 1 (55 mg, 0.26 mmol) was added, and the reaction mixture was stirred overnight. CH$_2$Cl$_2$ (10 ml) was added and the mixture was washed with 1N NaOH (3×), sat'd NaCl, dried (Na$_2$SO$_4$), filtered and evaporated. The residue was subjected to PTLC (5:95 MeOH/CH$_2$Cl$_2$) to give the product (48 mg, 42%). $^1$H NMR (CDCl$_3$, 400 MHz) δ 11.33 (1H, b), 7.63 (2H, m), 7.41 (1H, m), 7.16 (1H, m), 4.50 (1H, m), 4.23 (2H, b), 3.14 (3H, s), 2.79 (2H, b), 1.75 (4H, m), 1.46 (9H, s). MS m/e 436 (M+H)$^+$.

Step 4

Reaction of the product of Step 3 with HCl by essentially the procedure of Example 3, Step 2 gave the product.

13-4

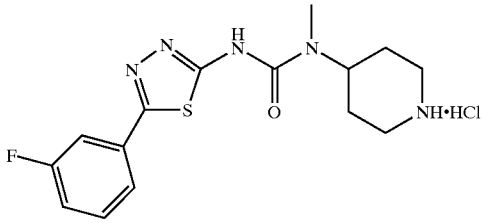

Step 5

Reaction of the product of Step 4 with methanesulfonyl chloride by essentially the procedure of Example 3, Step 3 gave the product. $^1$H NMR (CDCl$_3$, 400 MHz) δ 7.64 (2H, m), 7.48 (1H, m), 7.17 (1H, m), 4.44 (1H, m), 3.95 (2H, m), 3.06 (3H, s), 2.81 (3H, s), 2.80 (2H, m), 1.90 (4H, m). MS m/e 414 (M+H)$^+$.

EXAMPLE 14

14

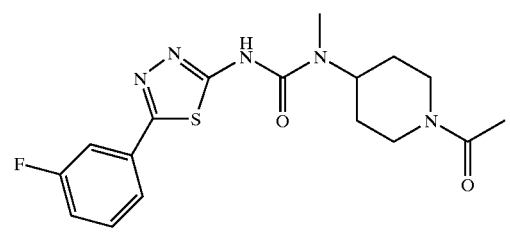

Reaction of the product of Example 13, Step 4 (13-4) with acetyl chloride by essentially the procedure of Example 4 gave the product. $^1$H NMR (CDCl$_3$, 400 MHz) δ 11.00 (1H, b), 7.65 (2H, m), 7.50 (1H, m), 7.17 (1H, m), 4.80 (1H, m), 4.55 (1H, m), 3.94 (1H, m), 3.20 (1H, m), 3.09 (3H, s), 2.63 (1H, m), 2.13 (3H, s), 1.70 (4H, m). MS m/e 378 (M+H)$^+$.

EXAMPLE 15

15

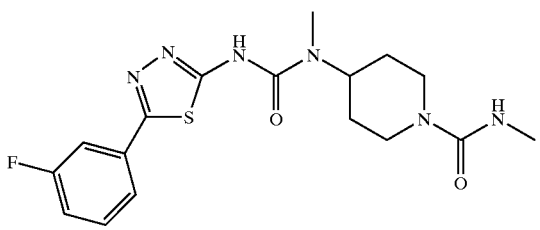

To an ice-cold solution of the product of Example 13, Step 4 (13-4) (25 mg, 0.074 mmol) in DMF (5 ml) was added methyl isocyanate (1 drop). The reaction mixture was allowed to warm to R.T., stirred for 3 days, then diluted with CH$_2$Cl$_2$ and washed with water, 1N NaOH, and sat'd NaCl. The organic layer was dried (Na$_2$SO$_4$), filtered and evaporated. The residue was subjected to PTLC (10:90 MeOH/CH$_2$Cl$_2$) to give the product (9 mg, 31%). $^1$H NMR (CDCl$_3$, 400 MHz) δ 10.80 (1H, b), 7.64 (2H, m), 7.45 (1H, m), 7.19 (1H, m), 4.48 (1H, m), 4.10 (2H, m), 3.10 (3H, s), 2.90 (3H, s), 2.85 (2H, m), 1.78 (4H, m). MS m/e 393 (M+H)$^+$.

EXAMPLE 16

Reaction of 12-4 with methyl isocyanate by essentially the same procedure gave the product. $^1$H NMR (CDCl$_3$, 400 MHz) δ 7.48 (1H, s), 7.28 (3H, m), 7.03 (1H, d, J=4 Hz), 6.87 (1H, m), 6.50 (1H, d, J=4 Hz), 4.56 (1H, m), 4.44 (1H, m), 4.03 (2H, m), 2.87 (2H, m), 2.86 (3H, s), 2.80 (3H, s), 2.04–1.54 (4H, m). MS m/e 392 (M+H)$^+$.

EXAMPLE 17

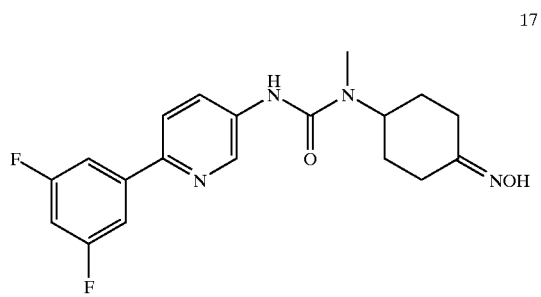

17

Step 1

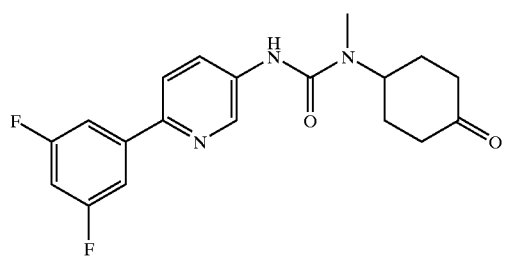

17-1

To a solution of the product of Example 1, Step 2 (1-2) (250 mg, 1.21 mmol) in toluene (8 ml) was added iPr₂NEt (1.1 ml, 6.0 mmol) and triphosgene (145 mg, 0.49 mmol). The reaction mixture was heated to 110° C. for 4 hr, cooled, and Preparation 13 (250 mg, 1.47 mmol) was added. The reaction mixture was stirred for 16 hr, then partitioned between CH₂Cl₂ (100 ml) and 1N NaOH (25 ml). The organic layer was washed with sat. NH₄Cl (25 ml) and sat'd NaCl (25 ml), dried (MgSO₄), filtered and concentrated. The residue was dissolved in THF (20 ml) to which 5N HCl (5 ml) was added. After 3.5 hr, the reaction mixture was cooled in an ice bath, basified to pH 12 and partitioned between CH₂Cl₂ (100 ml) and water (25 ml). The organic layer was dried (MgSO₄), filtered and concentrated. Subjection of the residue to PTLC (3:2 EtOAc/hexane) gave the product (130 mg, 30%). MS m/e 360 (M+H)⁺.

Step 2

To a solution of the product of Step 1 (60 mg, 0.17 mmol) in EtOH (2.5 ml) was added NaOAc (0.27 g, 3.3 mmol) and hydroxylamine hydrochloride (0.23 g, 3.34 mmol). The reaction mixture was stirred for 16 hr, then partitioned between CH₂Cl₂ (75 ml) and water (50 ml). The organic layer was dried (MgSO₄), filtered and concentrated. The residue was subjected to PTLC (3:97 MeOH/CH₂Cl₂) to give the product (52 mg, 83%). ¹H NMR (CD₃OD, 400 MHz) δ 8.69 (1H, m), 8.00 (1H, m), 7.80 (1H, m), 7.55 (4H, m), 6.94 (1H, m), 4.40 (1H, m), 3.45 (1H, m), 2.91 (3H, s), 2.50 (1H, m), 2.30 (1H, m), 1.90 (3H, m), 1.70 (2H, m). MS m/e 375 (M+H)⁺.

EXAMPLE 18

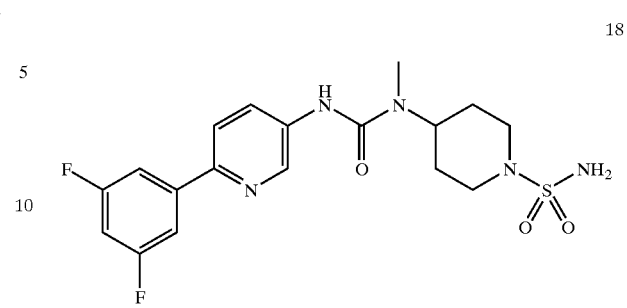

18

Reaction of the amine 1–2, N,N'-disuccinimidyl carbonate, and Preparation 12 by essentially the procedure of Example 2, Step 3 gave the product. ¹H NMR (DMSO, 400 MHz) δ 8.76 (1H, s), 8.66 (1H, s), 7.96 (2H, m), 7.73 (2H, d), 7.21 (1H, m), 6.77 (2H, s), 4.09 (1H, m), 3.55 (2H, m), 2.85 (3H, s), 2.61 (2H, m), 1.76 (2H, m), 1.64 (2H, m). MS m/e 426 (M+H)⁺.

EXAMPLE 19

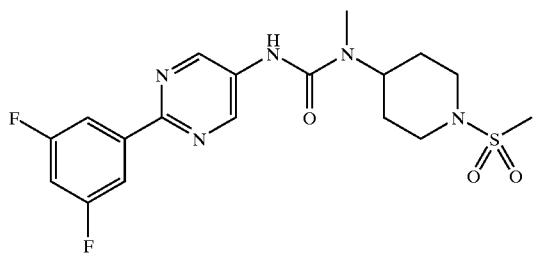

19

Step 1

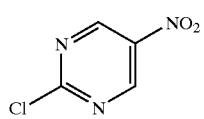

19-1

To a suspension of 2-amino-5-nitropyrimidine (2.70 g, 19.3 mmol) and LiCl (20 g) in 4M HCl (95 ml) at −10° C. was added NaNO₂ (2.70 g, 39.1 mmol) in portions. The suspension was stirred at ice-bath temperature for 1 hr, then allowed to warm to R.T. and stirred for 1.5 hr. The reaction mixture was cooled in an ice-bath, CH₂Cl₂ (50 ml) was added and aqueous layer was brought to pH 9 by addition of sat'd Na₂CO₃. The whole was filtered and the filtrate was extracted with CH₂Cl₂. The organic layer was dried (MgSO₄), filtered and evaporated to give a solid (1.05 g, 34%). ¹H NMR (CDCl₃, 400 MHz) δ 9.39 (s).

Step 2

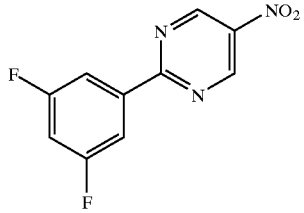

19-2

To an N₂-purged mixture of the product of Step 1 (230 mg, 1.44 mmol), 3,5-difluorophenylboronic acid (655 mg, 2.08 mmol), CsCO₃ (502 mg, 1.54 mmol), H₂O (0.05 ml), and toluene (3 ml) was added Pd(dppf)Cl₂·CH₂Cl₂ (82 mg, 0.10 mmol). The reaction mixture was heated at 110° C. for 1.5 hr, then allowed to cool. EtOAc (20 ml) and H₂O (20 ml) was added, and the organic layer was dried (MgSO₄), filtered and evaporated. Flash chromatography of the residue (1:99 EtOAc/hexanes) gave the product (110 mg, 32%). $^1$H NMR (CDCl₃, 400 MHz) δ 9.54 (2H, s), 8.08 (2H, m), 7.03 (1H, m).

Step 3

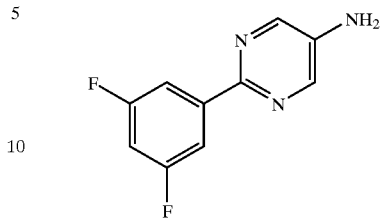

19-3

To an ice-cold suspension of the product of Step 2 (110 mg, 0.46 mmol) and NiCl₂·6H₂O (240 mg, 1.01 mmol) in MeOH (4 ml) was added NaBH₄ (57 mg, 1.51 mmol). The reaction mixture was stirred for 10 min., then H₂O (2 ml) was added and the mixture was concentrated. To the residue were added H₂O (20 ml) and CH₂Cl₂ (30 ml), and the whole was filtered. The organic layer of the filtrate was dried (Na₂SO₄), filtered and evaporated to give a solid (72 mg, 75%). MS (m/e) 208 (M+H)⁺.

Step 4

Reaction of the product of Step 3 (70 mg, 0.34 mmol) with Preparation 11 (98 mg, 0.51 mmol) by the procedure of Example 2, Step 3 gave the product (90 mg, 62%). $^1$H NMR (CDCl₃, 400 MHz) δ 8.91 (2H, s), 7.90 (2H, m), 6.86 (1H, m), 6.64 (1H, s), 4.42 (1H, m), 3.91 (2H, m), 2.95 (3H, s), 2.80 (5H, m), 1.81 (4H, m). MS (m/e) 426 (M+H)⁺.

Use of the appropriate procedures afforded the following compounds:

| STRUCTURE | $^1$H NMR | MS (M + H)⁺ |
|---|---|---|
| 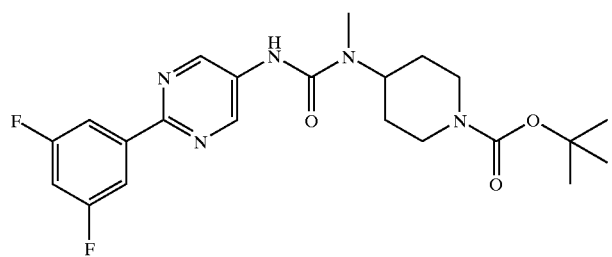<br>19A | (CDCl₃) δ 8.92 (s, 2H), 7.90 (m, 2H), 6.87 (m, 1H), 6.52 (s, 1H), 4.43 (m, 1H), 4.22 (m, 2H), 2.95 (s, 3H), 2.82 (m, 2H), 1.78–1.52 (m, 4H), 1.47 (s, 9H). | 448 |
| 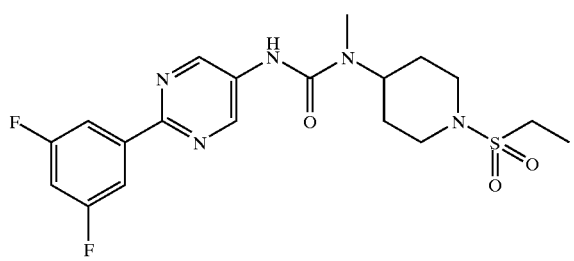<br>19B | (CDCl₃) δ 8.92 (s, 2H), 7.90 (m, 2H), 6.86 (m, 1H), 6.52 (s, 1H), 4.46 (m, 1H), 3.93 (m, 2H), 2.95 (m, 7H), 1.81 (m, 4H), 1.36 (t, 3H). | 440 |

| STRUCTURE | ¹H NMR | MS (M + H)⁺ |
|---|---|---|
| 19C | (CD₃OD) δ 8.99 (s, 2H), 7.91 (m, 2H), 7.04 (m, 1H), 4.28 (m, 1H), 3.86 (m, 2H), 2.95 (m, 7H), 1.84 (m, 6H), 1.07 (t, 3H). | 454 |
| 19D | (CDCl₃) δ 8.92 (s, 2H), 7.90 (m, 2H), 6.86 (m, 1H), 6.49 (s, 1H), 4.48 (m, 1H), 3.96 (m, 2H), 3.21 (m, 1H), 2.95 (m, 5H), 1.77 (m, 4H), 1.36 (m, 6H). | 454 |
| 19E | (CDCl₃) δ 8.92 (s, 2H), 7.91 (m, 2H), 6.87 (m, 1H), 6.63 (s, 1H), 4.44 (m, 1H), 3.90 (m, 2H), 2.95 (m, 5H), 2.28 (m, 1H), 1.82 (m, 4H), 1.15 (m, 2H), 1.00 (m, 2H). | 452 |
| 19F | (CDCl₃) δ 8.92 (s, 2H), 7.90 (m, 2H), 6.87 (m, 1H), 6.77 (s, 1H), 4.78 (m, 1H), 4.52 (m, 1H), 3.92 (m, 1H), 3.18 (m, 1H), 2.94 (s, 3H), 2.61 (m, 1H), 2.11 (s, 3H), 1.82–1.57 (m, 4H). | 390 |
| 19G | (CDCl₃) δ 8.92 (s, 2H), 7.90 (m, 2H), 6.87 (m, 1H), 6.74 (s, 1H), 4.78 (m, 1H), 4.52 (m, 1H), 3.95 (m, 1H), 3.12 (m, 1H), 2.93 (s, 3H), 2.61 (m, 1H), 2.38 (m, 2H), 1.82–1.55 (m, 4H), 1.35 (t, 3H). | 404 |

-continued

| STRUCTURE | ¹H NMR | MS (M + H)⁺ |
|---|---|---|
| 19H | (CDCl₃) δ 8.92 (s, 2H), 7.90 (m, 2H), 6.87 (m, 1H), 6.64 (s, 1H), 4.80 (m, 1H), 4.55 (m, 1H), 4.06 (m, 1H), 3.16 (m, 1H), 2.93 (s, 3H), 2.62 (m, 1H), 1.79–1.57 (m, 5H), 0.98 (m, 2H), 0.87 (m, 2H). | 416 |
| 19I | (CDCl₃) δ 8.92 (s, 2H), 7.90 (m, 2H), 6.87 (m, 1H), 6.64 (s, 1H), 4.81 (m, 1H), 4.53 (m, 1H), 4.06 (m, 1H), 3.16 (m, 1H), 2.94 (s, 3H), 2.80 (m, 1H), 2.59 (s, 1H), 1.79 (m, 2H), 1.57 (m, 2H), 1.14 (m, 6H). | 418 |
| 19J | (CD₃OD) δ 9.04 (s, 2H), 7.90 (m, 2H), 7.08 (m, 1H), 4.69 (m, 1H), 4.40 (m, 1H), 4.11 (m, 1H), 3.22 (m, 1H), 2.95 (s, 3H), 2.72 (m, 1H), 2.42 (t, 2H), 1.78–1.62 (m, 6H), 1.00 (t, 3H). | 418 |
| 19K | (CDCl₃) δ 8.92 (s, 2H), 8.69 (s, 2H), 7.91 (d, J = 6.8 Hz, 2H), 7.79 (s, J = 7.6 Hz, 1H), 7.40 (m, 1H), 6.87 (m, 1H), 6.56 (s, 1H), 4.87 (m, 1H), 4.60 (m, 1H), 3.87 (m, 1H), 3.24 (m, 1H), 2.98 (m, 4H), 1.95–1.48 (m, 4H). | 453 |
| 19L | (CDCl₃) δ 8.92 (s, 2H), 8.59 (m, 1H), 7.90 (m, 2H), 7.80 (m, 1H), 7.62 (d, J = 7.2 Hz, 1H), 7.36 (m, 1H), 6.87 (m, 1H), 6.70 (s, 1H), 4.89 (m, 1H), 4.60 (m, 1H), 4.09 (m, 1H), 3.16 (m, 1H), 2.96 (s, 3H), 2.88 (m, 1H), 1.84–1.72 (m, 4H). | 453 |

| STRUCTURE | $^1$H NMR | MS (M + H)$^+$ |
|---|---|---|
|  19M | (CDCl$_3$) δ 8.94 (s, 2H), 8.90 (s, 1H), 8.07 (s, 1H), 7.90 (m, 2H), 6.87 (m, 1H), 6.59 (s, 1H), 4.80–4.20 (m, 3H), 3.30–2.80 (m, 5H), 1.86–1.69 (m, 4H). | 459 |

EXAMPLE 20

20

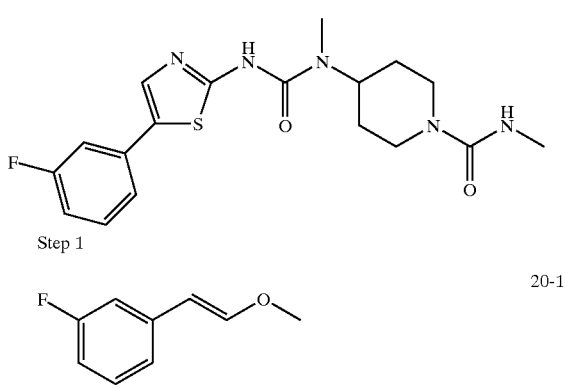

Step 1

20-1

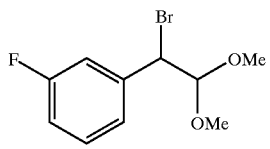

To an ice-cold suspension of (methoxymethyl)triphenylphosphonium chloride (30.4 g, 89 mmol) in Et$_2$O (250 ml) was added 1.8 M phenyllithium (49.3 ml, 89 mmol) dropwise under N$_2$. After the addition was complete, the reaction mixture was stirred at 0° C. for 0.25 hr, then at R.T. for 0.5 hr. The reaction mixture was cooled to −10° C. and 3-fluorobenzaldehyde (10 g, 81 mmol) was added dropwise. The reaction mixture was stirred at R.T. overnight, then sat'd NH$_4$Cl was added. The aqueous layer was extracted with Et$_2$O (2×), and the combined organic layers were dried (Na$_2$SO$_4$), filtered, and concentrated. Flash chromatography (hexane) of the residue afforded the product (8.67 g, 70%) as a mixture of isomers. $^1$H NMR (CDCl$_3$, 400 MHz, major isomer) δ 7.36 (1H, m), 7.32 (1H, m), 7.07 (1H, d, J=17 Hz), 6.96 (1H, m), 6.93 (1H, m), 5.77 (1H, d, J=17 Hz), 3.70 (3H, s).

Step 2

20-2

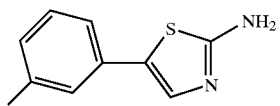

To an ice-cold solution of the product of Step 1 (8.67, 57 mmol) in MeOH (200 ml) was added N-bromosuccinimide (10.14 g, 57 mmol), and the reaction mixture was stirred at R.T. for 16 hr. The reaction mixture was concentrated, taken up in EtOAc, washed with 1M HCl and sat'd NaCl, then dried (Na$_2$SO$_4$), filtered and concentrated. Subjection of the residue to flash chromatography (90:10 hexane/EtOAc) gave the product (11.8 g, 80%). $^1$H NMR (CDCl$_3$, 400 MHz) δ7.32 (1H, m), 7.16 (2H, m), 6.99 (1H, m), 4.90 (1H, d, J=9 Hz), 4.70 (1H, d, J=9 Hz), 3.49 (3H, s), 3.31 (3H, s).

Step 3

20-3

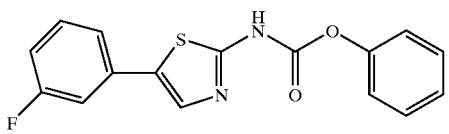

A mixture of the product of Step 2 (11.5 g, 43.7 mmol), thiourea (6.0 g, 79 mmol) and 48% HBr (0.1 ml) was stirred at 100° C. for 3 hr. The reaction mixture was allowed to cool to R.T., acidified with 6N HCl, and washed with CH$_2$Cl$_2$. The aqueous layer was brought to pH 9 by addition of aqueous NH$_4$OH and the resultant precipitate was collected. Subjection of the dried precipitate to flash chromatography (2:98 then 5:95 MeOH/CH$_2$Cl$_2$) gave the product (1.61 g, 19%). $^1$H NMR (CDCl$_3$, 400 MHz) δ 7.30 (2H, m), 7.18 (1H, m), 7.11 (1H, m), 6.93 (1H, m), 5.07 (2H, b).

Step 4

20-4

To a stirred suspension of NaH (103 mg, 2.6 mmol, 60% dispersion) in THF (30 ml) under N$_2$ was added the product of Step 3 (500 mg, 2.6 mmol). After 1 hr, the reaction mixture was cooled in an ice bath, and phenyl chloroformate (0.32 ml, 2.6 mmol) in THF (20 ml) was added dropwise. The reaction mixture was stirred for 16 hr, during which time it attained R.T. The reaction mixture was diluted with EtOAc, washed with sat'd NH$_4$Cl solution, dried (Na$_2$SO$_4$), filtered and concentrated. Subjection of the residue to flash chromatography (CH$_2$Cl$_2$) afforded the product (0.39 g, 48%). $^1$H NMR (CDCl$_3$, 400 MHz) δ 7.65 (1H, s), 7.48 (2H, m), 7.38–7.20 (6H, m), 7.00 (1H, m), 2.9 (1H, b). MS (m/e) 315 (M+H)$^+$.

Step 5

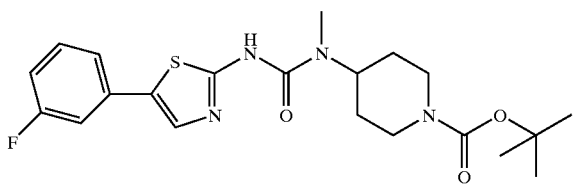

20-5

A mixture of the product of Step 4 (390 mg, 1.24 mmol), Preparation 1 (266 mg, 1.24 mmol) and Et$_3$N (0.5 ml, 3.6 mmol) in THF (25 ml) was refluxed for 3 hr. The reaction mixture was allowed to cool, diluted with EtOAc, washed with sat'd NH$_4$Cl solution, dried (Na$_2$SO$_4$), filtered and concentrated. Subjection of the residue to flash chromatography (2:98 MeOH/CH$_2$Cl$_2$) afforded the product (537 mg, 100%). $^1$H NMR (CDCl$_3$, 400 MHz) δ 9.54 (1H, b), 7.51 (1H, s), 7.29 (3H, m), 6.96 (1H, m), 4.39 (1H, m), 4.21 (2H, b), 2.88 (3H, s), 2.78 (2H, m), 1.63 (4H, m), 1.45 (9H, s). MS (m/e) 435 (M+H)$^+$.

Step 6

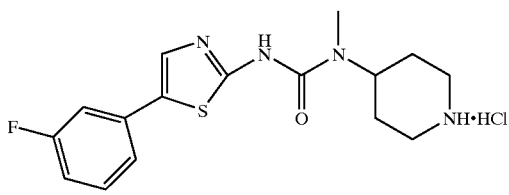

20-6

Reaction of the product of Step 5 with HCl by essentially the procedure of Example 6, Step 4 gave the product. $^1$H NMR (CD$_3$OD, 400 MHz) δ 8.00 (1H, s), 7.58–7.41 (3H, m), 7.19 (1H, m), 4.42 (1H, m), 3.54 (2H, m), 3.20 (2H, m), 3.07 (3H, s), 2.15 (2H, m), 2.01 (2H, m). MS (m/e) 335 (M+H)$^+$.

Step 7

Reaction of the product of Step 6 (20 mg, 0.05 mmol) with methyl isocyanate (1 drop) by essentially the procedure of Example 15 followed by PTLC (10:90 MeOH/CH$_2$Cl$_2$) gave the product (7 mg, 36%). MS m/e 392 (M+H)$^+$.

EXAMPLE 21

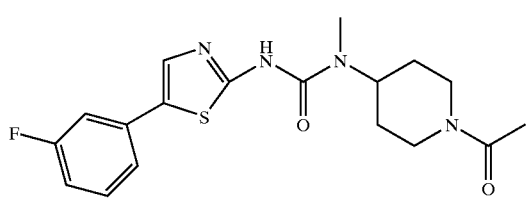

21

Reaction of 20-6 with acetyl chloride essentially the procedure of Example 4 gave the product. MS m/e 377 (M+H)$^+$.

EXAMPLE 22

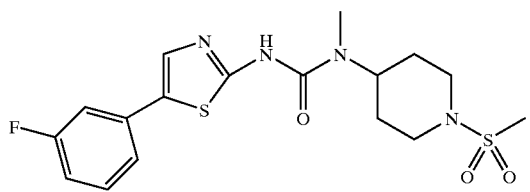

22

Reaction of 20-6 with methanesulfonyl chloride by the procedure of Example 3, Step 3 gave the product. $^1$H NMR (CDCl$_3$, 400 MHz) δ 7.52 (1H, s), 7.34 (1H, m), 7.22 (1H, m), 7.21 (1H, m), 6.97 (1H, m), 4.40 (1H, m), 3.92 (2H, m), 2.91 (3H, s), 2.79 (3H, s), 2.75 (2H, m), 1.83 (4H, m). MS m/e 413 (M+H)$^+$.

EXAMPLE 23

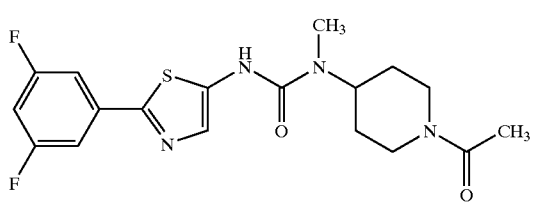

23

Step 1

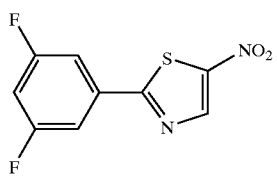

23-1

To a solution of 2-bromo-5-nitrothiazole (0.784 g, 3.75 mmol) and 0.5 M 3,5-difluorophenylzinc bromide in THF (5.0 ml, 12.5 mmol) was added Pd(PPh₃)₄ (0.173 g, 0.15 mmol) under argon. The reaction mixture was stirred at R.T. for 30 min. then poured into water (25 ml). The whole was extracted with CH₂Cl₂ (3×50 ml) dried (Na₂SO₄), filtered, and evaporated. The residue was subjected to PTLC (1:10 EtOAc/hexane) to give the product (0.49 g, 81%). ¹H NMR (CDCl₃) δ 8.59 (s, 1H), 7.52 (m, 2H), 7.01 (m, 1H). MS m/e 243 (M+H)⁺.

Step 2

23-2

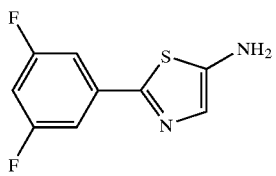

To a solution of the product of Step 1 (0.300 g, 1.24 mmol) in MeOH (20 ml) was added nickel chloride hexahydrate (0.589 g, 2.48 mmol) and sodium borohydride (0.187 g, 4.95 mmol) at 0° C. The reaction mixture was stirred at R.T. for 10 min. and quenched with water (10 ml). The mixture was filtered via celite. The celite was washed with CH₂Cl₂ (100 ml). The filtrate was extracted with CH₂Cl₂ (3×50 ml), and the combined organic layers were dried (Na₂SO₄), filtered, and evaporated. The residue was subjected to PTLC (1:2 EtOAc/hexane) to give the product (0.060 g, 23%). ¹H NMR (CDCl₃) δ 7.30 (m, 2H), 7.1 (s, 1H), 6.77 (m, 1H), 3.90 (bs, 2H). MS m/e 213 (M+H)⁺.

Step 3

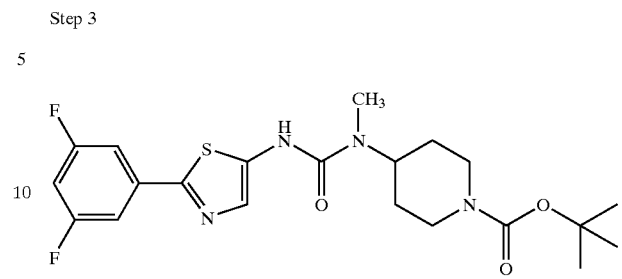

23-3

To a solution of the product of Step 2 (0.080 g, 0.377 mmol) in anhydrous pyridine (3.0 ml) was added phenyl chloroformate (0.071 ml, 0.566 mmol) slowly. The reaction mixture was stirred at R.T. overnight and evaporated. To a solution of the residue in chloroform (5 ml) and was added Preparation 1 (0.122 g, 0.567 mmol) and Et₃N (0.16 ml, 1.13 mmol). The reaction mixture was refluxed for 21 hr, allowed to cool and poured into water (25 ml). The whole was extracted with CH₂Cl₂ (3×50 ml), dried (Na₂SO₄), filtered and evaporated (1:20 MeOH/CH₂Cl₂) to give the product (0.087 g, 51%) as a solid. ¹H NMR (CDCl₃) δ 7.78 (s, 1H), 7.43 (s, 1H), 7.36 (m, 2H), 6.78 (m, 1H), 4.4 (bs, 1H), 4.2 (bs, 1H), 3.82 (bs, 1H), 2.89 (s, 3H), 2.78 (m, b, 2H), 1.8–1.5 (m, 4H), 1.45 (s, 9H). MS m/e 453 (M+H)⁺.

Step 4

Subjection of the product of Step 3 to the procedures of Example 3, Steps 2 and 3 gave the product. ¹H NMR (CDCl₃) δ 8.04 (s, 1H), 7.54 (s, 1H), 7.38 (m, 2H), 6.78 (m, 1H), 4.78 (m, 1H), 4.51 (m, 1H), 3.95 (m, 1H), 3.20 (m, 1H), 2.92 (m, 3H), 2.61 (m, 1H), 2.11 (s, 3H), 1.75 (m, 2H), 1.59 (m, 2H). MS m/e 395 (M+H)⁺.

Use of the appropriate reagents and procedures afforded the following compounds:

| | STRUCTURE | ¹H NMR | MS (M + H)⁺ |
|---|---|---|---|
| 23A | | (CDCl₃) δ 7.52 (s, 1H), 7.40 (m, 3H), 6.80 (m, 1H), 4.22 (m, 1H), 3.93 (m, 2H), 2.94 (s, 3H), 2.77 (m, 5H), 1.82 (m, 4H). | 431 |
| 23B | | (CDCl₃) δ 7.51 (s, 1H), 7.41 (m, 3H), 6.80 (m, 1H), 4.80 (m, 1H), 4.50 (m, 1H), 3.95 (m, 1H), 3.15 (m, 1H), 2.91 (s, 3H), 2.60 (m, 1H), 2.32 (m, 2H), 1.80–1.50 (m, 6H), 0.98 (t, 3H). | 423 |

-continued
| STRUCTURE | ¹H NMR | MS (M + H)⁺ |
|---|---|---|
| 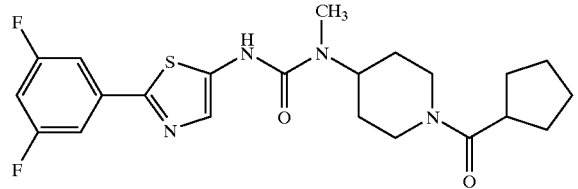 23C | (CDCl₃) δ 7.52 (s, 1H), 7.46 (s, 1H), 7.40 (m, 2H), 6.79 (m, 1H), 4.80 (m, 1H), 4.50 (m, 1H), 4.15 (m, 1H), 3.15 (m, 1H), 2.89 (s, 3H), 2.70 (m, 1H), 2.60 (m, 1H), 1.9–1.5 (m, 12H). | 449 |
| 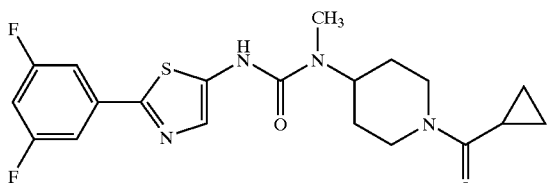 23D | (CDCl₃) δ 7.62 (s, 1H), 7.47 (s, 1H), 7.40 (m, 2H), 6.80 (m, 1H), 4.78 (m, 1H), 4.50 (m, 1H), 4.32 (m, 1H), 3.20 (m, 1H), 2.91 (s, 3H), 2.62 (m, 1H), 1.80–1.60 (m, 5H), 0.99 (m, 2H), 0.80 (m, 2H). | 421 |
| 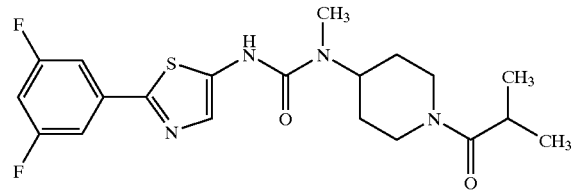 23E | (CDCl₃) δ 7.73 (s, 1H), 7.46 (s, 1H), 7.38 (m, 2H), 6.80 (m, 1H), 4.80 (m, 1H), 4.50 (m, 1H), 4.03 (m, 1H), 3.14 (m, 1H), 2.91 (s, 3H), 2.82 (m, 1H), 2.59 (m, 1H), 1.95–1.62 (m, 2H), 1.57 (m, 2H). 1.16 (m, 6H). | 423 |
| 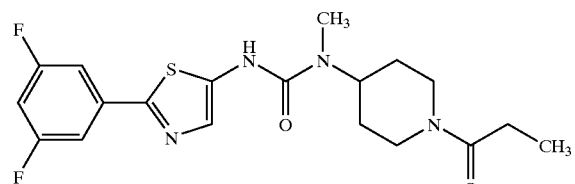 23F | (CDCl₃) δ 7.49 (s, 1H), 7.45 (s, 1H), 7.40 (m, 2H), 6.79 (m, 1H), 4.80 (m, 1H), 4.50 (m, 1H), 3.95 (m, 1H), 3.18 (m, 1H), 2.91 (s, 3H), 2.60 (m, 1H), 2.37 (q, 2H), 1.80–1.50 (m, 4H), 1.16 (t, 3H). | 409 |
EXAMPLE 24
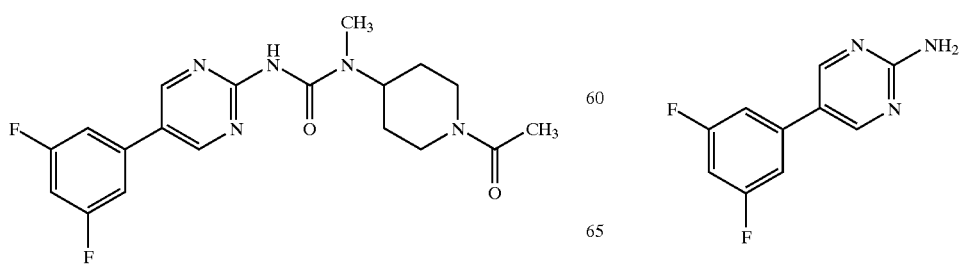

A flask charged with 3,5-difluorophenylboronic acid (4.40 g, 27.9 mmol), 2-amino-5-bromopyrimidine (4.00 g, 23 mmol), toluene (40 ml), water (7 ml) and cesium carbonate (8.20 g, 25.2 mmol) was purged with $N_2$. PdCl$_2$(dppf)$_2 \cdot CH_2Cl_2$ (0.94 g, 1.15 mmol) was added and the reaction mixture was refluxed for 2.5 hr. The reaction mixture was allowed to cool then poured into water (100 ml). The whole was extracted with EtOAc (3×150 ml), dried (Na$_2$SO$_4$), filtered and concentrated. Subjection of the residue to flash chromatography (gradient 1:5 to 1:1 acetone/hexane) gave the product (2.30 g, 48%). $^1$H NMR (CDCl$_3$) δ 8.29 (s, 2H), 6.84 (m, 2H), 6.62 (m, 1H), 4.18 (s, 2H). MS m/e 208 (M+H)$^+$.

24-2

Step 2

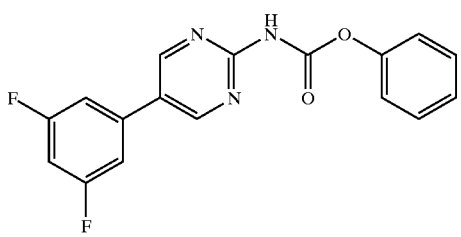

To a solution of the product of Step 1 (0.500 g, 2.42 mmol) in anhydrous pyridine (6 ml) was added phenyl chloroformate (0.33 ml, 2.62 mmol) dropwise. The reaction mixture was stirred for 16 hr, then evaporated. The residue was subjected to PTLC (1:30 CH$_3$OH/CH$_2$Cl$_2$) to give the product (0.30 g, 38%). $^1$HNMR (CDCl$_3$) δ 8.84 (m, 3H), 7.42 (m, 2H), 7.26 (m, 3H), 7.06 (m, 2H), 6.89 (m, 1H). MS m/e 328 (M+H)$^+$.

24-3

Step 3

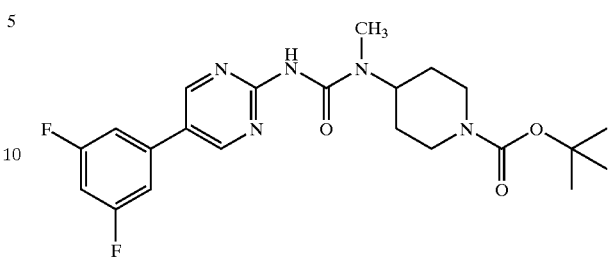

To a solution of the product of Step 2 (0.145 g, 0.44 mmol) in chloroform (5 ml) was added Preparation 1 (0.095 g, 0.44 mmol) and Et$_3$N (0.19 ml, 1.33 mmol). The reaction mixture was refluxed for 3 hr, allowed to cool and poured into water (15 ml). The whole was extracted with EtOAc (3×), and the combined organic layers were dried (Na$_2$SO$_4$), filtered and evaporated. The residue was subjected to PTLC (1:30 CH$_3$OH/CH$_2$Cl$_2$) to give the product (0.205 g, 100%). $^1$H NMR (CDCl$_3$) δ 8.71 (s, 2H), 7.70 (s, b, 1H), 7.01 (m, 2H), 6.83 (m, 1H), 4.36 (m, 1H), 4.21 (m, 2H), 2.92 (s, 3H), 2.78 (m, 2H), 1.74 (m, 2H), 1.63 (m, 2H), 1.45 (s, 9H). MS m/e 448 (M+H)$^+$.

Step 4

Subjection of the product of Step 3 to the procedures of Example 10, Steps 3 and 4 gave the product. $^1$H NMR (CDCl$_3$) δ 8.71 (s, 2H), 7.62 (s, b, 1H), 7.02 (m, 2H), 6.84 (m, 1H), 4.78 (m, 1H), 4.43 (m, 1H), 3.90 (m, 1H), 3.18 (m, 1H), 2.92 (s, 3H), 2.60 (m, 1H), 2.09 (s, 3H), 1.82 (m, 2H), 1.60 (m, 2H). MS m/e 390 (M+H)$^+$.

Use of the appropriate reagents and procedures afforded the following compounds.

| STRUCTURE | $^1$H NMR | MS (M + H)$^+$ |
|---|---|---|
| 24A | (CDCl$_3$) δ 8.74 (s, 2H), 7.42 (s, b, 1H), 7.04 (m, 2H), 6.83 (m, 1H), 4.43 (m, 1H), 3.95 (m, 2H), 2.97 (s, 3H), 2.80 (m, 5H), 1.88 (m, 4H). | 426 |
| 24B | (CDCl$_3$) δ 8.73 (s, b, 2H), 7.59 (s, b, 1H), 7.03 (m, 2H), 6.83 (m, 1H), 4.79 (m, 1H), 4.47 (m, 1H), 3.94 (m, 1H), 3.09 (m, 1H), 2.92 (s, 3H), 2.59 (m, 1H), 2.35 (m, 2H), 1.82 (m, 2H), 1.61 (m, 2H), 1.15 (m, 3H). | 404 |

EXAMPLE 25

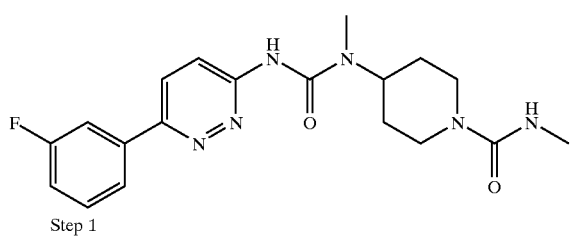

Step 1

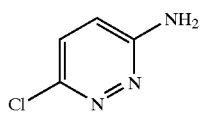

A mixture of 3,6-dichloropyridazine (7.5 g) and NH$_3$ (9 g) in EtOH (100 ml) was heated at 130° C. in stainless steel bomb for 16 hr. After the reaction mixture had cooled to R.T., it was concentrated, and the residue was subjected to Soxhlet extraction (EtOAc). The residue obtained from the EtOAc extract was recrystallized from EtOAc to give the product (3.81 g).

Step 2

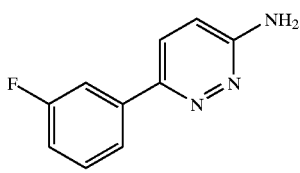

A suspension of the product of Step 1 (200 mg, 1.54 mmol), 3-fluorophenylboronic acid (260 mg, 1.86 mmol), and 2M K$_2$CO$_3$ (1.6 ml, 3.2 mmol) in EtOH (3 ml) and toluene (10 ml) was purged with N$_2$. Pd(PPh$_3$)$_4$ (90 mg, 0.08 mmol) was added, and the mixture was heated at 110° C. for 24 hr. The cooled reaction mixture was concentrated and partitioned between water and EtOAc. The organic layer was washed with water, dried (Na$_2$SO$_4$), filtered and evaporated. Subjection of the residue to PTLC (7:93 MeOH/CH$_2$Cl$_2$) gave the product (168 mg, 58%).

Step 3

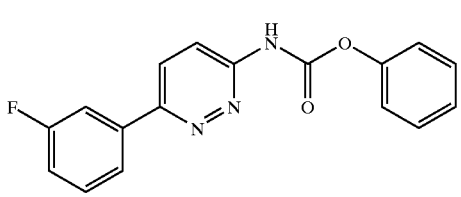

Reaction of the product of Step 2 by essentially the procedure of Example 20, Step 4 gave the product $^1$H NMR (CDCl$_3$, 400 MHz) δ 8.75 (1H, b), 8.43 (1H, m), 7.95 (1H, m), 7.82–7.78 (2H, m), 7.52–7.18 (7H, m). MS m/e 310 (M+H)$^+$.

Step 4

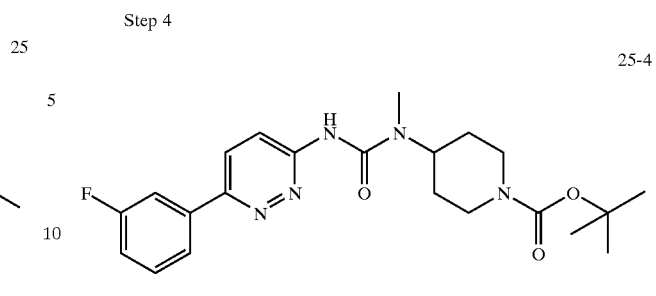

Reaction of the product of Step 3 with Preparation 1 by essentially the procedure of Example 20, Step 5 gave the product. $^1$H NMR (CDCl$_3$, 400 MHz) δ 8.6 (1H, b), 8.36 (1H, m), 7.80 (1H, m), 7.73 (2H, m), 7.44 (1H, m), 7.12 (1H, m), 4.41 (1H, m), 4.21 (2H, m), 2.99 (3H, s), 2.80 (2H, m), 1.79–1.60 (4H, m), 1.43 (9H, s). MS m/e 430 (M+H)$^+$.

Step 5

Subjection of the product of Step 4 by the procedure of Example 20, Steps 6 and 7 gave the product. $^1$H NMR (CDCl$_3$, 400 MHz) δ 8.40 (1H, m), 8.20 (1H, b), 7.82 (1H, m), 7.50 (2H, m), 7.42 (1H, m), 7.15 (1H, m), 4.54 (1H, m), 4.44 (1H, m), 4.09 (2H, m), 2.98 (3H, s), 2.90 (2H, m), 2.79 (3H, s), 1.75–1.64 (4H, m). MS m/e 387 (M+H)$^+$.

Use of the appropriate procedures afforded the following compounds:

EXAMPLE 26

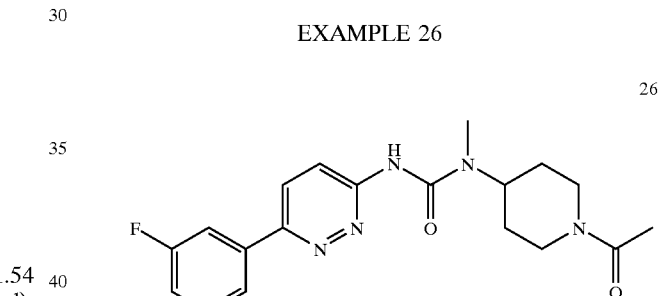

$^1$H NMR (CDCl$_3$, 400 MHz) δ 8.6 (1H, b), 8.34 (1H, m), 7.80 (1H, m), 7.73 (2H, m), 7.44 (1H, m), 7.13 (1H, m), 4.76 (1H, m), 4.50 (1H, m), 3.89 (1H, m), 3.15 (1H, m), 2.99 (3H, s), 2.25 (1H, m), 2.09 (3H, s), 1.79 (2H, m), 1.63 (2H, m). MS m/e 372 (M+H)$^+$.

EXAMPLE 27

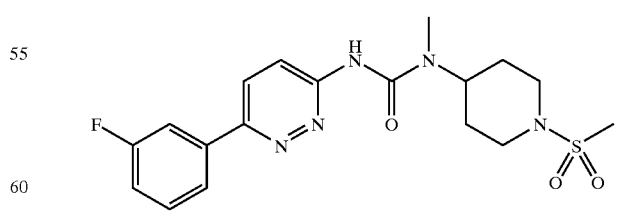

$^1$H NMR (CDCl$_3$, 400 MHz) δ 8.47 (1H, m), 7.86 (1H, m), 7.77 (2H, m), 7.47 (1H, m), 7.17 (1H, m), 4.47 (1H, m), 3.97 (2H, m), 3.02 (3H, s), 2.83 (2H, m), 2.82 (3H, s), 1.93–1.50 (4H, m). MS m/e 408 (M+H)$^+$.

What is claimed:

1. A compound of Formula I:

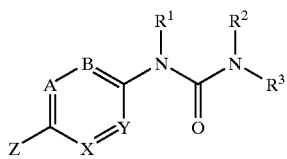

or a pharmaceutically acceptable salt or hydrate of said compound,
wherein
=A-B= is =C(R$^4$)—C(R$^5$)= and —X=Y— is —C(R$^6$)=N—, or —N=C(R$^7$)—, Z is

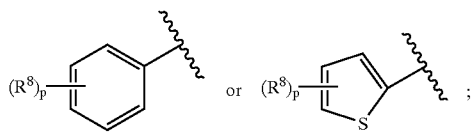

R$^1$ is H or —(C$_1$-C$_6$)alkyl;
R$^2$ is H, —(C$_1$-C$_6$)alkyl, —(C$_3$-C$_7$)cycloalkyl or R$_5$—(C$_1$-C$_6$)alkyl(C$_3$-C$_7$)cycloalkyl;

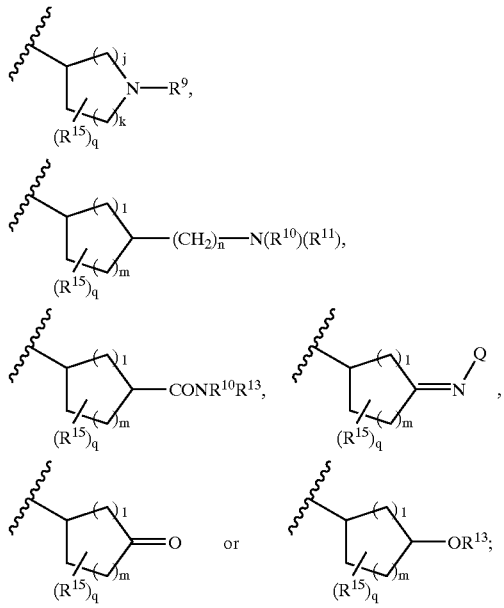

Q is —OR$^{13}$, or —NR$^{13}$R$^{14}$;
j is 1 or 2;
k is 0, 1 or 2;
l is 0, 1 or 2;
m is 0, 1 or 2;
n is 0 to 6;
p is 1, 2 or 3;
q is 1 or 2;
R$^4$, R$^5$, R$^6$ and R$^7$ may be the same or different, and are independently selected from H, —OH, halogen, haloalkyl, —(C$_1$-C$_6$)alkyl, —(C$_3$-C$_7$)cycloalkyl, —(C$_1$-C$_6$)alkyl(C$_3$-C$_7$)cycloalkyl, —CN, NR$^{10}$R$^{11}$, NR$^{13}$R$^{14}$, —O(C$_1$-C$_6$)alkyl, —O(C$_3$-C$_7$)cycloalkyl, —O(C$_1$-C$_6$)alkyl(C$_3$-C$_7$)cycoalkyl, —S(C$_1$-C$_6$)alkyl, —S(C$_3$-C$_7$)cycloalkyl and —S(C$_1$-C$_6$)alkyl(C$_3$-C$_7$) cycloalkyl;

R$^8$ may be the same or different, and is independently selected from H, halogen, —OH, haloalkyl, haloalkoxy, —CN, —NO$_2$, —(C$_1$-C$_6$)alkyl, —(C$_3$-C$_7$)cycloalkyl, —(C$_1$-C$_6$)alkyl(C$_3$-C$_7$)cycloalkyl, NR$^{10}$R$^{11}$, NR$^{13}$R$^{14}$, —O(C$_1$-C$_6$)alkyl, —O(C$_3$-C$_7$)cycloalkyl, —O(C$_1$-C$_6$)alkyl(C$_3$-C$_7$)cycloalkyl and —CONR$^{13}$R$^{14}$;

R$^9$ is —SO$_2$(C$_1$-C$_6$)alkyl, —SO$_2$(C$_3$-C$_7$)cycloalkyl, —SO$_2$(C$_1$-C$_6$)alkyl(C$_3$-C$_7$)cycloalkyl, —SO$_2$(C$_1$-C$_6$) haloalkyl, —SO$_2$[hydroxy(C$_2$-C$_6$)alkyl], —SO$_2$ [amino(C$_2$-C$_6$)alkyl], —SO$_2$[alkoxy(C$_2$-C$_6$)alkyl], —SO$_2$[alkylamino(C$_2$-C$_6$)alkyl], —SO$_2$[dialkylamino (C$_2$-C$_6$)alkyl], —SO$_2$(aryl), —SO$_2$(heteroaryl), —SO$_2$ [aryl(C$_1$-C$_6$)alkyl], —SO$_2$NR$^{13}$R$^{14}$, —CO(C$_1$-C$_6$) alkyl, —CO(C$_3$-C$_7$)cycloalkyl, —CO(C$_1$-C$_6$)alkyl (C$_3$-C$_7$)cycloalkyl, CO(C$_1$-C$_6$)haloalkyl, —C(O)aryl, —C(O)heteroaryl, —CONR$^{13}$R$^{14}$, —C(S)NR$^{13}$R$^{14}$, aryl, heteroaryl, —(CH$_2$)CONR$^{13}$R$^{14}$, —C(=NCN) alkylthio, —C(=NCN)NR$^{13}$R$^{14}$, —(C$_1$-C$_6$)alkyl, —(C$_3$-C$_7$)cycloalkyl, —(C$_1$-C$_6$)alkyl(C$_3$-C$_7$) cycloalkyl, —(C$_1$-C$_6$)alkylaryl, —(C$_1$-C$_6$) alkylheteroaryl or —COOR$^{12}$;

R$^{10}$ is H or alkyl;

R$^{11}$ is H, —(C$_1$-C$_6$)alkyl, —(C$_3$-C$_7$)cycloalkyl, —(C$_1$-C$_6$)alkyl(C$_3$-C$_7$)cycloalkyl, aryl, heteroaryl, —SO$_2$(C$_1$-C$_6$)alkyl, —SO$_2$(C$_3$-C$_7$)cycloalkyl, —SO$_2$ (C$_1$-C$_6$)alkyl(C$_3$-C$_7$)cycloalkyl, —SO$_2$(C$_1$-C$_6$) haloalkyl, —SO$_2$(aryl), —SO$_2$(heteroaryl), —CO (C$_1$-C$_6$)alkyl, —CO(C$_3$-C$_7$)cycloalkyl, —CO(C$_1$-C$_6$) alkyl(C$_3$-C$_7$)cycloalkyl, —C(O)aryl, —C(O) heteroaryl, —CONR$^{13}$R$^{14}$ or —COOR$^{12}$;

R$^{12}$ is —(C$_1$-C$_6$)alkyl, —(C$_3$-C$_7$)cycloalkyl, —(C$_1$-C$_6$) alkyl(C$_3$-C$_7$)cycloalkyl, —(C$_1$-C$_6$)alkylaryl, —(C$_1$-C$_6$)alkylheteroaryl, aryl or heteroaryl;

R$^{13}$ and R$^{14}$ may be the same or different and are independently H, —(C$_1$-C$_6$)alkyl, —(C$_3$-C$_7$) cycloalkyl, —(C$_1$-C$_6$)alkyl(C$_3$-C$_7$)cycloalkyl, —(C$_1$-C$_6$)alkylaryl, aryl or heteroaryl; and, R$^{15}$ may be the same or different, and is H, —(C$_1$-C$_6$) alkyl, —(C$_3$-C$_7$)cycloalkyl, —(C$_1$-C$_6$)alkyl(C$_3$-C$_7$) cycloalkyl, aryl, heteroaryl, —CN, —CONR$^{13}$R$^{14}$, —COOR$^{13}$, —OH, —O(C$_1$-C$_6$)alkyl, —O(C$_3$-C$_7$) cycloalkyl, —O(C$_1$-C$_6$)alkyl(C$_3$-C$_7$)cycloalkyl, —NR$^{10}$R$^{11}$, —NR$^{13}$R$^{14}$, or a —(C$_1$-C$_6$)alkyl group substituted by an aryl, heteroaryl, hydroxy, alkoxy, —NR$^{10}$R$^{11}$, —NR$^{13}$R$^{14}$, —CONR$^{13}$R$^{14}$, or —COOR$^{13}$ group.

2. A compound as defined in claim 1 wherein

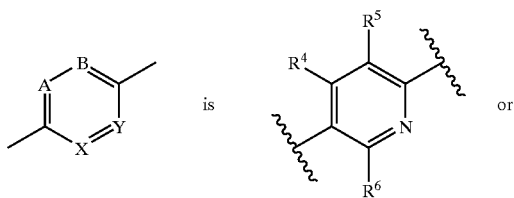

-continued

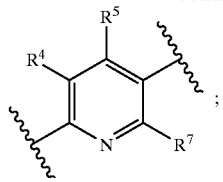

$R^{15}$ is H and $R^3$ is

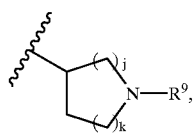

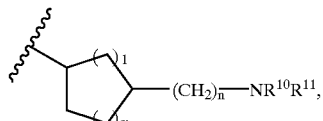

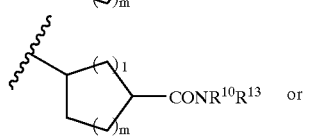

the sum of j and k is 2 or 3;
and the sum of l and m is 2 or 3.

3. A compound as defined in claim 1 wherein
$R^1$ is hydrogen,
$R^2$ is hydrogen or $(C_1-C_6)$alkyl,
$R^4$, $R^5$, $R^6$ and $R^7$ are hydrogen or halogen,
$R^8$ may be the same or different, and is independently selected from H, halogen, —O$(C_1-C_6)$alkyl, —OH, haloalkyl and haloalkoxy,
$R^9$ is —SO$_2$$(C_1-C_6)$alkyl, —SO$_2$$(C_3-C_7)$cyloalkyl, —SO$_2$$(C_1-C_6)$alkyl$(C_3-C_7)$cycloalkyl, —SO$_2$aryl, —SO$_2$heteroaryl, —SO$_2$NR$^{13}$R$^{14}$, —CO$(C_1-C_6)$alkyl, —CO$(C_3-C_7)$cycloalkyl, —CO$(C_1-C_6)$alkyl$(C_3-C_7)$cycloalkyl, —C(O)aryl, —C(O)heteroaryl, aryl, heteroaryl,
$R^{10}$ is H or —$(C_1-C_6)$alkyl,
$R^{11}$ is —SO$_2$$(C_1-C_6)$alkyl, Q is —OR$^{13}$ or —NR$^{13}$R$^{14}$;
$R^{13}$ and $R^{14}$ may be the same or different, and are independently H or —$(C_1-C_6)$alkyl;
the sum of j and k is 2 or 3;
the sum of l and m is 2 or 3; and
n is 0 to 6.

4. A compound as defined in claim 1 wherein
$R^{15}$ is H and $R^3$ is

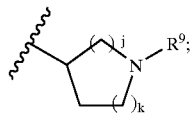

$R^9$ is —SO$_2$$(C_1-C_6)$alkyl, —SO$_2$$(C_3-C_7)$cycloalkyl, —SO$_2$aryl, —SO$_2$heteroaryl, —CO$(C_1-C_6)$alkyl, —CO$(C_3-C_7)$cycloalkyl, —CO$(C_1-C_6)$alkyl$(C_3-C_7)$cycloalkyl, —C(O)aryl, —C(O)heteroaryl, aryl, or heteroaryl, and
the sum of j and k is 2 or 3.

5. The compound as defined in claim 1 of the formula

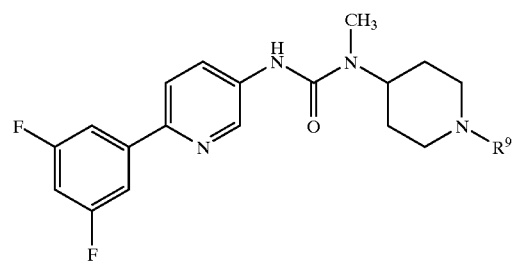

or a pharmaceutically acceptable salt or hydrate of said compound, wherein $R^9$ is as shown in the table below:

| Example | $R^9$ |
|---|---|
| 1 | 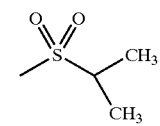 |
| 3 | —SO$_2$CH$_3$ |
| 4 | ![cyclopropyl ketone] |
| 1G | ![2,6-dimethylpyridinyl] |
| 1H | ![5-fluoro-2-methylpyridinyl] |
| 1I | ![2-methylthiazolyl] |
| 3E | ![cyclopropyl methylsulfonyl] |
| 3F | ![ethyl methylsulfonyl] |
| 3G | ![propyl methylsulfonyl] |
| 3H | ![isopropyl methylsulfonyl] |

-continued

| Example | R⁹ |
|---|---|
| 4B | 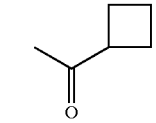 |
| 4C | 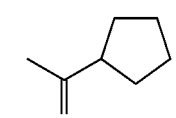 |
| 4D | 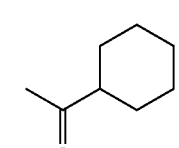 |
| 4E | 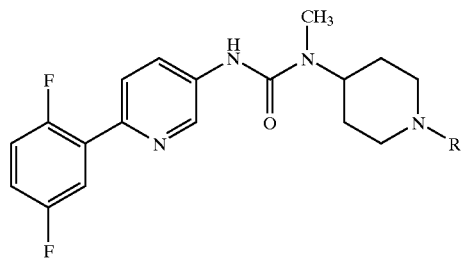 |
| 4F | 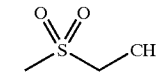 |
| 4G | 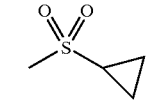 |
| 4H | 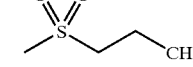 |
| 4I | 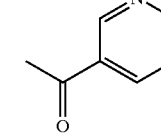 |
| 4J | (not shown) |
| 4K | (not shown) |
| 4L | (not shown) |
| 4M | (not shown) |

-continued

| Example | R⁹ |
|---|---|
| 4N | (cyclobutyl methyl ketone) |
| 4O | (cyclopentyl methyl ketone) |
| 4P | (cyclohexyl methyl ketone) |

6. The compound as defined in claim 1 of the formula or a pharmaceutically acceptable salt or hydrate of said compound, wherein R⁹ is as shown in the table below:

| Example | R⁹ |
|---|---|
| 3I | —SO₂CH₃ |
| 3J | (methylsulfonyl ethyl) |
| 3K | (methylsulfonyl cyclopropyl) |
| 3L | (methylsulfonyl propyl) |
| 4Z | (3-pyridyl methyl ketone) |

-continued

| Example | R⁹ |
|---|---|
| 4AA | (cyclopropyl-C(=O)-CH₂-) |
| 4BB | CH₃CH₂-C(=O)-CH₂- |
| 4CC | (CH₃)₂CH-C(=O)-CH₂- |
| 4DD | CH₃-C(=O)-CH₂- |
| 4EE | CH₃CH₂-C(=O)- (propionyl, -CH₂-C(=O)-CH₃ type) |
| 4FF | thiazol-5-yl-C(=O)-CH₂- |

7. The compound as defined in claim 1 of the formula

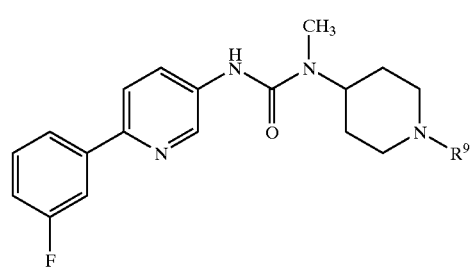

or a pharmaceutically acceptable salt or hydrate of said compound, wherein R⁹ is as shown in the table below:

| Example | R⁹ |
|---|---|
| 3N | —SO₂CH₃ |
| 3O | methylsulfonyl-cyclopropyl |

8. The compound as defined in claim 1 of the formula

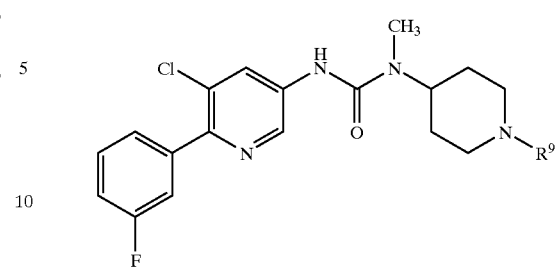

or a pharmaceutically acceptable salt or hydrate of said compound, wherein R⁹ is as shown in the table below:

| Example | R⁹ |
|---|---|
| 5 | CH₃-C(=O)-CH₂- |
| 5A | —SO₂CH₃ |
| 5B | CH₃-S(O)₂-CH₂CH₃ (methylsulfonyl-ethyl) |
| 5C | CH₃-S(O)₂-CH₂CH₂CH₃ |
| 5D | CH₃-S(O)₂-CH(CH₃)₂ |
| 5E | methylsulfonyl-cyclopropyl |
| 5F | CH₃CH₂-C(=O)-CH₂- |
| 5G | cyclopropyl-C(=O)-CH₂- |
| 5H | CH₃CH₂-C(=O)-CH(CH₃)- or CH₃-C(=O)-CH₂CH₂- |
| 5I | (CH₃)₂N-C(=O)-CH₂- |

-continued

| Example | R⁹ |
|---|---|
| 5J | 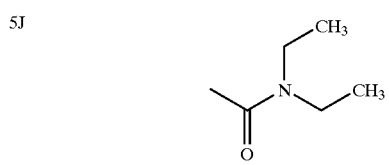 |
| 5K | 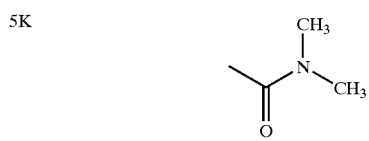 |

9. The compound as defined in claim 3 of the formula

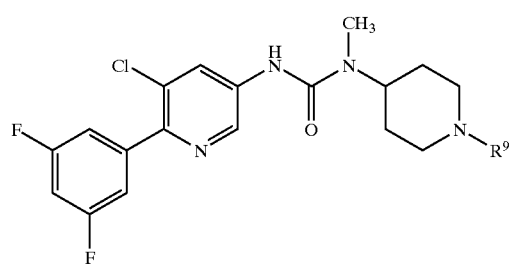

or a pharmaceutically acceptable salt or hydrate of said compound,
wherein R⁹ is as shown in the table below:

| Example | R⁹ |
|---|---|
| 5M | —SO₂CH₃ |
| 5N |  |
| 5O | 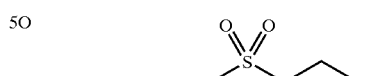 |
| 5P | 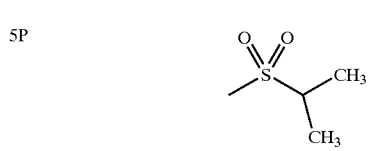 |
| 5Q |  |

10. The compound as defined in claim 1 of the formula

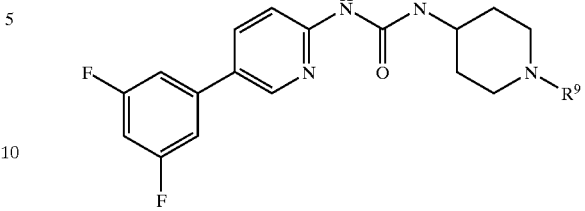

or a pharmaceutically acceptable salt or hydrate of said compound,
wherein R⁹ is as shown in the table below:

| Example | R⁹ |
|---|---|
| 6 |  |
| 6B | —SO₂CH₃ |
| 6C | 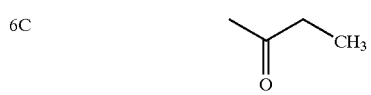 |
| 6D | 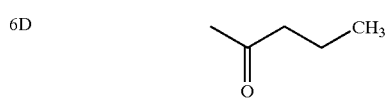 |

11. The compound as defined in claim 1 of the formula

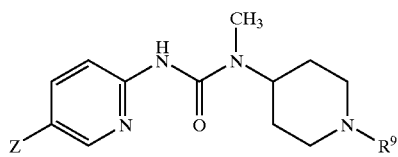

or a pharmaceutically acceptable salt or hydrate of said compound,
wherein Z and R⁹ are as shown in the table below:

| Example | Z | R⁹ |
|---|---|---|
| 7 | 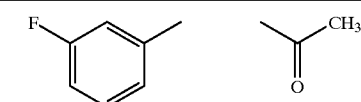 | 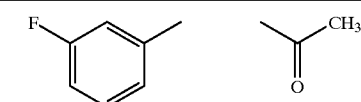 |
| 7B | 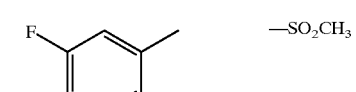 | —SO₂CH₃ |
| 7C | 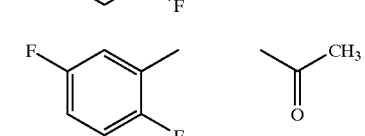 | 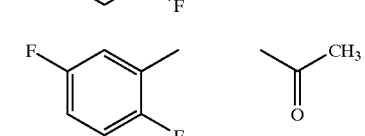 |

-continued

| Example | Z | R⁹ |
|---|---|---|
| 7D | 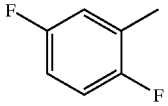 | 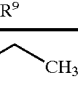 |
| 7E | 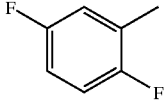 | 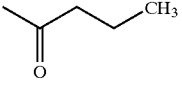 |
| 7F | 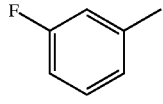 | —SO₂CH₃ |
| 7G |  | 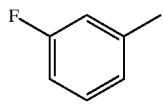 |

12. A pharmaceutical composition which comprises an effective amount of a compound as defined in claim 1 and a pharmaceutically acceptable carrier therefor.

13. A method of treating eating disorders, obesity and disorders related to obesity comprising administering to a mammal in need of such treatment a therapeutically effective amount of a compound of claim 1 or a pharmaceutically acceptable salt of said compound.

14. The method of claim 13 wherein said eating disorder is hyperphagia.

15. The method of claim 13 wherein said metabolic disorder is obesity.

16. A method of treating a disorder associated with obesity comprising administering to a mammal in need of such treatment a therapeutically effective amount of a compound of claim 1 thereof or a pharmaceutically acceptable salt of said compound.

17. The method of claim 16 wherein the disorder associated with obesity is type II diabetes, insulin resistance, hyperlipidemia or hypertension.

18. A pharmaceutical composition which comprises a therapeutically effective amount of a composition comprising a first compound, said first compound being a compound of claim 1, thereof, or a pharmaceutically acceptable salt of said compound;

a second compound, said second compound being a $\beta_3$ agonist, a thryomimetic agent, an eating behavior modifying agent or an NPY antagonist; and a pharmaceutically acceptable carrier therefor.

19. A method of treating an eating disorder which comprises administering to a mammal in need of such treatment an amount of a first compound, said first compound being a compound of claim 1 or a pharmaceutically acceptable salt of said compound;

a second compound, said second compound being a $\beta_3$ agonist, a thryomimetic agent, an eating behavior modifying agent or an NPY antagonist;

wherein the amounts of the first and second compounds result in a therapeutic effect.

20. A pharmaceutical composition which comprises a therapeutically effective amount of a composition comprising a first compound, said first compound being a compound of claim 1 or a pharmaceutically acceptable salt of said compound;

a second compound, said second compound being an aldose reductase inhibitor, a glycogen phosphorylase inhibitor, a sorbitol dehydrogenase inhibitor, insulin, metformin, acarbose, a thiazolidinedione such as troglitazone or rezulin; a glitazone such as rosaglitazone or pioglitazone; a sulfonylurea, glipazide, glyburide, or chlorpropamide; and a pharmaceutically acceptable carrier therefor.

21. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO.        : 6,946,476 B2
APPLICATION NO. : 10/177345
DATED             : September 20, 2005
INVENTOR(S)       : Andrew Stamford et al.

It is certified that error appears in the above-identified patent and that said Letters Patent is hereby corrected as shown below:

Claim 1, col. 129, line 29:    Please correct "$R_5$-$(C_1$-$C_6)$alkyl$(C_3$-$C_7)$cycloalkyl"    to -- -$(C_1$-$C_6)$alkyl$(C_3$-$C_7)$cycloalkyl --

Claim 1, col. 129, line 30:    Please correct

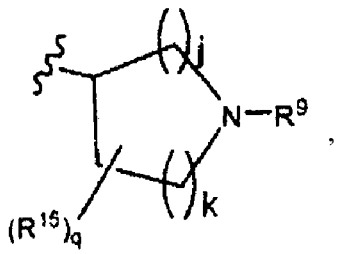

to

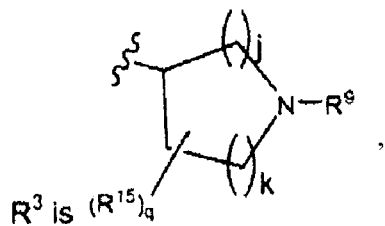

Signed and Sealed this

Twenty-seventh Day of May, 2008

JON W. DUDAS
*Director of the United States Patent and Trademark Office*